(12) United States Patent
Donaldson et al.

(10) Patent No.: US 7,053,268 B1
(45) Date of Patent: May 30, 2006

(54) PROMOTER

(75) Inventors: Iain Alasdair Donaldson, Frederiksberg (DK); Thomas Bruun Rasmussen, Nakskov (DK)

(73) Assignee: Danisco A/S, Copenhagen (DK)

( * ) Notice: Subject to any disclaimer, the term of this patent is extended or adjusted under 35 U.S.C. 154(b) by 335 days.

(21) Appl. No.: 10/009,570

(22) PCT Filed: Jun. 15, 2000

(86) PCT No.: PCT/GB00/02641

§ 371 (c)(1),
(2), (4) Date: Jun. 19, 2002

(87) PCT Pub. No.: WO00/78975

PCT Pub. Date: Dec. 28, 2000

(30) Foreign Application Priority Data

Jun. 17, 1999 (GB) .................................. 9914210

(51) Int. Cl.
*A01H 1/00* (2006.01)

(52) U.S. Cl. ..................... 800/287; 800/298; 536/24.1; 435/71.1; 435/252.3; 435/254.11; 435/320.1; 435/419; 435/468

(58) Field of Classification Search ............... 536/24.1; 435/320.1, 419, 252.3, 69.1, 71.1, 254.11, 435/468; 800/287, 298
See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 4,816,567 | A | 3/1989 | Cabilly et al. |

FOREIGN PATENT DOCUMENTS

| | | |
|---|---|---|
| CA | 2006454 | 6/1990 |
| WO | WO 94/24292 A2 | 10/1994 |
| WO | WO 94/25575 A1 | 11/1994 |
| WO | WO 95/10616 A2 | 4/1995 |
| WO | WO 96/01323 A1 | 1/1996 |
| WO | WO 96/29415 A1 | 9/1996 |
| WO | WO 96/29416 A1 | 9/1996 |
| WO | WO 97/03574 A1 | 2/1997 |
| WO | WO 97/31102 A1 | 8/1997 |
| WO | 10062 | 3/1998 |
| WO | WO 98/54335 A1 | 12/1998 |
| WO | WO 99/50399 A2 | 10/1999 |

OTHER PUBLICATIONS

Burkhardt et al. Transgenic rice (Oryza sativa) endosperm expressing daffodil (Narcissus pseudonarcissus) phytoene synthase accumulates phytoene, a key intermediate of provitamin A biosynthesis. Plant J. May 1997;11(5):1071-8.*

Kim Y et al. A 20 nucleotide upstream element is essential for the nopaline synthase (nos) promoter activity. Plant Mol Biol. Jan. 1994 ;24(1):105-17.* de Pate S et al. A 22-bp fragment of the pea lectin promoter containing essential TGAC-like mofifs confers seed-specific gene expression.Plant Cell. Aug. 1993;5(8):877-86.*

Dolferus R. et al. Differential interactions of promoter elements in stress responses of the Arabidopsis Adh gene. Plant Physiol Aug. 1994;105(4):1075-87.*

Huang J. et al. Complete structures of three rice sucrose synthase isogenes and differential regulation of their expressions Biosci Biotechnol Biochem. Feb. 1996;60(2):233-9.*

Wing et al. CUGI Rice BAC Library Oryza sativa (japonica cultivar-group) genomic clone nbxb0027L15f, genomic survey sequence, Nov. 3, 1998, GenEMBL Accession No. AQ272200.*

Wing et al. A BAC End Sequencing Framework to Sequence the Rice Genome, Database EMGSS3 'Online!, 1998, EMBL Heidelberg, Germany (Abstract).*

Invitrogen Catalogue 1997 "Original TA Cloning Kits, pCR2.1 vector", p. 7.*

Huang et al., "Complete Structures of Three Rice Sucrose Synthase Isogenes and Differential Regulation of Their Expression," *Bioscience Biotechnology and Biochemistry* 60(2):233-239 (1996).

Wang et al., "A Complete Sequence of the Rice Sucrose Synthast-1 RSS1 Gene," *Plant Molecular Biology* 19(5):881-885 (1992).

Wing et al. "A BAC End Sequencing Framework to Sequence the Rice Genome," Database EMGSS3 'Online! (1998) EMBL Heidelberg, Germany (Abstract).

"Original TA Cloning Kits. pCR2.1 vector" Invitrogen Catalogue, p. 7, 1997.

Bloomfield, "Condensation of DNA by Multivalent Cations: Considerations on Mechanism", *Biopolymers* (1991), vol. 31, pp. 1471-1481.

Donovan et al., "The Growth of Detached Wheat Heads in Liquid Culture," *Plant Science Letters* (1977), vol. 9, pp. 107-113.

Kikkert, "The Biolistic ® PDS-1000/He device," *Plant Cell Tissue and Organ Culture* (1993), vol. 33, pp. 221-226.

Knudsen et al., "Transformation of the developing barley endosperm by particle bombardment," *Planta* (1991), vol. 185, pp. 330-336.

(Continued)

Primary Examiner—Cynthia Collins
(74) Attorney, Agent, or Firm—Foley & Lardner LLP

(57) ABSTRACT

A promoter is described. The promoter comprises a nucleotide sequence corresponding to that shown as SEQ ID No. 1 or a variant, homologue or derivative thereof.

31 Claims, 27 Drawing Sheets

OTHER PUBLICATIONS

Siebert et al., "An improved PCR method for walking in uncloned genomic DNA," *Nucleic Acids Research* (1995), vol. 23, No. 6, pp. 1087-1088.

Copeland, "Enzymes of Sucrose Metabolism," *Methods in Plant Biochemistry*, vol. 3 (1990), pp. 73-85, Academic Press Limited.

Dörmann et al., "The role of UDP-glucose epimerase in carbogydrate metabolism of *Arbidopsis*," *The Plant Journal* (1998), vol. 13, No. 5, pp. 641-652.

Finer et al., "Development of the particle inflow gun for DNA delivery to plant cells," *Plant Cell Reports* (1992), vol. 11, pp. 323-328.

Jefferson, "Assaying Chimeric Genes in Plants: The GUS Gene Fusion System," *Plant Molecular Biology Reporter* (1987), Vo. 5, No. 4, pp. 387-405.

Karrer et al., "Metabolic regulation of rice α-amylase and sucrose synthase genes *in planta*," *The Plant Journal* (1992), vol. 2, No. 4 pp. 517-523.

Klein et al., "High-velocity microprojectivles for delivering nucleic acids into living cells," *Nature* (1987), vol. 327, pp. 70-73.

Klein et al., "Transfer of foreign genes into intact maize cells with high-velocity microprojectives," *Proc. Natl. Acad. Sci. USA* (1988), vol. 85, pp. 4305-4309.

Lopes et al., "Endosperm Origin, Development, and Function," *The Plant Cell* (1993), vol. 5, pp. 1383-1399.

Sanford et al., "Delivery of Substances into Cells and Tissues Using a Particle Bombardment Process," *Particulate Science and Technology* (1987), vol. 5, No. 1, pp. 27-37.

Thomas, "Gene Expression during Plant Embryogenesis and Germination: An Overview," *The Plant Cell* (1993), vol. 5, pp. 1401-1410.

Vain et al., "Development of the Particle Inflow Gun," *Plant Cell, Tissue and Organ Culture* (1993), vol. 33, pp. 237-246.

West et al., "Embryogenesis in Higher Plants: An Overview," *The Plant Cell* (1993), vol. 5, pp. 1361-1369.

Whistler et al., *Guar: Agronomy, Production, Industrial Use, and Nutrition* (1979), Purdue University Press, West Lafayette, Indiana.

Bäumlein et al., "Cis-analysis of a seed protein gene promoter: the conservative RY repoeat CATGCATG within the legumin box is essential for tissue-specific expression of a legumin gene," *The Plant Journal* (1992), vol. 2, No. 2, pp. 233-239.

Joshi, "An inspection of the domain between putative TATA box and translation start site in 79 plant genes," *Nucleic Acids Research* (1987), vol. 15, No. 16, pp. 6643-6653.

Marzabal et al., "The bifactorial endosperm box of γ-zein gene: characterisation and function of the Pb3 and GZM cis-acting elements," *The Plant Journal* (1998), vol. 16, No. 1, pp. 41-52.

Muller et al., "The nitrogen response of a barley C-hordein promoter is controlled by positive and negative regulation of the GCN4 and endosperm box," *The Plant Journal* (1993), vol. 4, No. 2, pp. 343-355.

Simpson et al., "Splicing of precursors to mRNA in higher plants: mechanism regulation and sub-nuclear organisation of the spliceosomal machinery," *Plant Molecular Biology* (1996), vol. 32, pp. 1-41.

\* cited by examiner

FIG. 3

```
1
  ACTTTAGATAATAAAGTAAGTCACAAGAAAAATAAATAATAATTCCAAATTTTTTTAATA
  TGAAATCTATTATTTCATTCAGTGTTCTTTTTATTTATTATTAAGGTTTAAAAAAATTAT

Eam1105I
61
  AGACGAGTGGTCAAACAGTACAAGTAAAAACTCAAAATTCCTTATATTATGGGACTTATA
  TCTGCTCACCAGTTTGTCATGTTCATTTTTGAGTTTTAAGGAATATAATACCCTGAATAT

121
  TTATGGGACGGAGGAAGTAGAAGATTGTAGCCAAGAAAAAAACAAAAACAAACACACCGC
  AATACCCTGCCTCCTTCATCTTCTAACATCGGTTCTTTTTTGTTTTGTTTGTGTGGCG

Ppu10I
              NsiI
            SphI
181
  CACCTGGCAGGCATGCATCTTAGGTCGGCACATTGAGAGGTCGGCAGTAGACGAGTTACC
  GTGGACCGTCCGTACGTAGAATCCAGCCGTGTAACTCTCCAGCCGTCATCTGCTCAATGG

Eco57I    NheI
241
  CTACACAACTGCTTCTTCAGTGAGCTAGCTGCATGTTCTGTTCTGCATTTACATTGCAGG
  GATGTGTTGACGAAGAAGTCACTCGATCGACGTACAAGACAAGACGTAAATGTAACGTCC

NheI                      ClaI
301
  CAGCAGCTAGCAACAGTTTGCAGGAACAATCGATAATCCATTGTGTCAGGGAGGAACATG
  GTCGTCGATCGTTGTCAAACGTCCTTGTTAGCTATTAGGTAACACAGTCCCTCCTTGTAC

PvuII
              BpmI       Esp3I      BsiWI       Eco57I
361
  GAGAAAAACCGGGGCTGGAGACGAACGGGAGCAGCTGTACCGTACGTTTCTGAAGGCTGA
  CTCTTTTTGGCCCCGACCTCTGCTTGCCCTCGTCGACATGGCATGCAAAGACTTCCGACT

Eco57I
421
  ACCCATCTGCGAAATCCGCAGATTGGTTTGTTCAATTCCAACTTGCAGTCCTTCAGATTG
  TGGGTAGACGCTTTAGGCGTCTAACCAAACAAGTTAAGGTTGAACGTCAGGAAGTCTAAC

481
  GTTGCATGTTCAACCGTAGTACATCTGAAAAATGAAGTGTTAAATACCTTGAGAAGACCT
  CAACGTACAAGTTGGCATCATGTAGACTTTTACTTCACAATTTATGGAACTCTTCTGGA

PstI
        SphI  Sse8387I                                    BstBI
541
  TCATGGAAGCATGCCTGCAGGCGATTAGCTAAGAAAAAAAAAATAAATGTACTTTTCGAA
  AGTACCTTCGTACGGACGTCCGCTAATCGATTCTTTTTTTTTATTTACATGAAAAGCTT
```

```
601          .         .         .         .         .         .
   ACTTAATTTTGGAGTTAGATTTTAGGGTGTTTCCATCGTAGTGTATTTTCTACTATTGCA
   TGAATTAAAACCTCAATCTAAAATCCCACAAAGGTAGCATCACATAAAAGATGATAACGT

DraI
661          .         .         .         .         .         .
   GTTTAAACCGCTAATAGTCAGATATAAAATTTTATCTATAGATCATTTATAAATCATTTT
   CAAATTTGGCGATTATCAGTCTATATTTTAAAATAGATATCTAGTAAATATTTAGTAAAA

MunI
                                                          BclI
721          .         .         .         .         .         .
   TAGTTGCTTCGTTCATTTTTCTACCACTTATCAACCATAGCTCAACTGATCAATTGACAA
   ATCAACGAAGCAAGTAAAAAGATGGTGAATAGTTGGTATCGAGTTGACTAGTTAACTGTT

781          .         .         .         .         .         .
   TAAAAGTTACTAAACGACATCGCTCATCACACACCCAACGCTCACCGATGGGTGCCTCTC
   ATTTTCAATGATTTGCTGTAGCGAGTAGTGTGTGGGTTGCGAGTGGCTACCCACGGAGAG

BssSI                              BsaBI
841          .         .         .         .         .         .
   GACCACGAGTTTAGCACTTGTGCAACATATATGCGTGCGATGAACATCTACTGATGCGCC
   CTGGTGCTCAAATCGTGAACACGTTGTATATACGCACGCTACTTGTAGATGACTACGCGG

Ppu10I
                                                 BlpI        NsiI
          BspHI                          AlwNI  Esp3I        SphI
901          .         .         .         .         .         .
   ATGCGAATTTTAGCGTTCGTTCATGACGCTTCCAACGGCACAGAGGCTGAGCAGCAGCAT
   TACGCTTAAAATCGCAAGCAAGTACTGCGAAGGTTGCCGTGTCTCCGACTCGTCGTCGTA

Ppu10I
    NsiI
    SphI
961          .         .         .         .         .         .
   GCATGCATGGCTCTTGTGAAAACAAAAAAGGTTACTGGTAAATGACATGCTGCTGTAGCT
   CGTACGTACCGAGAACACTTTTGTTTTTTCCAATGACCATTTACTGTACGACGACATCGA

NdeI
                              Ppu10I
              BsmI            NsiI
1021         .         .         .         .         .         .
   AGTTAGCAGAATGCAAGGCCCATGCATATGCAATGCTATGCAACAAGTATAGTACCAGCA
   TCAATCGTCTTACGTTCCGGGTACGTATACGTTACGATACGTTGTTCATATCATGGTCGT

BssSI
1081         .         .         .         .         .         .
   TGTATGGTAGCCAGCTAACTAATCTATCAGCAGAGGCAGCAAGCTCGTGCATGGTGTGAT
   ACATACCATCGGTCGATTGATTAGATAGTCGTCTCCGTCGTTCGAGCACGTACCACACTA

XcmI
         BpmI                                           NdeI
1141         .         .         .         .         .         .
   GCACTTCTCTCCAGTAATCTAGTGGTAATTTTCACCCAAAGCGTTGCTCATATGGACAGT
   CGTGAAGAGAGGTCATTAGATCACCATTAAAAGTGGGTTTCGCAACGAGTATACCTGTCA
```

FIG. 3CONT'D

```
              SspI
1201      .         .         .         .         .         .
    AATTAGTAATATTACCAAGGTTCACAATCCCGTTACCTGACCAAATACTACTCACGAATG
    TTAATCATTATAATGGTTCCAAGTGTTAGGGCAATGGACTGGTTTATGATGAGTGCTTAC

1261      .         .         .         .         .         .
    GTATCTCTGGTTTTCGTTAAAACCGTTGGTAAACCAGCAAAAATAGACAAAATTTGTCAA
    CATAGAGACCAAAAGCAATTTTGGCAACCATTTGGTCGTTTTTATCTGTTTTAAACAGTT

DraI
1321      .         .         .         .         .         .
    AATTTTAAATTTTAGTTTTTTTTTTAACTTAGCCGGGAAACCTTGAAGTTTGTGCTGTCG
    TTAAAATTTAAAATCAAAAAAAAAATTGAATCGGCCCTTTGGAACTTCAAACACGACAGC

BsgI
1381      .         .         .         .         .         .
    AGCTGTCCTGGGAAGGACGGTTTTGGTTGGGATTGTGAACCCTGGTTACTGCACTTCATT
    TCGACAGGACCCTTCCTGCCAAAACCAACCCTAACACTTGGGACCAATGACGTGAAGTAA

1441      .         .         .         .         .         .
    TTTGAACAGATATTAGTGCAACAGACAAATGCCAACGCATTTTTTTCTGTTTACCGGCAA
    AAACTTGTCTATAATCACGTTGTCTGTTTACGGTTGCGTAAAAAAGACAAATGGCCGTT

HindIII
        Eco57I                             BspMI           Esp3I
1501      .         .         .         .         .         .
    GCTGAAGCTTTTACGATCCCCATACCGCCGTTGCTGCAAACCTGCCAAGAAAGAGCAGCA
    CGACTTCGAAAATGCTAGGGGTATGGCGGCAACGACGTTTGGACGGTTCTTTCTCGTCGT 1561      .         .         .         .         .         .
    GAAACAGGTGTCATTTTGTGGTGGAAAGCCAAGTAAAGTAAACAGAAGATGGAAGATAGT
    CTTTGTCCACAGTAAAACACCACCTTTCGGTTCATTTCATTTGTCTTCTACCTTCTATCA BsgI
1621      .         .         .         .         .         .
    GAGGACCAGGGAGTGAGGCAGGGGACACATGGCCCACGCCTCCCTGCACATTTTCGTGTA
    CTCCTGGTCCCTCACTCCGTCCCCTGTGTACCGGGTGCGGAGGGACGTGTAAAAGCACAT Ppu10I
               NsiI                                     Esp3I
1681      .         .         .         .         .         .
    TAAATACAGGTGGATGCATCGCTCTCCCAGCATCCATCGGTTCTCTGCTCTGTTCATCCA
    ATTTATGTCCACCTACGTAGCGAGAGGGTCGTAGGTAGCCAAGAGACGAGACAAGTAGGT EarI     Eco57I           EarI
1741      .         .         .         .         .         .
    TAGAGTTTCCTCCTCTTCTCCTTCAGTGCAAGGTAGAGAAGAGCATGTGTGTGTGTGTGT
    ATCTCAAAGGAGGAGAAGAGGAAGTCACGTTCCATCTCTTCTCGTACACACACACACACA BsgI
1801      .         .         .         .         .         .
    GTGAACTGTGAAGTGCAGAGTGCTTCTGTAGTTCTGTGTTATGTCCATAGTGATCTTGTT
    CACTTGACACTTCACGTCTCACGAAGACATCAAGACACAATACAGGTATCACTAGAACAA
```

FIG. 3 CONT'D

```
               Ppu10I
               NsiI
1861     .         .         .         .         .         .
    AGGATTGTTGCTATGGATGCATGATGTTATGGTTAATCTCTGAATTACAGTAGGGACTTC
    TCCTAACAACGATACCTACGTACTACAATACCAATTAGAGACTTAATGTCATCCCTGAAG

BglII
1921     .         .         .         .         .         .
    TCTGAGATCTCTGGATTAGTGGGGGGTGCTAAATTTTTTTCTGGTTGCATCAGCTTGGGT
    AGACTCTAGAGACCTAATCACCCCCCACGATTTAAAAAAAGACCAACGTAGTCGAACCCA

1981     .         .         .         .         .         .
    TTCTGGGATTGGTGTGGGTTCTTGCTCTGAATTTTGGTTCAGAATGTCGATTTGTTTTGT
    AAGACCCTAACCACACCCAAGAACGAGACTTAAAACCAAGTCTTACAGCTAAACAAAACA

BspMI
           Eco57I                                       PstI
2041     .         .         .         .         .         .
    GTTTGCCCTCTGAAGTTGAGAGTAGCTATGATCCATCCAGCACAGAACTGCAGGTCCCTG
    CAAACGGGAGACTTCAACTCTCATCGATACTAGGTAGGTCGTGTCTTGACGTCCAGGGAC

NgoMI
      NaeI
2101     .         .         .         .         .         .
    CCTGCCGGCAGCATATACAGGACATGCCATTTTGCAAGCTCTGGGCTTATGGTTTCTCTT
    GGACGGCCGTCGTATATGTCCTGTACGGTAAAACGTTCGAGACCCGAATACCAAAGAGAA

2161     .         .         .         .         .         .
    TTGGAGTTCTTCTTCTTGCATGATCTGTGTTCTCTAACAAAGAAGCAAGATTTAGCAACT
    AACCTCAAGAAGAAGAACGTACTAGACACAAGAGATTGTTTCTTCGTTCTAAATCGTTGA

2221     .         .         .         .         .         .
    TTATTCAGAGACAAGAAAAGGATCTGGCAACCTTTTGTTTCTGTTTTATCCTACTCGTAA
    AATAAGTCTCTGTTCTTTTCCTAGACCGTTGGAAAACAAAGACAAAATAGGATGAGCATT

DraI
2281     .         .         .         .         .         .
    AGATTGTTATTTAAGCAAAAATTTCCCAAAAGTTTTAAATATAATTTCCATGATGTGCCA
    TCTAACAATAAATTCGTTTTTAAAGGGTTTTCAAAATTTATATTAAAGGTACTACACGGT

2341     .         .         .         .         .         .
    CTCTCATGTCCTTGAACCTGGCACTCATTATGGGCTCCTCAGAAGTGCTGTAGCTAATGT
    GAGAGTACAGGAACTTGGACCGTGAGTAATACCCGAGGAGTCTTCACGACATCGATTACA

BsaBI
2401     .         .         .         .         .         .
    CACTAATCTTTTGTATCTTTGTTCGTAGTCTTGTATTTTATGATGCTTATCCCTTTGTGC
    GTGATTAGAAAACATAGAAACAAGCATCAGAACATAAAATACTACGAATAGGGAAACACG

2461     .         .         .         .         .         .
    TTTCCATGTTTGATGTCCAAATGTCATGGCAATGTTTTTGACTTCTAGTAGGGGTTTTAG
    AAAGGTACAAACTACAGGTTTACAGTACCGTTACAAAAACTGAAGATCATCCCCAAAATC
```

FIG.3 CONT'D

```
2521
     TACCTTTTTGTTAGATAAGTACATCCAAATTCTGTTTATTTATTCAAAAATCATTCTGTT
     ATGGAAAAACAATCTATTCATGTAGGTTTAAGACAAATAAATAAGTTTTTAGTAAGACAA

PflMI
2581
     TATTCACTGAAAACATTTGTCCATTCAATGGAATCGTAAACTGTCTGTGTTTTTCAGGCT
     ATAAGTGACTTTTGTAAACAGGTAAGTTACCTTAGCATTTGACAGACACAAAAAGTCCGA

BamHI
2641                        2668
     TGAGGATCCAACTAGAAGATAGCAATGG
     ACTCCTAGGTTGATCTTCTATCGTTACC
```

FIG. 3CONT'D

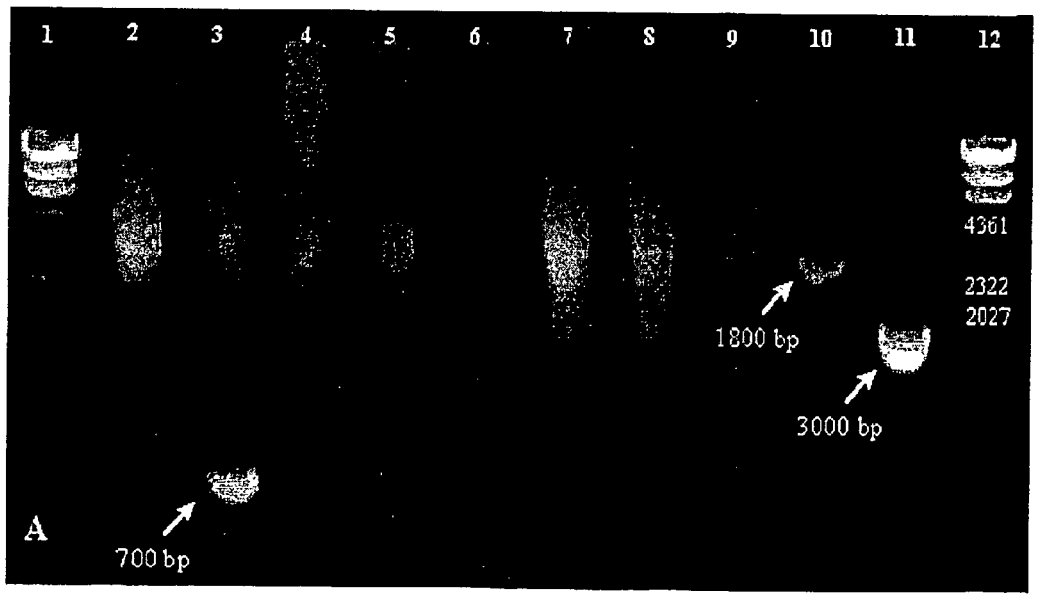

Agarose gel showing the result of the semi-nested PCR with the primer pair AP2 and RSus3. Lane 1 and 12 molecular weight marker II; lane 2-6 EcoRV, DraI, PvuII, ScaI and SspI with buffer F: lane 7-11 same with buffer H.

FIG. 4

The promoter region from pScaK3 and pSspK3 were amplified from the primers M13 forward and RSusNco. The amplified products contain XhoI and NcoI sites for directional cloning into the unique SalI and NcoI in pGUSNOSt as XhoI/NcoI fragments.

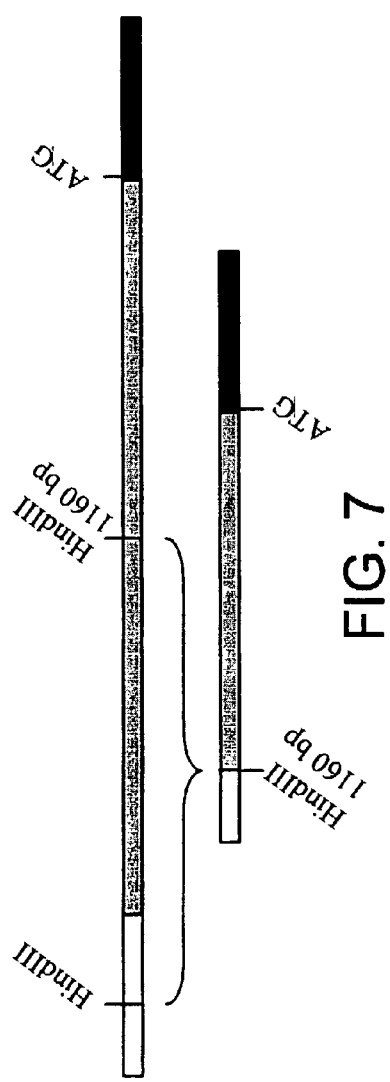
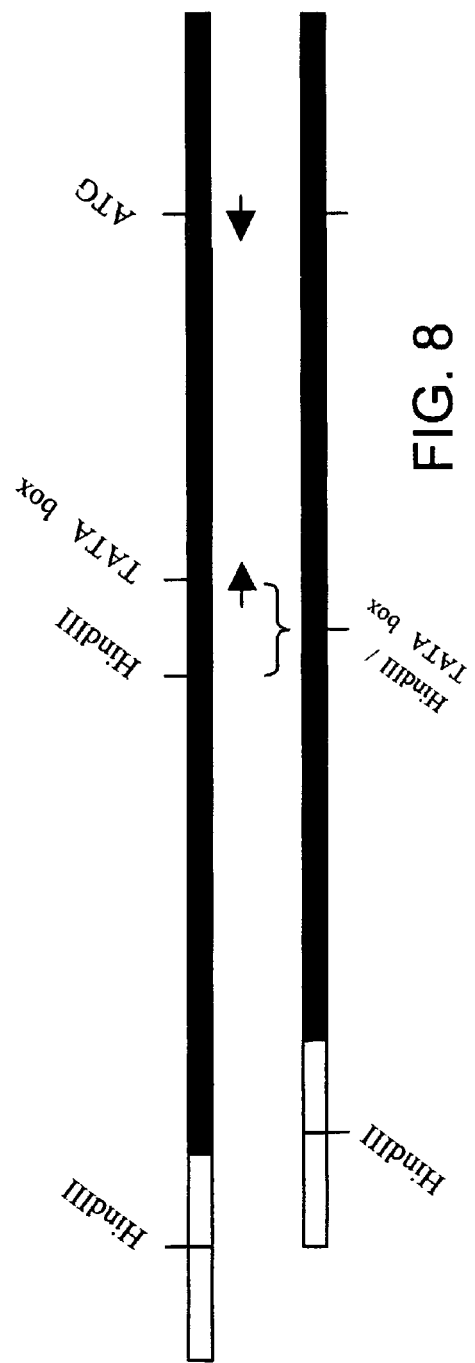
FIG. 7
FIG. 8

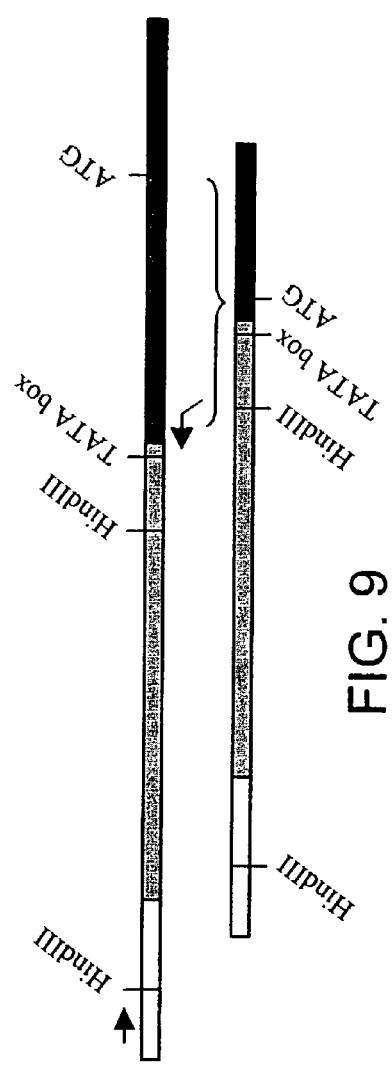
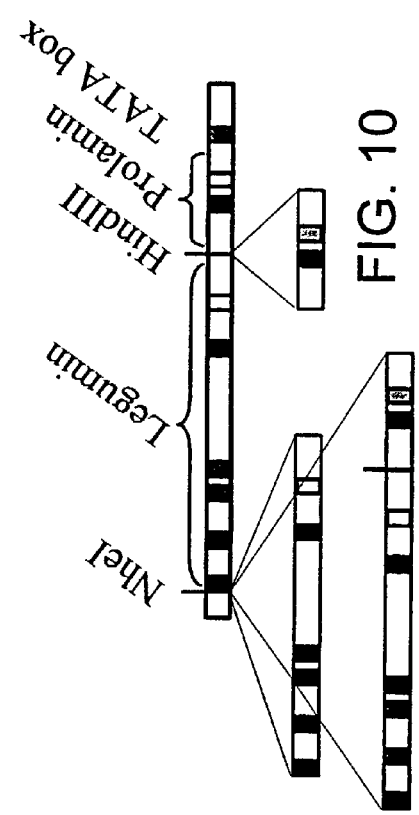
FIG. 9
FIG. 10

Agarose gel showing the result of a digest of tandem repeat clones. Lane 1: HindIII digest of pTandem leg/pro, which gives a specific fragment of 740 bp. Lane 2: NheI digest of pTandem legumin, which gives a specific fragment of 570 bp. Lane 3: DNA marker VI. Lane 4: HindIII digest of pTandem prolamin, which gives a specific fragment of 160 bp.

PROMOTER

FIELD OF THE PRESENT INVENTION

The present invention relates to a promoter, including a construct and an expression vector comprising the same and a transformed cell comprising the same. In addition the present invention relates to a plant cell, as well as a plant, comprising the same.

BACKGROUND OF THE PRESENT INVENTION

Expression of plant genes is controlled in a complex pattern during the life cycle of a plant. Several processes are involved in this regulation of gene expression. The main steps are; the initiation of transcription; the termination of transcription; the processing of transcripts; the transport of mRNA to the ribosomes; and the translation.

Three examples of plant genes that are expressed are found in Huang et al (1996 Biosci Biotech Biochem 60 (2) 233–239) who report on three rice sucrose synthase isogenes, which are called RSus1, RSus2 and RSus3. The authors also report on their differential regulation of their expression. The authors state that the gene organisation patterns of RSus2 and RSus3 were the same.

One of the major processes controlling gene expression is initiation of transcription. The transcription is initiated by binding of RNA polymerase together with several transcription factors to the promoter region. Specific regulatory DNA sequences (cis-elements) in the promoter serve as binding sites for these transcription factors (trans-acting factors).

The cis-elements found in plant gene promoters can be divided in two categories. The first category comprises those cis-elements which are involved in initiation of transcription. The TATA box and the CAAT box are examples of proximal cis-elements involved in initiation of transcription. The CAAT box defines the binding site for the RNA polymerase, and the TATA box directs the RNA polymerase to the correct transcription start site. Presence of multiple CAAT boxes normally indicate a constitutive promoter. The TATA box and CAAT box are conserved among prokaryotes and eukaryotes, but are not essential for the function of some plant gene promoters. The second category is composed of cis-elements which are involved in temporal and spatial regulation of gene expression. Genes encoding seed storage proteins (Glutamins, Legumins, Prolamins etc.) are examples of genes which are temporally and spatially regulated, and are thereby expressed in a tissue-specific and developmental manner. Examples of endosperm-specific cis-elements are the AACA motif and the endosperm box. These cis-elements, that contribute to tissue-specific and developmental expression of endosperm storage protein genes, are conserved among a wide range of seed storage protein genes.

The manner in which complex patterns of transcription factors act on specific cis-elements determines whether genes are more or less constitutively expressed, or are expressed at specific times during development. Furthermore, these interactions determine whether expression occurs in a specific tissue e.g. the endosperm, is displayed by several tissues e.g. those of the seed, or is common to all parts of the plant. Multiple trans-acting factors can recognise variants of the cis-element consensus sequences and compete for binding, yielding complex expression patterns. Each plant gene promoter has a set of transcription factors and other trans-acting factors, which interact with the promoter sequence and the RNA polymerase and thereby regulate gene expression in an unique pattern.

It is known that it is desirable to direct expression of a nucleotide sequence of interest ("NOI") in certain tissues of an organism—such as a plant. The NOI will typically encode a product of interest ("POI"). For example, it may be desirable to produce crop protein products with an optimised amino acid composition and so increase the nutritive value of the crop. It may even be desirable to use the crop to express non-plant genes such as genes for mammalian products. Examples of the latter products include interferons, insulin, blood factors and plasminogen activators.

However, whilst it may be desirable to achieve expression of a NOI in certain tissues it is sometimes important (if not necessary) to ensure that the NOI is not expressed in other tissues in such a manner that detrimental effects may occur. Moreover, it is important not to upset the normal metabolism of the organism to such an extent that detrimental effects occur. For example, a disturbance in the normal metabolism in a plant's leaf or shoot could lead to stunted growth of the plant.

An example of the use of plant promoters to cause expression of an NOI in plant tissue may be found in CA-A-2006454, which describes a DNA sequence of an expression cassette in which the potato tuber specific regulatory regions are localised. The expression cassette contains a patatin-gene with a patatin-gene promoter. The DNA sequence is transferred into a plant genome using *Agrobacterium*. According to CA-A-2006454, the DNA sequence enables heterologous products to be prepared in crops.

However, in plant transformation processes, it is generally the low efficiency of both transformation and regeneration that seriously slow vector development, since they limit the number of genetic constructs which can be tested. Investigations of the strength and tissue specificity of different transcriptional promoters, which can greatly influence the effect of the genetic manipulation, can be unmanageably labour-intensive if performed in stable transformants. This has resulted in a tendency to use strong constitutive promoters which are not tissue-specific to direct transgenic expression in stable transformants, e.g. from viruses (cauliflower mosaic virus 35S promoter) and *Agrobacterium* (nopaline synthase promoter (NOS)). Not the least problematic element of this approach occurs when lowering of gene expression by antisense transcription is attempted, because gratuitous suppression of gene expression in all tissues can result in developmental retardation of non-target tissues, or other weakening of the transformant. Under such circumstances, only those transformants, in which the genetic construct poorly suppresses gene expression, would be expected to survive selection. There is, therefore, a strong argument for the use of tissue-specific transcriptional promoters for directing antisense transcription, but, in many crop species, characterising such promoters in stable transformants is not feasible owing to low efficiency of transformation and regeneration.

Despite the fact that there are already some promoters available in the art, there is still a need to have additional promoters, in particular promoters that are efficient and/or selective in their ability to allow for the expression of a NOI.

Thus, the present invention seeks to provide a promoter that is capable of causing the expression (transcription) of a NOI.

More in particular, the present invention seeks to provide a promoter that is capable of directing the expression (transcription) of a nucleotide sequence of interest in specific tissues, or in just a specific tissue, of an organism, typically a plant.

SUMMARY ASPECTS OF THE PRESENT INVENTION

Aspects of the present invention are presented in the claims and in the following commentary.

In brief, some aspects of the present invention relate to:
1. A novel promoter capable of selective expression.
2. Novel promoter nucleotide sequences.
3. Expression systems comprising said promoters.
4. Methods of expression using said promoters.
5. Transformed hosts/host cells comprising said promoters.

As used with reference to the present invention, the terms "expression", "expresses", "expressed" and "expressable" are synonymous with the respective terms "transcription", "transcribes", "transcribed" and "transcribable". Hence, if the NOI is a coding sequence, then the product of its expression may also be called the transcription product and visa versa. Likewise, if the NOI is an anti-sense nucleotide sequence then the product of its transcription may also be called the expression product and visa versa.

In the following commentary references to "nucleotide sequence of the present invention" include references to the "promoter of the present invention" and vice versa. Also, the term "nucleotide sequence of the present invention" is synonymous with the phrase "polynucleotide sequence of the present invention".

Other aspects concerning the promoter and/or the nucleotide sequence of the present invention include: a construct comprising the sequences of the present invention; a vector comprising the sequences of the present invention; a plasmid comprising the sequences of present invention; a transformed cell comprising the sequences of the present invention; a transformed tissue comprising the sequences of the present invention; a transformed organ comprising the sequences of the present invention; a transformed host comprising the sequences of the present invention; a transformed organism comprising the sequences of the present invention. The present invention also encompasses methods of expressing NOIs using the same, such as expression in a host plant cell; including methods for transferring same.

For convenience, the promoter of the present invention is sometimes referred to as the RSus3 promoter (or even the Rsus3 promoter or even the RSus3 promoter). However, it is important to note that the promoter of the present invention is not disclosed in the teachings of Huang et al (ibid). Moreover, and contrary to the authors statement that "the gene organisation patterns of RSus2 and RSus3 were the same" we found that the promoter of RSus3 was quite different to that of RSus2.

In this respect, we found a very low degree of homology (i.e. identity) between the RSus3 promoter and the RSus2 promoter and also the RSus3 and RSus1 promoter—as evidenced by the following Table.

Homology scores of RSus1, RSus2, RSus3

| Alignment | % Homology[1] | % Homology[2] |
|---|---|---|
| RSus3 and RSus1 | 7.7% | 5.4% |
| RSus3 and RSus2 | 4.6% | 5.4% |
| RSus1 and RSus2 | 4.6% | 8.8% |

[1]Homology scores based on multiple alignment (all of the promoter region upstream of the translational start codon including the intron: RSus1 (2663 bp), RSus2 (2900 bp), RSus3 (2667 bp)).
[2]Homology scores based on multiple alignment (RSus1, RSus2, RSus3 following excision of intron 1).

The homology scores presented in the above table show the low degree of similarity between the promoter regions of RSus1, RSus2 and RSus3.

The percentage homologies were calculated using the multiple alignment feature in DNASIS™ (Hitachi Software), based on an algorithm, analogous to CLUSTAL (Higgins D G & Sharp P M (1988), Gene 73(1), 237–244).

In addition, and as a result of a sequence analysis of the sequences of the RSus3 promoter and the RSus1 promoter and the RSus2 promoter, we found that apart from the conserved TATA box and intron splice sites, they have no motifs in common.

Thus, contrary to the prior art teachings, we found that the gene organisation patterns of RSus2 and RSus3 are not the same.

For ease of reference, aspects of the present invention are now discussed under appropriate section headings. However, the teachings under each section are not necessarily limited to each particular section.

DETAILED ASPECTS OF THE PRESENT INVENTION

According to a first aspect of the present invention there is provided a promoter having the nucleotide sequence presented as SEQ ID No. 1, or a variant, homologue, fragment or derivative thereof.

Alternatively expressed, the present invention provides a nucleotide sequence selected from:
(a) the nucleotide sequence presented as SEQ ID No. 1;
(b) a nucleotide sequence that is a variant, homologue, derivative or fragment of the nucleotide sequence presented as SEQ ID No. 1;
(c) a nucleotide sequence that is the complement of the nucleotide sequence set out in SEQ ID No. 1;
(d) a nucleotide sequence that is the complement of a variant, homologue, derivative or fragment of the nucleotide sequence presented as SEQ ID No. 1;
(e) a nucleotide sequence that is capable of hybridising to the nucleotide sequence set out in SEQ ID No. 1;
(f) a nucleotide sequence that is capable of hybridising to a variant, homologue, derivative or fragment of the nucleotide sequence presented as SEQ ID No. 1;
(g) a nucleotide sequence that is the complement of a nucleotide sequence that is capable of hybridising to the nucleotide sequence set out in SEQ ID No. 1;
(h) a nucleotide sequence that is the complement of a nucleotide sequence that is capable of hybridising to a variant, homologue, derivative or fragment of the nucleotide sequence presented as SEQ ID No. 1;
(i) a nucleotide sequence that is capable of hybridising to the complement of the nucleotide sequence set out in SEQ ID No. 1;
(j) a nucleotide sequence that is capable of hybridising to the complement of a variant, homologue, derivative or fragment of the nucleotide sequence presented as SEQ ID No. 1;
(k) a nucleotide sequence comprising any one of (a), (b), (c), (d), (e), (f), (g), (h), (i), and/or (j).

In a preferred aspect, the promoter is obtainable from (though it does not have to be actually obtained from) a plant of the genus Oryza, preferably from *Oryza sativa*.

Another aspect of the present invention includes an isolated nucleotide sequence according to the present invention.

Additional aspects of the present invention include uses of the promoter for expressing NOIs in vitro (e.g. in culture media such as a broth) and/or in vivo (e.g. in a transformed organism).

In a highly preferred aspect the present invention provides a method for expressing an NOI in endosperm (preferably selectively expressing in endosperm), the method comprising expressing the NOI when it is operably linked to the promoter of the present invention.

The terms "selective" and "selectively" as used herein with respect to the present invention are synonymous respectively with the terms "specific" and "specifically". In this respect, selective or specific expression by the promoter of the present invention in the endosperm layer means that higher levels of expression occur in the endosperm relative to other tissue types or cells.

In some instances, the NOI is highly selectively expressed in the endosperm. In this respect, highly selective or specific expression by the promoter of the present invention in the endosperm layer means that expression occurs predominantly in the endosperm relative to other tissue types or cells and in some cases almost exclusively in the endosperm layer.

Preferably the transformed host/host cells is/are plant/plant cells.

The plant can be any suitable monocot plant (such as maize) or any suitable dicot plant (such as soya or guar).

Preferably the plant is an endospermous cereal or a legume.

In a preferred aspect, the plant is a member of the grass family—such as any one of wheat, maize, barley, oats, rye, or rice.

In an alternative preferred aspect, the plant is a legume—such as any one of guar or locus bean.

Hence, preferably, the transformed host is a transformed member of the taxonomic groups Gramineae (which may be known as Poaceae) or Leguminosae (which may be known as Fabaceae) or is a cell or tissue thereof.

Hence, preferably, the transformed plant is a transformed grass or a transformed legume.

Also, preferably, the transformed plant cell is a transformed grass cell or a transformed legume cell.

The present invention is advantageous for a number of reasons.

By way of example, the present invention is advantageous because desirable levels of the expression product of a NOI can be obtained. Here, the NOI expression product may be, for example, a desired compound of benefit to humans or animals, e.g. a desirable foodstuff or an enzyme having a beneficial effect, such as a foodstuff processing effect or even a pharmaceutical effect. Furthermore, that product may be easily retrievable.

Alternatively, the NOI expression product may affect metabolism within the host. In some cases, the NOI expression product may be a component that is essential for metabolism within the host. In these instances, it may not be important for the POI to be retrieved from the host. In some cases, it may be important that the POI is not retrieved from the host.

The present invention is also advantageous because it allows transformed plants or plant cells to express desirable levels of the product of expression of a NOI.

The present invention is also advantageous because it allows transformed plants or plant cells to express in selective tissues or cell types desirable levels of the expression product of a NOI.

The promoter of the present invention is further advantageous as it can provide good expression levels of a NOI under conditions of transient expression in plant cells.

In a preferred aspect, the promoter is linked to the sequence presented as SEQ ID No. 2, or a variant, homologue, derivative or fragment thereof. The term "linked" includes direct or indirect (such as with the provision of suitable spacer sequence(s)) linkages.

Preferably the sequence presented as SEQ ID No. 2, or a variant, homologue, derivative or fragment thereof is located in between the promoter of the present invention and the NOI.

In this respect, we have found that in some transformed hosts, such as transformed plants (such as transformed guar), expression levels of the NOI can be elevated. This is important if it is desirable to have such an elevated expression.

The promoter may be used in conjunction with one or more other expression elements—which may be alternatively called "functional elements". These additional expression elements may be linked to the promoter of the present invention. The term "linked" includes direct or indirect (such as with the provision of suitable spacer sequence(s)) linkages.

The additional expression element may enhance expression or inhibit undesirable expression.

The additional expression element may even be a promoter, wherein that promoter may be the same as or different to the promoter of the present invention, or even a part thereof.

The present invention also encompasses repeating units of promoters—such as tandem repeats that comprise at least two promoter elements—one of which will be the promoter of the present invention—such as three promoter elements.

Preferably the additional expression elements are located intermediate the promoter of the present invention and the NOI. Should it be desirable, the additional expression elements and the promoter of the present invention may be separated by suitable restriction sites.

In this respect, we have found that in some transformed hosts, such as transformed plants (such as transformed guar), expression levels of the NOI can be elevated. This is important if it is desirable to have such an elevated expression.

In one aspect, the NOI is an antisense nucleotide sequence.

In this respect, preferably the NOI is a sequence that is antisense to all or part of the gene encoding an epimerase, in particular a UDP galactose epimerase, more in particular a UDP galactose-4-epimerase (EC 5.1.3.3).

If the NOI is a sequence that is antisense to all or part of the gene encoding a UDP galactose epimerase—more in particular a UDP galactose-4-epimerase (EC 5.1.3.3)—then expression of that antisense sequence by the promoter of the present invention could affect the galactose units (such as causing a decrease thereof) on a galactomannan or other extracellular polysaccharides.

In an alternative aspect, the NOI is a sense nucleotide sequence.

Here, the NOI may be a sequence that constitutes all or part of the gene encoding a UDP galactose epimerase, more in particular a UDP galactose-4-epimerase (EC 5.1.3.3).

Promoter

Thus, the present invention relates to a novel regulatory sequence, namely a promoter—which we have called the RSus3 promoter.

The term "promoter" is used in the normal sense of the art, e.g. an RNA polymerase binding site.

The promoter may be the same as the naturally occurring form—for this aspect, preferably the promoter is not present in its natural environment. In addition, or in the alternative, the promoter is in an isolated and/or in a purified form. The promoter of the present invention can be a variant, homologue, fragment or derivative of the naturally occurring promoter. The promoter can be obtainable from or produced by any suitable source, whether natural or not, or it may be synthetic, semi-synthetic or recombinant.

A nucleotide sequence comprising the promoter of the present invention and other associated nucleotide sequences is schematically presented in FIG. 1 (which is not to scale).

In this respect, the promoter sequence SEQ ID No. 1 is shown as Box A. As can be seen, Box A comprises two units—which have been shown diagramatically as Box B and Box C. Box B corresponds to SEQ ID No. 6 and Box C corresponds to SEQ ID No. 4. SEQ ID No. 6 is the sequence up to the TATA box. SEQ ID No. 4 is the first part of an exon sequence.

In accordance with the present invention we have found that expression may still be achieved in some host cells with the promoter of the present invention in the absence of all or part of SEQ ID No. 4. In this respect, the promoter of the present invention would be represented as SEQ ID No. 6 and the comments concerning SEQ ID No. 1 would equally apply to SEQ ID No. 6.

FIG. 1 also shows Box D—which corresponds to SEQ ID No. 2. SEQ ID No. 2 is an intron sequence. In accordance with the present invention we have found that surprisingly expression can still be achieved with the promoter of the present invention in the absence of all or part of SEQ ID No. 2. Thus, in one embodiment of the present invention the promoter of the present invention is not used in conjunction with all or part of SEQ ID No. 2.

However, in some instances we have surprisingly found that SEQ ID No. 2 can elevate expression levels of an NOI and/or increase the selectivity of the expression. Hence, in an alternative preferred embodiment of the present invention the promoter of the present invention is used in conjunction with all or part of SEQ ID No. 2.

FIG. 1 also shows Box E—which corresponds to SEQ ID No. 5. SEQ ID No. 5 is the second part of the exon sequence associated with SEQ ID No. C. For some applications, the promoter sequence of the present invention is contained within a nucleotide sequence wherein SEQ ID No. 4 is fused to SEQ ID No. 5.

Thus, schematically, and by way of example, the promoter of the present invention may be represented as any one or more of: Box A; Box B with or without Box C; Box A with Box D; Box B—with or without Box C—with Box D; Box A with Box E; Box B—with or without Box C—with Box E; Box A with Box D and Box E; Box B—with or without Box C—with Box D and Box E.

It is to understood that: Box A represents SEQ ID No. 1 or a variant, homologue, fragment or derivative thereof, preferably, Box A represents SEQ ID No. 1; Box B represents SEQ ID No. 6 or a variant, homologue, fragment or derivative thereof, preferably, Box B represents SEQ ID No. 6; Box C represents SEQ ID No. 4 or a variant, homologue, fragment or derivative thereof, preferably, Box C represents SEQ ID No. 4; Box D represents SEQ ID No. 2 or a variant, homologue, fragment or derivative thereof, preferably, Box D represents SEQ ID No. 2; Box E represents SEQ ID No. 5 or a variant, homologue, fragment or derivative thereof, preferably, Box E represents SEQ ID No. 5.

In our analysis of the promoter of the present invention we have identified a number of interesting expression elements/functional elements which resemble consensus sequences or parts thereof.

These identified sequences are presented in Table 1 below.

TABLE 1

| Functional elements in the RSus3 promoter region | Positon | Position (-intron) | RSus3 sequence[1] | Consensus sequence | Reference (Consensus sequence) |
|---|---|---|---|---|---|
| Translation start site | +1 | +1 | CAATGG (SEQ ID No 7) | CAATGG (SEQ ID No 8) | [Joshi 1987] |
| Intron 1 (Acceptor splice site) | −27 | | TCCAG\|GC (SEQ ID No 9) | TGCAG\|GT (SEQ ID No 10) | [Simpson & Filipowicz 1996], consensus for monocots |
| Intron 1 (Donor splice site) | −892 | | AG\|GTAGAG (SEQ ID No 11) | AG\|GTAAGT (SEQ ID No 12) | |
| TATA box | −986 | −121 | TATAAATA (SEQ ID No 13) | TATATATA (SEQ ID No 14) | [Joshi 1987] |
| CAAT box | −999 | −134 | GCACATTT (SEQ ID No 15) | GGNCAATCT (SEQ ID No 16) | |
| GCN4 box | −1032 | −167 | GTGAGGCAG (SEQ ID No 17) | (G/A)TGA(G/C)TCA(T/G) (SEQ ID No 18) | [Muller & Knudsen 1993], cis-element involved in endosperm specificity |
| Endosperm boxes | −1072 | −207 | AGTAAAG (SEQ ID No 19) | TG(T/C/A)AA(G/A) (SEQ ID No 20) | [Marzabal et al. 1998], cis-element involved in endosperm specificity |
| | −1130 | −265 | TGCAAAC (SEQ ID No 21) | | |
| | −1349 | −484 | TGTCAAA (SEQ ID No 22) | | |
| Legumin boxes (RY repeats) | −1539 | −674 | CGTGCATG (SEQ ID No 23) | CATGCATG (SEQ ID No 24) | [Baumlein et al. 1992] cis-element involved in seed specificity |
| | −1586 | −721 | CATGTATG (SEQ ID No 25) | | |
| | −1624 | −759 | CATGCATA (SEQ ID No 26) | | |
| | −1707 | −842 | CATGCATGCATG (SEQ ID No 27) | | |
| | −2115 | −1250 | CATGCCTG (SEQ ID No 28) | | |
| | −2480 | −1615 | CAGGCATGCATC (SEQ ID No 29) | | |

We currently believe that at least one or more, such as all, of those identified sequences that are the same as or similar to the consensus sequences should be present in the promoter sequence of the present invention.

As indicated above, the promoter can additionally include or be used with features to ensure or to increase expression in a suitable host. For example, the features can be conserved regions such as a Pribnow Box or a TATA box.

The promoter may even contain or be used with other sequences to affect (such as to maintain, enhance, decrease) the levels of expression of the nucleotide sequence of the present invention. For example, suitable other sequences may include the Sh1-intron or an ADH intron. Other sequences may include inducible elements—such as temperature, chemical, light or stress inducible elements. Also, suitable elements to enhance transcription or translation may be present. An example of the latter element is the TMV 5' signal sequence (see Sleat Gene 217 [1987] 217–225; and Dawson Plant Mol. Biol. 23 [1993] 97).

The promoter of the present invention may be used in combination with one or more other expression elements or functional elements or regulatory elements.

The terms "expression elements", "functional elements" and "regulatory elements" include enhancers, expression regulation signals, secretion leader sequences, promoter consensus sequences, terminator sequences, and may even include other promoters.

The present invention also encompasses hybrid promoters that comprise at least a part of the promoter of the present invention and at least a part of another promoter.

Hybrid promoters may also be used to improve inducible regulation of the expression construct.

As indicated above, the present invention also encompasses tandem promoters wherein at least one of the promoters is the promoter of the present invention. If the other promoter is a promoter of the present invention or part thereof then that combination may be called a tandem repeat.

The other promoter may even be another promoter or part thereof. By way of example, the other promoter may be selected for its efficiency in directing the expression of the NOI in the desired expression host.

In one embodiment, a constitutive promoter may be selected to direct the expression of the NOI. Such an expression construct may provide additional advantages since it may circumvent the need to culture the expression hosts on a medium containing an inducing substrate. Examples of strong constitutive and/or inducible promoters which are preferred for use in, for example, fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the glaA gene), acetamidase (amdS) and glyceraldehyde-3-phosphate dehydrogenase (gpd) promoters. Examples of strong yeast promoters are those obtainable from the genes for alcohol dehydrogenase, 3-phosphoglycerate kinase and triosephosphate isomerase. Examples of strong bacterial promoters are the α-amylase and SP02 promoters as well as promoters from extracellular protease genes. Examples of strong plant promoters are the CaMV promoter and the SV40 35S promoter and the NOS promoter.

For some applications, preferably the promoter is stably incorporated within the transformed organism's genome.

The term "transformed" is synonymous with the term "transgenic".

In a preferred aspect, the promoter is linked to the sequence presented as SEQ ID No. 2, or a variant, homologue, derivative or fragment thereof.

Naturally Occurring

As used herein "naturally occurring" refers to the promoter sequence found in nature—i.e. the wild type promoter.

Isolated/Purified

As used herein, the terms "isolated" and "purified" refer to nucleic acid sequences, that are removed from their natural environment and isolated or separated from at least one other component with which they are naturally associated.

Biologically Active

As used herein "biologically active" refers to a promoter according to the present invention—such as a recombinant promoter—having a similar structural function (but not necessarily to the same degree), and/or similar regulatory function (but not necessarily to the same degree), and/or similar biochemical function (but not necessarily to the same degree) of the naturally occurring promoter. Specifically, a promoter of the present invention has the ability to express a NOI in endosperm, preferably selectively in endosperm.

Deletion

As used herein, a "deletion" is defined as a change in the nucleotide sequence in which one or more nucleotides are absent.

Insertion/Addition

As used herein, an "insertion" or "addition" is a change in the nucleotide sequence which has resulted in the addition of one or more nucleotides as compared to the naturally occurring promoter.

Substitution

As used herein, "substitution" results from the replacement of one or more nucleotides or by one or more different nucleotides.

Variant/Homologue

The terms "variant" or "homologue" with respect to the nucleotide sequence of the present invention are synonymous with allelic variations of the sequences.

In particular, the term "homology" as used herein may be equated with the term "identity". Here, sequence homology with respect to the nucleotide sequence of the present invention can be determined by a simple "eyeball" comparison (i.e. a strict comparison) of any one or more of the sequences with another sequence to see if that other sequence has at least 75% identity to the sequence(s). Relative sequence homology (i.e. sequence identity) can also be determined by commercially available computer programs that can calculate % homology between two or more sequences. A typical example of such a computer program is CLUSTAL.

Sequence homology (or identity) may even be determined using any suitable homology algorithm, using for example default parameters. Advantageously, the BLAST algorithm is employed, with parameters set to default values. The BLAST algorithm is described in detail at http://www.ncbi.nih.gov/BLAST/blast_help.html, which is incorporated herein by reference. The search parameters are defined as follows, and are advantageously set to the defined default parameters.

Advantageously, "substantial homology" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (see http://www.ncbi.nih.gov/BLAST/blast_help.html) with a few enhancements. The BLAST programs were tailored for sequence similarity searching, for example to identify homologues to a query sequence. The programs are not generally useful for motif-style searching. For a discussion of basic issues in similarity searching of sequence databases, see Altschul et al (1994) Nature Genetics 6:119–129.

The five BLAST programs available at http://www.ncbi.nim.nih.gov perform the following tasks:
- blastp compares an amino acid query sequence against a protein sequence database;
- blastn compares a nucleotide query sequence against a nucleotide sequence database;
- blastx compares the six-frame conceptual translation products of a nucleotide query sequence (both strands) against a protein sequence database;
- tblastn compares a protein query sequence against a nucleotide sequence database dynamically translated in all six reading frames (both strands).
- tblastx compares the six-frame translations of a nucleotide query sequence against the six-frame translations of a nucleotide sequence database.

BLAST uses the following search parameters:

HISTOGRAM Display a histogram of scores for each search; default is yes. (See parameter H in the BLAST Manual).

DESCRIPTIONS Restricts the number of short descriptions of matching sequences reported to the number specified; default limit is 100 descriptions. (See parameter V in the manual page). See also EXPECT and CUTOFF.

ALIGNMENTS Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

EXPECT The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

MATRIX Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND Restrict a TBLASTN search to just the top or bottom strand of the database sequences; or restrict a BLASTN, BLASTX or TBLASTX search to just reading frames on the top or bottom strand of the query sequence.

FILTER Mask off segments of the query sequence that have low compositional complexity, as determined by the SEG program of Wootton & Federhen (1993) Computers and Chemistry 17:149–163, or segments consisting of short-periodicity internal repeats, as determined by the XNU program of Clayerie & States (1993) Computers and Chemistry 17:191–201, or, for BLASTN, by the DUST program of Tatusov and Lipman (see http://www.ncbi.nlm.nih.gov). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi Causes NCBI gi identifiers to be shown in the output, in addition to the accession and/or locus name.

Preferably, sequence comparisons are conducted using the simple BLAST search algorithm provided at http://www.ncbi.nlm.nih.gov/BLAST.

Other computer program methods to determine identify and similarity between the two sequences include but are not limited to the GCG program package (Devereux et al 1984 Nucleic Acids Research 12: 387 and FASTA (Atschul et al 1990 J Molec Biol 403–410).

Should Gap Penalties be used when determining sequence identity, then preferably the following parameters are used:

| FOR BLAST | |
|---|---|
| GAP OPEN | 0 |
| GAP EXTENSION | 0 |
| FOR CLUSTAL | DNA |
| WORD SIZE | 2 |
| GAP PENALTY | 10 |
| GAP EXTENSION | 0.1 |

Most preferably, sequence comparisons are conducted using DNASIS™.

As used herein, the terms "variant", "homologue", "fragment" and "derivative" embrace allelic variations of the sequences.

The term "variant" also encompasses sequences that are complementary to sequences that are capable of hydridising to the nucleotide sequences presented herein.

Hybridisation

The term "hybridisation" (sometimes written as "hybridization") as used herein shall include "the process by which a strand of nucleic acid joins with a complementary strand through base pairing" (Coombs J (1994) Dictionary of Biotechnology, Stockton Press, New York N.Y.) as well as the process of amplification as carried out in polymerase chain reaction (PCR) technologies as described in Dieffenbach C W and G S Dveksler (1995, PCR Primer, a Laboratory Manual, Cold Spring Harbor Press, Plainview N.Y.).

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Stringency of hybridisation refers to conditions under which polynucleic acids hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na+ at 65–68° C.

Maximum stringency typically occurs at about Tm-5° C. (5° C. below the Tm of the probe).

High stringency typically occurs at about 5° C. to 10° C. below the Tm of the probe. High stringency conditions can be provided, for example, by hybridisation in an aqueous solution containing 6×SSC, 5× Denhardt's, 1% SDS (sodium dodecyl sulphate), 0.1 Na+ pyrophosphate and 0.1 mg/ml denatured salmon sperm DNA as non specific competitor. Following hybridisation, high stringency washing may be done in several steps, with a final wash (about 30 min) at the hybridisation temperature in 0.2–0.1×SSC, 0.1% SDS.

Moderate, or intermediate, stringency typically occurs at about 10° C. to 20° C. below the Tm of the probe.

Low stringency typically occurs at about 20° C. to 25° C. below the Tm of the probe.

As will be understood by those of skill in the art, a maximum stringency hybridization can be used to identify or detect identical polynucleotide sequences, while an intermediate (or low) stringency hybridization can be used to identify or detect similar or related polynucleotide sequences.

Moderate stringency refers to conditions equivalent to hybridisation in the above described solution but at about 60–62° C. In that case the final wash is performed at the hybridisation temperature in 1×SSC, 0.1% SDS.

Low stringency refers to conditions equivalent to hybridisation in the above described solution at about 50–52° C. In that case, the final wash is performed at the hybridisation temperature in 2× SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Nucleotide Sequence

The term "nucleotide sequence" as used herein refers to an oligonucleotide sequence or polynucleotide sequence, and variants, homologues, fragments and derivatives thereof (such as portions thereof. The nucleotide sequence may be of genomic or synthetic or recombinant origin which may be double-stranded or single-stranded whether representing the sense or antisense strand.

Preferably, the term "nucleotide sequence" means DNA.

In a preferred embodiment, the nucleotide sequence per se of the present invention does not cover the native nucleotide sequence according to the present invention in its natural environment when it is linked to its naturally associated sequence(s) that is/are also in its/their natural environment. For ease of reference, we shall call this preferred embodiment the "non-native nucleotide sequence".

Typically, the nucleotide sequence of the present invention is prepared using recombinant DNA techniques (i.e. recombinant DNA). However, in an alternative embodiment of the invention, the nucleotide sequence could be synthesized, in whole or in part, using chemical methods well known in the art (see Caruthers M H et al (1980) Nuc Acids Res Symp Ser 215–23, Horn T et al (1980) Nuc Acids Res Symp Ser 225–232).

The present invention also encompasses nucleotide sequences that are complementary to the sequences presented herein, or any derivative, fragment or derivative thereof. If the sequence is complementary to a fragment thereof then that sequence can be used as a probe to identify similar sequences in other organisms etc.

The present invention also encompasses nucleotide sequences that are capable of hybridising to the sequences presented herein, or any derivative, fragment or derivative thereof.

The present invention also encompasses nucleotide sequences that are capable of hybridising to the sequences that are complementary to the sequences presented herein, or any derivative, fragment or derivative thereof.

The term "variant" also encompasses sequences that are complementary to sequences that are capable of hydridising to the nucleotide sequences presented herein.

Preferably, the term "variant" encompasses sequences that are complementary to sequences that are capable of hydridising under stringent conditions (e.g. 65° C. and 0.1×SSC {1×SSC=0.15 M NaCl, 0.015 $Na_3$ citrate pH 7.0)) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Also included within the scope of the present invention are polynucleotide sequences that are capable of hybridizing to the nucleotide sequences presented herein under conditions of intermediate to maximal stringency.

In a preferred aspect, the present invention covers nucleotide sequences that can hybridise to the nucleotide sequence of the present invention under stringent conditions (e.g. 65° C. and 0.1×SSC).

Advantageously, the invention provides nucleic acid sequences which are capable of hybridising, under stringent conditions, to a fragment of SEQ. ID. No. 1. Preferably, the fragment is between 15 and 50 bases in length. Advantageously, it is about 25 bases in length.

By knowledge of the nucleic acid sequences set out herein it is possible to devise partial and full-length nucleic acid sequences such as cDNA and/or genomic clones. Nucleic acid sequences obtained by PCR—such as fragments of the full length sequence, preferably fragments having unique sequences—may then be used to obtain same or similar sequences using hybridization library screening techniques. The fragments may be from 10 to 100 nucleotides long. Preferably, the fragments may be from 15 to 90 nucleotides long. More preferably, the fragments may be from 20 to 80 nucleotides long.

By way of example, a PCR clone may be labelled with radioactive atoms and used to screen a genomic library from other species, preferably other plant species. Hybridization conditions will typically be conditions of medium to high stringency (for example 0.03M sodium chloride and 0.03M sodium citrate at from about 50° C. to about 60° C.).

Degenerate nucleic acid probes encoding all or part of the amino acid sequence may also be used to probe cDNA and/or genomic libraries from other species, preferably other plant species or fungal species. However, it is preferred to carry out PCR techniques initially to obtain a single sequence for use in further screening procedures.

Polynucleotide sequences of the present invention obtained using the techniques described above may be used to obtain further homologous sequences and variants using the techniques described above.

Thus, polynucleotides of the present invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the present invention as used herein.

Polynucleotides or primers of the present invention may carry a revealing label. Suitable labels include radioisotopes such as $^{32}P$ or $^{35}S$, enzyme labels, or other labels such as biotin or digoxigenin. The DIG™ system (Boehringer Mannheim) is useful as it offers a very attractive non-radioactive system. The DIG system is based on the steroid hapten digoxigenin, which occurs exclusively in Digitalis plants and thus avoids endogenous background problems as in the case of other haptens, such as biotin} Such labels may be added to polynucleotides or primers of the present invention and may be detected using by techniques known per se.

Polynucleotides such as a DNA polynucleotide and primers according to the present invention may be produced recombinantly, synthetically, or by any means available to those of skill in the art. They may also be cloned by standard techniques. In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR cloning techniques. This will involve making a pair of primers (e.g. of about 15–30 nucleotides) to a region of the nucleotide sequence which it is desired to clone, bringing the primers into contact with mRNA or cDNA obtained from a fungal, plant or prokaryotic cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

The nucleotide sequence of the present invention may be engineered in order to alter its activity for a number of reasons, including but not limited to, alterations which modify the processing and/or expression. For example, mutations may be introduced using techniques which are well known in the art, e.g., site-directed mutagenesis to insert new restriction sites, to alter glycosylation patterns or to change codon preference. By way of further example, the nucleotide sequence of the present invention may also be modified to optimise expression in a particular host cell—such as the inclusion of additional promoter(s) or parts thereof, such as the provision of tandem repeats, and/or the provision of other expression elements such as the intron sequence. Other sequence changes may be desired in order to introduce restriction enzyme recognition sites.

Variant, Homologue and Fragment of the Promoter Nucleotide Sequence

The terms "variant", "homologue" or "fragment" in relation to the nucleotide sequence of the present invention include any substitution of, variation of, modification of, replacement of, deletion of or addition of one (or more) nucleic acid from or to the sequence providing the resultant nucleotide sequence has the ability to act as a promoter, preferably being at least as biologically active as the promoter having the sequence shown as SEQ ID No. 1. In particular, the term "homologue" covers homology with respect to structure and/or function providing the resultant nucleotide sequence has the ability to act as a promoter. With respect to sequence homology, preferably there is at least 75%, more preferably at least 85%, more preferably at least 90% homology to the sequence shown as SEQ ID No. 1. More preferably there is at least 95%, more preferably at least 98%, homology to the sequence shown as SEQ ID No. 1.

The present invention also relates to DNA segments comprising the DNA sequence of SEQ ID No. 1 or allelic variations of such sequences. These segments are capable of acting as a regulatory region/unit.

Variant, Homologue and Fragment of Nucleotide Sequence SEQ ID No. 2

The terms "variant", "homologue" or "fragment" in relation to the nucleotide sequence of the present invention include any substitution of, variation of, modification of, replacement of, deletion of or addition of one (or more) nucleic acid from or to the sequence providing the resultant nucleotide sequence has the ability to increase expression levels, preferably being at least as biologically active as the sequence shown as SEQ ID No. 2. In particular, the term "homologue" covers homology with respect to structure and/or function providing the resultant nucleotide sequence has the ability to increase expression levels. With respect to sequence homology, preferably there is at least 75%, more preferably at least 85%, more preferably at least 90% homology to the sequence shown as SEQ ID No. 2. More preferably there is at least 95%, more preferably at least 98%, homology to the sequence shown as SEQ ID No. 2.

The present invention also relates to DNA segments comprising the DNA sequence of SEQ ID No. 2 or allelic variations of such sequences. These segments are capable of increasing expression levels.

Variant, Homologue and Fragment of any One or More of the Identified Nucleotide Sequences in Table 1

The terms "variant", "homologue" or "fragment" in relation to any one of the nucleotide sequences presented in Table 1 include any substitution of, variation of, modification of, replacement of, deletion of or addition of one (or more) nucleic acid from or to the sequence providing the resultant nucleotide sequence has the ability to influence expression. In particular, the term "homologue" covers homology with respect to structure and/or function providing the resultant nucleotide sequence has the ability to influence expression. With respect to sequence homology, preferably there is at least 75%, more preferably at least 85%, more preferably at least 90% homology to the respective sequence shown in Table 1. More preferably there is at least 95%, more preferably at least 98%, homology to the respective sequence shown in Table 1.

NOI/POI

In a preferred aspect, the present invention relates to the use of the promoter of the present invention to express one or more suitable NOIs.

Thus, in a preferred aspect, the promoter is operably linked to a NOI.

The term "operably linked" refers to a relationship—such as in a suitable juxtaposition—wherein the components described are in a relationship permitting them to function in their intended manner. A regulatory sequence "operably linked" to a NOI is ligated in such a way that expression of the coding sequence is achieved under condition compatible with the control sequences.

The NOI can encode for a POI.

The NOI can be any suitable sequence encoding a polypeptide of interest, other than the complete natural sequence normally associated with the promoter of the present invention when the NOI is operably linked to the promoter in their natural environment.

Preferably, the NOI does not include all of the nucleotide sequence naturally associated with the wild type promoter of the present invention.

The NOI can be any nucleotide sequence that is either foreign (heterologous) or natural (homologous) to the organism in question—which may be a filamentous fungus or a plant.

Typically, the POI may be any suitable prokaryotic or eukaryotic heterologous or homologous peptide or protein of interest.

For some applications, the POI may be secreted and/or retrieved.

For some applications, it is important that the POI is secreted and/or retrieved.

For some applications, the POI may not secreted and/or retrieved.

For some applications, it is important that the POI is not secreted and/or retrieved.

The NOI may even be a sequence which is capable of expressing a nucleic acid, for example a regulatory RNA such as an antisense RNA or a ribozyme, an mRNA, or a tRNA or rRNA capable of regulating the metabolism of an organism.

The NOI may also be a homologous nucleotide sequence which has been mutated, such as by insertion, addition, deletion or alteration, such that it is no longer identical with the natural homologous nucleotide sequence.

The POI can be a single-chain polypeptide molecule as well as a multiple-polypeptide complex where individual constituent polypeptides are linked by covalent or non-covalent means. Here, the term "polypeptide" includes peptides of two or more amino acids in length, typically having more than 5, or more than 10 or more than 20 amino acids.

Typical examples of a NOI include sequences coding for proteins and enzymes that modify metabolic and catabolic processes. The heterologous nucleotide sequence may code for an agent for introducing or increasing pathogen resistance. The heterologous nucleotide sequence may be an antisense construct for modifying the expression of natural transcripts present in the relevant tissues.

The heterologous nucleotide sequence may be a protein giving nutritional value to a food or crop. Typical examples include plant proteins that can aid human or animal digestion, inhibit the formation of anti-nutritive factors and those plant proteins that have a more desirable amino acid composition (e.g. a higher lysine content than a non-transgenic plant).

Non-limiting examples of POIs include, for example, proteins involved in the regulation of cell division, for example growth factors including neurotrophic growth factors, cytokines (such as $\alpha$-, $\beta$- or $\gamma$-interferon, interleukins including IL-1, IL-2, tumour necrosis factor, or insulin-like growth factors I or II), protein kinases (such as MAP kinase), protein phosphatases and cellular receptors for any of the above.

The POI may also be an enzyme involved in cellular metabolic pathways, for example enzymes involved in carbohydrate biosynthesis or degradation, amino acid biosynthesis or degradation (such as tyrosine hydroxylase), purine or pyrimidine biosynthesis or degradation, and the biosynthesis or degradation of neurotransmitters, such as dopamine, or a protein involved in the regulation of such pathways, for example protein kinases and phosphatases.

The POI may also be effective in the post-harvest processing of plants—e.g. in the brewing or baking processes.

The POI may also be a transcription factors or proteins involved in their regulation, for example pocket proteins of the Rb family such as Rb or p107, membrane proteins, structural proteins or heat shock proteins such as hsp70.

The NOI may code for an intron of a particular nucleotide sequence, wherein the intron can be in sense or antisense orientation.

Non-limiting examples of POIs include: proteins or enzymes involved in starch metabolism, proteins or enzymes involved in glycogen metabolism, acetyl esterases, aminopeptidases, amylases, arabinases, arabinofuranosidases, carboxypeptidases, catalases, cellulases, chitinases, chymosin, cutinase, deoxyribonucleases, epimerases, esterases, $\alpha$-galactosidases, $\beta$-galactosidases, $\alpha$-glucanases, glucan lysases, endo-$\beta$-glucanases, glucoamylases, glucose oxidases, $\alpha$-glucosidases, $\beta$-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, thaumatin, transferases, transport proteins, transglutaminases, xylanases, or combinations thereof. The NOI may even be an antisense sequence for any of those sequences.

The NOI can be the nucleotide sequence coding for the exo-amylase enzyme which is the subject of PCT patent application PCT/IB99/00649 (incorporated herein by reference).

The NOI can be the nucleotide sequence coding for the xylanase enzymes and mutants thereof which are the subject of UK patent application GB 99078057 (incorporated herein by reference).

The NOI can be the nucleotide sequence coding for the arabinofuranosidase enzyme which is the subject of PCT patent application PCT/EP96/01009 (incorporated herein by reference).

The NOI can be any of the nucleotide sequences coding for the ADP-glucose pyrophosphorylase enzymes which are the subject of PCT patent application PCT/EP94/01082 (incorporated herein by reference).

The NOI can be any of the nucleotide sequences coding for the α-glucan lyase enzyme which are described in PCT patent application PCT/EP94/03397 (incorporated herein by reference).

The NOI can be any of the sequences coding for *T. lanuginosus* amylase, as described in PCT patent application PCT/EP95/02607, incorporated herein by reference.

The NOI can be any of the nucleotide sequences coding for the glucanase enzyme which are described in PCT patent application PCT/EP96/01008 (incorporated herein by reference).

The NOI can be any of the nucleotide sequences coding for the UDP-galactose epimerase enzyme, as well as antisense sequences therefor,—such as those which are described in PCT patent application WO-A-98/54335 (incorporated herein by reference).

The NOI can be hox from the red algae Chondrus crispus or lipA from *Aspergillus niger*.

The POI can be a PME as disclosed in WO-A-97/03574 or the PME disclosed in either WO-A-94/25575 or WO-A-97/31102 as well as variants, derivatives or homologues of the sequences disclosed in those patent applications.

The POI may even be a fusion protein, for example to aid in extraction and purification.

Examples of fusion protein partners include the maltose binding protein, glutathione-S-transferase (GST), 6×His, GAL4 (DNA binding and/or transcriptional activation domains) and β-galactosidase. It may also be convenient to include a proteolytic cleavage site between the fusion components.

The POI may even be fused to a secretion sequence. Examples of secretion leader sequences are those originating from the amyloglucosidase gene, the α-factor gene, the α-amylase gene, the lipase A gene, the xylanase A gene.

Other sequences can also facilitate secretion or increase the yield of secreted POI. Such sequences could code for chaperone proteins as for example the product of *Aspergillus niger* cyp B gene described in UK patent application 9821198.0.

The NOI may be engineered in order to alter their activity for a number of reasons, including but not limited to, alterations which modify the processing and/or expression of the expression product thereof. For example, mutations may be introduced using techniques which are well known in the art, e.g., site-directed mutagenesis to insert new restriction sites, to alter glycosylation patterns or to change codon preference. By way of further example, the NOI may also be modified to optimise expression in a particular host cell. Other sequence changes may be desired in order to introduce restriction enzyme recognition sites.

The NOI may include within it synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the NOI may be modified by any method available in the art. Such modifications may be carried out in to enhance the in vivo activity or life span of the NOI.

The NOI may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

Constructs

The term "construct"—which is synonymous with terms such as "conjugate", "cassette" and "hybrid"—includes the nucleotide sequence according to the present invention directly or indirectly attached to a NOI. An example of an indirect attachment is the provision of a suitable spacer group such as an intron sequence, such as the Sh1-intron or the ADH intron, intermediate the promoter and the NOI. The same is true for the term "fused" in relation to the present invention which includes direct or indirect attachment. In each case, the terms do not cover the natural combination of the wild type gene promoter and its associated nucleotide sequence when they are both in their natural environment.

The construct may even contain or express a marker which allows for the selection of the genetic construct in, for example, a plant cell into which it has been transferred.

The selectable marker means may reside on an additional vector or may be included in the nucleic acid molecule which contains the expression system. The nature of the selectable marker means will depend on the nature of the host and the culture conditions. The most suitable selection systems for industrial micro-organisms are those formed by the group of selection markers which do not require a mutation in the host organism.

U.S. Pat. No. 5,358,864 provides a short list of suitable selectable marker genes that may be used in the present invention—examples of which include fungal selection markers such as those that are the genes for acetamidase (amdS), ATP synthetase, subunit 9 (oliC) and benomyl resistance (benA).

Examples of non-fungal selection markers are the bacterial G418 resistance gene (this may also be used in yeast, but not in fungi), the ampicillin resistance gene (*E. coli*), the neomycin resistance gene (*Bacillus*) and the *E. coli* uidA gene, coding for β-glucuronidase (GUS).

In certain aspects of the present invention, use of the ble marker—which confers resistance to phleomycin/bleomycin/zeocin—may be preferred. However, other selection markers, known in the art, could be used. Examples of auxotrophic markers are pyrG selecting for uridine prototrophs, argB selecting for arginine prototrophs, niaD selecting for nitrate prototrophs, trpC selecting for tryptophan prototrophs, amdS selecting for increased utilisation of acetamide as sole nitrogen source. Dominant resistance markers could be chosen from oliC3 conferring resistance to oligomycin, hph conferring resistance to hygromycin B, bar conferring resistance to bialaphos or NPTII conferring resistance to G418.

The construct may even contain or express a marker which allows for the selection of the genetic construct in, for example, a bacterium, preferably of the genus *Bacillus*, such as *Bacillus subtilis*, or plants, such as potatoes, sugar beet etc., into which it has been transferred.

The construct may even contain or express a marker which allows for the selection of the genetic construct in, for example, a plant. Various markers exist which may be used, such as for example those encoding mannose 6-phosphate isomerase, glucosamine 6-phosphate deaminase/ketoisomerase, xylose isomerase, or those markers that provide for antibiotic resistance—e.g. resistance to G418, hygromycin, bleomycin, kanamycin and gentamycin.

Vectors

The term "vector" includes expression vectors, replicable vectors, transformation vectors and shuttle vectors, including vector combinations thereof.

The term "expression vector" means a construct capable of in vivo or in vitro expression.

Preferably the expression vector is incorporated in the genome of the organism. The term "incorporated" preferably covers stable incorporation into the genome.

Preferably, the vector of the present invention comprises a construct according to the present invention. Alternatively expressed, preferably the promoter of the invention is present in a vector and wherein the promoter is operably linked to a NOI such that the promoter is capable of providing for the expression of the coding sequence by a suitable host organism, i.e. the vector is an expression vector.

The term "transformation vector" means a construct capable of being transferred from one entity to another entity—which may be of the species or may be of a different species. If the construct is capable of being transferred from one species to another—such as from an *E. coli* plasmid to a bacterium, such as of the genus *Bacillus*, then the transformation vector is sometimes called a "shuttle vector". It may even be a construct capable of being transferred from an *E. coli* plasmid to an *Agrobacterium* to a plant.

The vectors of the present invention may be transformed into a suitable host cell to provide for expression of a POI.

Thus, in a further aspect the invention provides a process for preparing a POI invention which comprises cultivating a host cell transformed or transfected with an expression vector under conditions to provide for expression by the promoter of the present invention of a NOI encoding the POI, and optionally recovering the expressed POI.

Typically, the nucleotide sequences of the invention may be incorporated into a recombinant replicable vector. The vector may be used to replicate the nucleic acid in a compatible host organism.

Thus, in a further embodiment, the invention provides a method of introducing a nucleotide sequence of the invention into a replicable vector, introducing the vector into a compatible host organism, and growing the host organism under conditions which bring about expression of a NOI by the promoter of the present invention. The POI may then be recovered from the host organism. Suitable host organisms include plants or plant cells.

The NOI may be incorporated into a replicable vector, for example a cloning or expression vector, which comprises a promoter of the present invention. The vector may be used to replicate the NOI in a compatible host cell.

Thus, in a further embodiment, the invention provides a method of making NOIs by introducing a NOI into a replicable vector which comprises the promoter of the present invention, introducing the vector into a compatible host cell, and growing the host cell under conditions which bring about replication of the vector. The vector may be recovered from the host cell.

The vectors may be for example, plasmid, virus or phage vectors. In addition to the promoter of the present invention, the vectors may be provided with any one or more of an origin of replication, a NOI operably linked to the promoter for the expression of the NOI, and a regulator of the promoter.

Vectors may be used, for example, to transfect or transform a host organism either in vitro or in vivo.

Such vectors may be transformed or transfected into a suitable host organism to provide for expression of a protein of the invention. This process may comprise culturing a host organism transformed with an expression vector as described above under conditions to provide for expression by the vector of a coding sequence encoding the protein, and optionally recovering the expressed protein.

Vectors of the invention may be introduced into host organisms for the purpose of replicating the vectors/nucleotide sequences and/or expressing the NOI. In one preferred aspect, the host organism is a plant cell.

Vectors of the present invention may introduced into suitable host organisms using a variety of techniques known in the art, such as transfection, transformation and electroporation. Another technique is the protoplast transformation method (Winer et al., Microbiology, 1985, 468, American Society for Microbiology).

Vectors may be used in vitro, for example for the production of RNA or used to transfect or transform a host cell.

Tissue

The term "tissue" as used herein includes tissue per se and organ.

Host Cells

The term "host cell"—in relation to the present invention includes any cell that could comprise the promoter of the present invention and/or products obtained therefrom, wherein the promoter can allow expression of a NOI when present in the host cell.

Thus, a further embodiment of the present invention provides host cells transformed or transfected with a promoter of the present invention. Preferably the promoter is carried in a vector for the replication and expression of NOIs. The cells will be chosen to be compatible with the said vector and may for example be prokaryotic (for example bacterial), fungal, yeast or plant cells.

Preferably, the host cell is a plant cell.

The gram-negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the NOI encoding the POI, and/or the desirability for further processing of the expressed protein, eukaryotic hosts such as yeasts or fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species. By way of example, typical expression hosts may be selected from *Pichia pastoris, Hansenula polymorpha, Aspergillus niger, Aspergillus niger* var. *tubigenis, Aspergillus niger* var. *awamori, Aspergillus aculeatis, Aspergillus nidulans, Aspergillus oryzae, Trichoderma reesei, Bacillus subtilis, Bacillus licheniformis, Bacillus amyloliquefaciens, Kluyveromyces lactis* and *Saccharomyces cerevisiae*.

The use of suitable host cells—such as yeast, fungal and plant host cells—may provide for post-translational modifications (e.g. myristolation, glycosylation, truncation, lapidation and tyrosine, serine or threonine phosphorylation) as may be needed to confer optimal biological activity on recombinant expression products of the present invention.

Thus, the present invention also provides a method of transforming a host cell with a nucleotide sequence shown as SEQ ID No. 1 or a derivative, homologue, variant or fragment thereof.

Host cells transformed with a promoter according to the present invention operably linked to a NOI may be cultured under conditions suitable for the expression and recovery of the POI from cell culture. The POI may be secreted or may be contained intracellularly depending on the sequence and/or the vector used. As will be understood by those of skill in the art, expression vectors containing a promoter according to the present invention operably linked to a NOI can be designed with signal sequences which direct secretion of the NOI/POI through a particular prokaryotic or eukaryotic cell membrane. Other recombinant constructions may join the NOI to a nucleotide sequence encoding a polypeptide domain which will facilitate purification of soluble proteins (Kroll D J et al (1993) DNA Cell Biol 12:441–53).

Organism

The term "organism" in relation to the present invention includes any organism that could comprise the nucleotide sequence of the present invention, wherein the promoter can allow expression of a NOI when present in the organism. Examples of organisms may include a fungus, yeast or a plant.

The term "transgenic organism" in relation to the present invention includes any organism that comprises the nucleotide sequence of the present invention, wherein the promoter can allow expression of a NOI within the organism. Preferably the nucleotide sequence is incorporated in the genome of the organism.

The term "transgenic organism" does not cover the native nucleotide sequence according to the present invention in its natural environment when it is operably linked to its associated coding sequence which is also in its natural environment.

Therefore, the transgenic organism of the present invention includes an organism comprising any one of, or combinations of, the nucleotide sequence of the present invention, constructs according to the present invention (including combinations thereof), vectors according to the present invention, plasmids according to the present invention, cells according to the present invention, tissues according to the present invention or the products thereof. The transformed cell or organism could prepare acceptable quantities of the POI. In some instances, the POI may be easily retrievable from, the cell or organism.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the NOI may need to be suitably modified before transformation—such as by removal of introns.

Transformed Fungus

A host organism may be a fungus—such as a mold. Examples of suitable such hosts include any member belonging to the genera *Thermomyces, Acremonium, Aspergillus, Penicillium, Mucor, Neurospora, Trichoderma* and the like—such as *Thermomyces lanuginosis, Acremonium chrysogenum, Aspergillus niger, Aspergillus oryzae, Aspergillus awamori*, Penicillinum chrysogenem, *Mucor javanious, Neurospora crassa, Trichoderma* viridae and the like.

In one embodiment, the host organism may be a filamentous fungus.

For almost a century, filamentous fungi have been widely used in many types of industry for the production of organic compounds and enzymes. For example, traditional Japanese koji and soy fermentations have used *Aspergillus* sp. Also, in this century *Aspergillus niger* has been used for production of organic acids particular citric acid and for production of various enzymes for use in industry.

There are two major reasons why filamentous fungi have been so widely used in industry. First filamentous fungi can produce high amounts of extracellular products, for example enzymes and organic compounds such as antibiotics or organic acids. Second filamentous fungi can grow on low cost substrates such as grains, bran, beet pulp etc. The same reasons have made filamentous fungi attractive organisms as hosts for heterologous expression according to the present invention.

In order to prepare the transgenic *Aspergillus*, expression constructs are prepared by inserting the nucleotide sequence according to the present invention (and optionally the NOI) into a construct designed for expression in filamentous fungi.

Several types of constructs used for heterologous expression have been developed. These constructs preferably contain one or more of: a signal sequence which directs the POI to be secreted, typically being of fungal origin, and a terminator (typically being active in fungi) which ends the expression system.

Another type of expression system has been developed in fungi where the nucleotide sequence according to the present invention (and optionally the NOI) can be fused to a smaller or a larger part of a fungal gene encoding a stable protein. This can stabilise the POI. In such a system a cleavage site, recognised by a specific protease, can be introduced between the fungal protein and the POI, so the produced fusion protein can be cleaved at this position by the specific protease thus liberating the POI. By way of example, one can introduce a site which is recognised by a KEX-2 like peptidase found in at least some Aspergilli. Such a fusion leads to cleavage in vivo resulting in production of the expressed product and not a larger fusion protein.

Heterologous expression in *Aspergillus* has been reported for several genes coding for bacterial, fungal, vertebrate and plant proteins. The proteins can be deposited intracellularly if the nucleotide sequence according to the present invention (or even the NOI) is not fused to a signal sequence. Such proteins will accumulate in the cytoplasm and will usually not be glycosylated which can be an advantage for some bacterial proteins. If the nucleotide sequence according to the present invention (or even the NOI) is equipped with a signal sequence the protein will accumulate extracellularly.

With regard to product stability and host strain modifications, some heterologous proteins are not very stable when they are secreted into the culture fluid of fungi. Most fungi produce several extracellular proteases which degrade heterologous proteins. To avoid this problem special fungal strains with reduced protease production have been used as host for heterologous production.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, Methods Enzymol (1971) 17A:79–143. Standard procedures are generally used for the maintenance of strains and the preparation of conidia. Mycelia are typically grown in liquid cultures for about 14 hours (25° C.), as described in Lambowitz et al., J Cell Biol (1979) 82:17–31. Host strains can generally be grown in either Vogel's or Fries minimal medium supplemented with the appropriate nutrient(s), such as, for example, any one or more of: his, arg, phe, tyr, trp, p-aminobenzoic acid, and inositol.

Further teachings on transforming filamentous fungi are reviewed in U.S. Pat. No. 5,674,707 which states that once a construct has been obtained, it can be introduced either in linear form or in plasmid form, e.g., in a pUC-based or other vector, into a selected filamentous fungal host using a technique such as DNA-mediated transformation, electroporation, particle gun bombardment, protoplast fusion and the like. In addition, Ballance 1991 (ibid) states that transformation protocols for preparing transformed fungi are based on preparation of protoplasts and introduction of DNA into the protoplasts using PEG and $Ca^{2+}$ ions. The transformed protoplasts then regenerate and the transformed fungi are selected using various selective markers.

To allow for selection of the resulting transformants, the transformation typically also involves a selectable gene marker which is introduced with the expression cassette, either on the same vector or by co-transformation, into a host strain in which the gene marker is selectable. Various marker/host systems are available, including the pyrG, argB and niaD genes for use with auxotrophic strains of *Aspergillus nidulans*; pyrG and argB genes for *Aspergillus oryzae* auxotrophs; pyrG, trpC and niaD genes for *Penicillium chrysogenum* auxotrophs; and the argB gene for *Trichoderma reesei* auxotrophs. Dominant selectable markers including amdS, oliC, hyg and phleo are also now available for use with such filamentous fungi as *A. niger, A. oryzae, A. ficuum, P. chrysogenum, Cephalosporium acremonium, Cochliobolus heterostrophus, Glomerella cingulata, Fulvia fulva* and *Leptosphaeria maculans* (for a review see Ward in Modern Microbial Genetics, 1991, Wiley-Liss, Inc., at pages 455–495). A commonly used transformation marker is the amdS gene of *A. nidulans* which in high copy number allows the fungus to grow with acrylamide as the sole nitrogen source.

For the transformation of filamentous fungi, several transformation protocols have been developed for many filamentous. Among the markers used for transformation are a number of auxotrophic markers such as argB, trpc, niaD and pyrG, antibiotic resistance markers such as benomyl resistance, hygromycin resistance and phleomycin resistance.

In one aspect, the host organism can be of the genus *Aspergillus*, such as *Aspergillus niger*.

A transgenic *Aspergillus* according to the present invention can also be prepared by following the teachings of Rambosek, J. and Leach, J. 1987 (Recombinant DNA in filamentous fungi: Progress and Prospects. CRC Crit. Rev. Biotechnol. 6:357–393), Davis R. W. 1994 (Heterologous gene expression and protein secretion in *Aspergillus*. In: Martinelli S. D., Kinghorn J. R. (Editors) *Aspergillus*: 50 years on. Progress in industrial microbiology vol 29. Elsevier Amsterdam 1994. pp 525–560), Ballance, D. J. 1991 (Transformation systems for Filamentous Fungi and an Overview of Fungal Gene structure. In: Leong, S. A., Berka R. M. (Editors) Molecular Industrial Mycology. Systems and Applications for Filamentous Fungi. Marcel Dekker Inc. New York 1991. pp 1–29) and Turner G. 1994 (Vectors for genetic manipulation. In: Martinelli S. D., Kinghorn J. R. (Editors) *Aspergillus*: 50 years on. Progress in industrial microbiology vol 29. Elsevier Amsterdam 1994. pp. 641–666).

Transformed Yeast

In another embodiment the transgenic organism can be a yeast.

In this regard, yeast have also been widely used as a vehicle for heterologous gene expression.

By way of example, the species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence of the present invention into a construct designed for expression in yeast. Several types of constructs used for heterologous expression have been developed. The constructs may contain a promoter active in yeast, such as a promoter of yeast origin, such as the GALL promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The transformed yeast cells may be selected using various selective markers. Among the markers used for transformation are a number of auxotrophic markers such as LEU2, HIS4 and TRP1, and dominant antibiotic resistance markers such as aminoglycoside antibiotic markers, eg G418.

Transformed Plants/Plant Cells

A preferred host organism suitable for the present invention is a plant.

In this respect, the basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech Mar./Apr. 1994 17–27).

Even though the promoter of the present invention is not disclosed in EP-B-0470145 and CA-A-2006454, those two documents do provide some useful background commentary on the types of techniques that may be employed to prepare transgenic plants according to the present invention. Some of these background teachings are now included in the following commentary.

The basic principle in the construction of genetically modified plants is to insert genetic information in the plant genome so as to obtain a stable maintenance of the inserted genetic material.

Thus, in one aspect, the present invention relates to a vector system which carries a nucleotide sequence or construct according to the present invention and which is capable of introducing the nucleotide sequence or construct into the genome of an organism, such as a plant.

The vector system may comprise one vector, but it can comprise two vectors. In the case of two vectors, the vector system is normally referred to as a binary vector system. Binary vector systems are described in further detail in Gynheung An et al. (1980), Binary Vectors, *Plant Molecular Biology Manual* A3, 1–19.

One extensively employed system for transformation of plant cells with a given promoter or nucleotide sequence or construct is based on the use of a Ti plasmid from *Agrobacterium tumefaciens* or a R1 plasmid from *Agrobacterium rhizogenes* An et al. (1986), Plant Physiol. 81, 301–305 and Butcher D. N. et al. (1980), Tissue Culture Methods for Plant Pathologists, eds.: D. S. Ingrams and J. P. Helgeson, 203–208.

Several different Ti and Ri plasmids have been constructed which are suitable for the construction of the plant or plant cell constructs described above. A non-limiting example of such a Ti plasmid is pGV3850.

The nucleotide sequence or construct of the present invention should preferably be inserted into the Ti-plasmid between the terminal sequences of the T-DNA or adjacent a T-DNA sequence so as to avoid disruption of the sequences immediately surrounding the T-DNA borders, as at least one of these regions appear to be essential for insertion of modified T-DNA into the plant genome.

As will be understood from the above explanation, if the organism is a plant, then the vector system of the present invention is preferably one which contains the sequences necessary to infect the plant (e.g. the vir region) and at least one border part of a T-DNA sequence, the border part being located on the same vector as the genetic construct. Preferably, the vector system is an *Agrobacterium tumefaciens* Ti-plasmid or an Agrobacterium rhizogenes R1-plasmid or a derivative thereof, as these plasmids are well-known and widely employed in the construction of transgenic plants, many vector systems exist which are based on these plasmids or derivatives thereof.

In the construction of a transgenic plant the nucleotide sequence or construct of the present invention may be first constructed in a micro-organism in which the vector can replicate and which is easy to manipulate before insertion into the plant. An example of a useful micro-organism is *E. coli.*, but other micro-organisms having the above properties may be used. When a vector of a vector system as defined above has been constructed in *E. coli.* it is transferred, if necessary, into a suitable Agrobacterium strain, e.g. *Agrobacterium tumefaciens*. The Ti-plasmid harbouring the nucleotide sequence or construct of the invention is thus preferably transferred into a suitable *Agrobacterium* strain, e.g. *A. tumefaciens*, so as to obtain an Agrobacterium cell harbouring the nucleotide sequence or construct of the invention, which DNA is subsequently transferred into the plant cell to be modified.

As reported in CA-A-2006454, a large amount of cloning vectors are available which contain a replication system in *E. coli* and a marker which allows a selection of the transformed cells. The vectors contain for example pBR 322, the pUC series, the M13 mp series, pACYC 184 etc.

In this way, the nucleotide or construct of the present invention can be introduced into a suitable restriction position in the vector. The contained plasmid is used for the transformation in *E. coli*. The *E. coli* cells are cultivated in a suitable nutrient medium and then harvested and lysed. The plasmid is then recovered. As a method of analysis there is generally used sequence analysis, restriction analysis, electrophoresis and further biochemical-molecular biological methods. After each manipulation, the used DNA sequence can be restricted and connected with the next DNA sequence. Each sequence can be cloned in the same or different plasmid.

After each introduction method of the desired promoter or construct or nucleotide sequence according to the present invention in the plants the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., Crit. Rev. Plant Sci., 4:1–46; and An et al., EMBO J. (1985) 4:277–284.

Direct infection of plant tissues by *Agrobacterium* is a simple technique which has been widely employed and which is described in Butcher D. N. et al. (1980), *Tissue Culture Methods for Plant Pathologists*, eds.: D. S. Ingrams and J. P. Helgeson, 203–208. For further teachings on this topic see Potrykus (Annu Rev Plant Physiol Plant Mol Biol [1991] 42:205–225) and Christou (Agro-Food-Industry Hi-Tech Mar./Apr. 1994 17–27). With this technique, infection of a plant may be done on a certain part or tissue of the plant, i.e. on a part of a leaf, a root, a stem or another part of the plant.

Typically, with direct infection of plant tissues by *Agrobacterium* carrying the promoter and/or the GOI, a plant to be infected is wounded, e.g. by cutting the plant with a razor or puncturing the plant with a needle or rubbing the plant with an abrasive. The wound is then inoculated with the Agrobacterium. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc. Regeneration of the transformed cells into genetically modified plants may be accomplished using known methods for the regeneration of plants from cell or tissue cultures, for example by selecting transformed shoots using an antibiotic and by subculturing the shoots on a medium containing the appropriate nutrients, plant hormones, etc.

Other techniques for transforming plants include ballistic transformation, the silicon whisker carbide technique (see Frame B R, Drayton P R, Bagnaall S V, Lewnau C J, Bullock W P, Wilson H M, Dunwell J M, Thompson J A & Wang K (1994) Production of fertile transgenic maize plants by silicon carbide whisker-mediated transformation, The Plant Journal 6: 941–948) and viral transformation techniques (e.g. see Meyer P, Heidmann I & Niedenhof I (1992) The use of cassaya mosaic virus as a vector system for plants, Gene 110: 213–217).

Further teachings on plant transformation may be found in EP-A-0449375.

Ballistic Transformation of Plants and Plant Tissue

Originally developed to produce stable transformants of plant species which were recalcitrant to transformation by *Agrobacterium tumefaciens*, ballistic transformation of plant tissue, which introduces DNA into cells on the surface of metal particles, has found utility in testing the performance of genetic constructs during transient expression. In this way, gene expression can be studied in transiently transformed cells, without stable integration of the gene in interest, and thereby without time-consuming generation of stable transformants.

In more detail, the ballistic transformation technique (otherwise known as the particle bombardment technique) was first described by Klein et al. [1987], Sanford et al. [1987] and Klein et al. [1988] and has become widespread due to easy handling and the lack of pre-treatment of the cells or tissue in interest.

The principle of the particle bombardment technique is direct delivery of DNA-coated micro-projectiles into intact plant cells by a driving force (e.g. electrical discharge or compressed air). The micro-projectiles penetrate the cell wall and membrane, with only minor damage, and the transformed cells then express the promoter constructs.

One particle bombardment technique that can be performed uses the Particle Inflow Gun (PIG), which was developed and described by Finer et al. [1992] and Vain et al. [1993]. The PIG accelerates the micro-projectiles in a stream of flowing helium, through a partial vacuum, into the plant cells.

One of advantages of the PIG is that the acceleration of the micro-projectiles can be controlled by a timer-relay solenoid and by regulation the provided helium pressure. The use of pressurised helium as a driving force has the advantage of being inert, leaves no residues and gives reproducible acceleration. The vacuum reduces the drag on the particles and lessens tissue damage by dispersion of the helium gas prior to impact [Finer et al. 1992].

In some cases, the effectiveness and ease of the PIG system makes it a good choice for the generation of transient transformed guar tissue, which were tested for transient expression of promoter/reporter gene fusions.

Guar

As indicated above, in one aspect, a preferred transformed organism is transformed guar.

Guar (*Cyamopsis tetragonoloba*) is a drought-tolerant species, which originated in India and Pakistan, but is cultivated for industrial use in a number of other countries e.g. USA. Guar is taxonomically arranged with the peas and beans in the family of grain legumes. Legumes are dicotyledonous plants (dicots), which are characterised by having broad leaves and two cotyledons, in contrast to monocotyledonous plants (monocots) which display 'grass like' morphology and only have one. Examples of other dicots are tobacco and potato, and examples of monocots are cereals such as wheat, rice, maize and barley. Guar differs from most crop legumes such as peas and beans, however, in that its seed carbohydrate reserve is not starch in the cotyledons, but is galactomannan accumulated in the endosperm. The endosperm is a non-photosynthetic tissue, which envelopes the cotyledons in the seed immediately beneath the seed coat, and can be dissected away from the other seed tissues.

Guar Gum

Guar is grown as crop for animal feed and human consumption. However, an important use of guar is the extraction of guar gum or 'guaran', which is used as a functional ingredient in foods e.g. as thickener in ice cream. Guar gum consists of galactomannan—which is an extracellular cell-wall polysaccharide located in the endosperm.

In a preferred aspect, the present invention relates to the use of the promoter of the present invention to cause expression of an NOI that can affect guar gum synthesis.

Galactomannan

Galactomannan consists of a mannan backbone with substituted galactosyl-groups, the bonding of which is (1→6)-α-D-galacto-(1→4)-β-D-mannan, and the polymer has an molecular weight of 220,000 daltons (Whistler & Hymowitz 1979).

The degree of substitution, and thereby the ratio between galactose and mannose residues in galactomannan, varies between leguminous species. The ratio is approx. 0.56 in guar, and mature seeds contains approx. 35–42% galactomannan (Whistler & Hymowitz 1979).

In a preferred aspect, the present invention relates to the use of the promoter of the present invention to cause expression of an NOI that can affect galactomannan synthesis.

Endosperm Expression

In a preferred aspect, the promoter of the present invention is active in the endosperm of plant tissue.

In this respect, endosperm—as well as the embryo—are formed early in seed development of flowering plants. In particular, the endosperm is formed during double fertilisation in which, one sperm nucleus fuses with an egg to produce the embryo, and a second sperm nucleus fuses with two polar nuclei to form the triploid endosperm [Lopes & Larkin 1993]. In some, but by no means all, plants this tissue serves as a storage reservoir for the seeds, and guar and the cereals are among these. In other species, however, the cotyledons have assumed the status of the principal storage tissue of the seed, and the endosperm has become vestigial.

In cereals such as rice, wheat, barley, and maize the chief carbohydrate reserve in the endosperm is starch which accumulates intracellularly in plastids known as amyloplasts. In guar endosperm, however, the principal storage carbohydrate is galactomannan which accumulates extracellularly in the intercellular spaces, and is therefore secreted out of the cell.

During maturation, the developing seed increases in volume and mass due to significant cell expansion and accumulation of carbohydrates, protein and lipids to be used as C and N sources during germination. After maturation, the seed enters dormancy [West & Harada 1993], imposed by plant hormones, such as abscisic acid (ABA), which prevent precocious germination [Thomas 1993]. On germination of guar seeds, mannanase, and galactosidase activities break down the galactomannan of the endosperm, and the mannose and galactose released support the development of the seedling.

Carbohydrate Metabolism

In a preferred aspect, the present invention relates to the use of the promoter of the present invention to cause expression of an NOI that can affect carbohydrate metabolism, such as sucrose metabolism, particularly in a plant tissue.

In this respect, sucrose is the major photoassimilate which is transported long distances in plants from the photosynthetic 'source' tissue to the heterotrophic energy-consuming 'sink' tissues, in which it is the mainstay of carbohydrate nutrition.

The initial precursor for the synthesis of sucrose is triose-phosphate which is synthesised in the carbon-fixation (Calvin) cycle in chloroplast in photosynthetic cells. This triose phosphate (glyceraldehyde 3-phosphate) is transported to the cytoplasm and converted to fructose 6-phosphate (Fructose-6-P) and glucose 1-phosphate (Glucose-1-P). The Glucose-1-P is converted to UDP-glucose which together with Fructose-6-P are converted to sucrose 6-phosphate (Sucrose-6-P) by sucrose phosphate synthase. S-6-P is the immediate precursor for sucrose and the conversion is catalysed by sucrose phosphatase.

After its synthesis in the cytoplasm of mesophyll cells, sucrose is loaded by the companion cells into the phloem and distributed to sink tissues. The transport process is a 'mass flow' facilitated by osmotic pressure, due to a concentration gradient of sucrose between source and sink. Photosynthesis is slowed by build up of sucrose in green tissues, and so it is seen by many as a demand-led process, with the vascular tissue communicating requirement for carbohydrate by unloading of sucrose into developing sink tissues.

The developing seed is a storage-active sink organ, and is therefore a large user of sucrose. Developing seeds utilise sucrose for several purposes, one example of which is synthesis of storage polysaccharides as galactomannan in guar endosperm.

Sucrose is degraded by sucrose synthase to fructose (F) and UDP-galactose (UDPG) and through a series of conversions GDP-mannose (GDPM) and UDPG are formed. GDPM and UDPG are the immediate precursors for galactomannan and the synthesis is catalysed by mannan synthase and galactosyl transferase. Galactomannan is synthesized and transported from the golgi apparatus to the extracellular space. Another key enzyme in the synthesis of galactomannan is UDP galactose 4-epimerase.

Breakdown of sucrose in plants can be achieved through the activity of two enzymes: Invertase (E.C. 3.2.1.26) and sucrose synthase (E.C. 2.4.1.13). The name 'sucrose synthase' implies that the enzyme catalyses the synthesis of sucrose, but the metabolic role of sucrose synthase is catabolic rather than anabolic, and sucrose synthase preferentially cleaves sucrose in vivo. Consistent with this role, sucrose synthase is abundant in sink tissues such as developing seeds, but not in fully competent photosynthetic tissues. Sucrose synthase catalyses the cleavage of sucrose in the presence of UDP into UDP-glucose and fructose. By cleavage of sucrose in the presence of UDP the high energy of the sucrose glycosidic link is conserved in UDP-glucose, which can then serve as a glycosidic donor for further reactions. Invertase, on the other hand, catalyses the hydrolysis of sucrose into glucose and fructose, and probably serves less to provide carbohydrate for storage, but may furnish the immediate energy requirements of development.

In a preferred aspect, the present invention relates to the use of the promoter of the present invention to cause expression of an NOI that can affect the in situ activity of UDP galactose 4-epimerase.

Gus Reporter Gene

In some of the studies of the present invention, the E. coli uidA gene (otherwise known as the GUS gene) is used as a reporter gene. Here, the E. coli uidA gene is used as proof that the promoter of the present invention can cause expression of an NOI. However, it is to be noted that the present invention is not limited to the NOI just being the E. coli uidA gene.

In more detail, the uidA gene codes for the β-glucuronidase enzyme (GUS) which is a hydrolase that catalyses the cleavage of β-glucuronides, e.g. X-gluc and MUG. The GUS reporter gene system for higher plants was developed by Jefferson 1987.

The system utilises that the uidA gene can be fused to a promoter and introduced in to plant cells for expression. By assaying the activity of the GUS protein in transgenic tissue, the activity of a given promoter can be monitored. In some of our studies, the E. coli uidA gene has been modified to prevent glycosylation in plants, which enables GUS to retain activity when targeted to the endoplasmatic reticulum (ER).

For transient expression studies, X-Gluc (5-bromo-4-chloro-3-indolyl b-D-glucuronide) is used as a substrate in histochemical detection of GUS (qualitative), and MUG (4-methyl umbelliferyl glucuronide) as a substrate for fluorometrical detection (quantitative). The enzymatic cleavage of the colourless X-Gluc substrate produces a blue indigo precipitate at the site of cleavage. The precipitation is caused by oxidative dimerisation of the indoxyl derivative produced by the cleavage of X-Gluc. The activity of GUS can therefore be detected and analysed in transgenic tissue without extracting the enzyme before running the assay.

Production of Poi

Host organisms comprising the vectors of the present invention may be used to express the POI by use of the promoter of the present invention. In this respect, host organisms may be cultured under suitable conditions which allow expression of the POI. In some instances, expression of the POI may be constitutive such that they are continually produced, or inducible, requiring an inducer to initiate expression. In the case of inducible expression, protein production can be initiated when required by, for example, addition of an inducer substance to the culture medium.

Once the vector has been transformed or transfected into a suitable host organism then the host organism can be cultivated. Here reference can be made briefly to U.S. Pat. No. 5,543,322 which says that for cultivation of a transformant, a culture medium containing carbon and nitrogen sources assimilable by the transformant and the like can be used. Any carbon source assimilable by the transformant can be used. Examples thereof include glucose, sucrose, starch, soluble starch, dextrin, glycerin, n-paraffin and the like as well as organic acids (e.g., acetic acid, fumaric acid, benzoic acid, etc.), alcohols (e.g., methanol, ethanol, butanol, etc.), fats and oils (soybean oil, lard, etc.) and the like. They can be used alone or in combination thereof. As the nitrogen sources, there are, for example, peptone, soybean flour, cotton seed flour, meat extract, yeast extract, dried yeast, corn steep liquor, corn gluten meal, urea, ammonium salts (e.g., ammonium chloride, ammonium sulfate, etc.), nitrates (e.g., potassium nitrate, ammonium nitrate, etc.), other organic or inorganic nitrogen-containing materials and the like. They can be used alone or in combination thereof. In addition, inorganic salts (e.g., phosphates, etc.), trace metal salts (e.g., magnesium salt, calcium salt, manganese salt, etc.) can be appropriately added.

If desired, the POI can be extracted from host organisms by a variety of techniques known in the art, including enzymatic, chemical and/or osmotic lysis and physical disruption. For some applications, a preferred extraction/purification protocol may involve a centriguation step followed by, if necessary using, column chromatography such as ion-exchange or affinity chromatography.

Thus, after the desired product (e.g. the POI) has accumulated in a culture medium, a supernatant fluid containing the POI can be obtained by centrifugation or filtration. On the other hand, when the POI has accumulated in the organisms, after the cultivation, the organisms can be collected by a known method and the desired product is recovered by an appropriate method. For example, the organisms can be suspended in a buffer containing a protein denaturant such as guanidine hydrochloride, the suspension is stirred in a cold place, and then the supernatant fluid containing the desired product is obtained by centrifugation or the like.

Alternatively, after the organisms have been suspended in a buffer, the organisms can be ground by glass beads, or broken by French press, sonication, enzymatic treatment or the like, and then the supernatant fluid is obtained by centrifugation or the like.

For separation and purification of the POI from the above supernatant fluid reference can be made to U.S. Pat. No. 554,332 where it is stated that per se known separation and purification methods can be appropriately combined. As the known separation and purification methods, there are, for example, a method utilizing a difference in solubilities (e.g., salting out, precipitation with a solvent, etc.), a method mainly utilizing a difference in molecular weights (e.g., dialysis, ultrafiltration, gel filtration, etc.), a method utilizing a difference in charges (e.g., ion exchange chromategraphy, etc.), a method utilizing specific affinity (e.g., affinity chromatography, etc.), a method utilizing a difference in hydrophobicities (e.g., reverse phase high performance liquid chromatography, etc.), a method utilizing a difference in isoelectric points (e.g., isoelectric focusing, etc.) and the like.

Secretion

In some cases, it is desirable for the POI to be secreted from the expression host into the culture medium from where the POI may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the α-factor gene (yeasts e.g. *Saccharomyces* and *Kluyveromyces*) or the α-amylase gene (*Bacillus*).

Detection

A variety of protocols for detecting and measuring the expression of the POI are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on the POI may be used or a competitive binding assay may be employed. These and other assays are described, among other places, in Hampton R et al (1990, Serological Methods, *A Laboratory Manual*, APS Press, St Paul Minn.) and Maddox D E et al (1983, J Exp Med 15 8:121 1).

A wide variety of labels and conjugation techniques are known by those skilled in the art and can be used in various nucleic and amino acid assays. Means for producing labelled hybridization or PCR probes for detecting POI include oligolabelling, nick translation, end-labelling or PCR amplification using a labelled nucleotide. Alternatively, the NOI, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway, N.J.), Promega (Madison, Wis.), and U.S. Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241. Also, recombinant immunoglobulins may be produced as shown in U.S. Pat. No. 4,816,567.

Additional methods to quantitate the expression of a POI include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or calorimetric response gives rapid quantitation.

Although the presence/absence of marker gene expression suggests that the gene of interest is also present, its presence and expression should be confirmed. For example, if the NOI is inserted within a marker gene sequence, recombinant cells containing NOIs can be identified by the absence of marker gene function. Alternatively, a marker gene can be placed in tandem with a NOI under the control of the promoter of the present invention or an alternative promoter (preferably the same promoter of the present invention). Expression of the marker gene in response to induction or selection usually indicates expression of the POI as well.

Alternatively, host cells which contain the NOI may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

SUMMARY

In summation, the present invention relates to a promoter and, also to a construct comprising the same. In particular the present invention relates to the use of a promoter for the expression of a NOI in an organism.

In a preferred aspect, the present invention relates to the modification of carbohydrate metabolism by the transformation (genetic manipulation) of a plant by use of the novel promoter of the present invention to cause expression of an NOI that affects carbohydrate metabolism.

In one preferred aspect, the present invention relates to the modification of galactomannan synthesis by the transformation (genetic manipulation) of the leguminous plant *Cyamopsis tetragonoloba* (guar) by use of the novel promoter of the present invention to cause expression of an NOI that affects the galactomannan synthesis.

Deposits

The following sample was deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on 15 Mar. 1999:

| Microorganism | Strain Number | NCIMB Number |
|---|---|---|
| E. coli | TOP10 (Invitrogen) + pTBR-ScaK3 | NCIMB 41011 |

NCIMB 41011 comprises the novel nucleotide sequence of the present invention.

A restriction map of the novel nucleotide sequence of the present invention is shown in FIG. 3.

The present invention also encompasses sequences derivable from those deposits and embodiments comprising the same. The present invention also encompasses partial sequences derivable from those deposits and embodiments comprising the same, wherein those partial sequences code for regulatory elements.

The promoter of the present invention may be isolated from the deposit by use of any of the suitable restriction enzymes indicated in FIG. 2. Alternatively, one could use PCR techniques to "PCR out" the promoter sequence. Here, suitable primers would be based on the sequence presented as SEQ ID No. 1.

By way of example, for amplification of the full-length RSus3 promoter (2700 bp) from pTBR-ScaK3, the primer-pair "M13 forward" and "RSusNcoI" can be used. The upper M13 forward primer anneals to the pCR2.1-TOPO part of the clone some 110 bp from the cloning site, and the lower RSusNcoI primer anneals to the translation start codon of RSus3. Alternatively the primer-pair "AP2" and "RSusN-coI" can be used to isolate a similar fragment (AP2 anneals to the adaptor part of the cloned fragment).

For amplification of the RSus3 promoter without intron 1 from pTBR-ScaK3, the primer-pair "AP2" and "Lowexon½" can be used. The lower Lowexon½ primer is designed as follows: The 3' end of the primer corresponds to a 24 bp sequence just upstream of the 5' splicing site in intron 1. The 5' end of the primer corresponds to the 27 bp sequence between the 3' splicing site and the ATG-codon, and incorporates of a NcoI site.

Hence, in summation, the present invention relates to a promoter that is useful for causing selective expression of an NOI in the endosperm tissue/cells of a transformed plant. The NOI and/or the promoter may be heterologous to the transformed plant—in the sense that the NOI and/or the promoter may not naturally occur in the non-transformed plant. The promoter of the present invention is defined by having a nucleotide sequence corresponding to that shown as SEQ ID No. 1 or a variant, homologue, fragment or derivative thereof.

INTRODUCTION TO THE EXAMPLES SECTION AND THE FIGURES

The present invention will now be described, by way of example only, with reference to the accompanying drawings in which:—

FIG. 1 is a schematic diagram
FIG. 2 is a schematic diagram
FIG. 3 is a schematic diagram
FIG. 4 is a photograph
FIG. 5 is a schematic diagram
FIG. 6 is a schematic diagram
FIG. 7 is a schematic diagram
FIG. 8 is a schematic diagram
FIG. 9 is a schematic diagram
FIG. 10 is a schematic diagram
FIG. 11 is a graph
FIG. 12 is a schematic diagram
FIG. 13 is a schematic diagram
FIG. 14 is a schematic diagram
FIG. 15 is a photograph
FIG. 16 is a series of photographs
FIG. 17 is a graph
FIG. 18 is a graph
FIG. 19 is a schematic diagram
FIG. 20 is a schematic diagram
FIG. 21 is a schematic diagram
FIG. 22 is a schematic diagram
FIG. 23 is a schematic diagram
FIG. 24 is a schematic diagram FIG. 25 is a schematic diagram FIG. 26 is a graph.

Part I—Figures in More Detail

FIG. 1: A schematic representation (not to scale) of the promoter of the present invention and some of its associated sequences.

FIG. 2: Map of the RSus3 sequence in pScaK3 (pTBR-ScaK3) with the surrounding restriction sites. The other clones are analogues to this, but some have the opposite orientation.

FIG. 3 is a restriction map of the promoter of the present invention (SEQ ID NO: 7).

FIG. 4: Agarose gel showing the result of the semi-nested PCR. Lane 1 and 12 marker II; lane 2–6 EcoRV, DraI, PvuII, ScaI and SspI with buffer F: lane 7–11 same with buffer H.

FIG. 5. The promoter region from pScaK3 and pSspK3 were amplified from the primers M13 forward and RSus-Nco. The amplified products contain XhoI and NcoI sites for directional cloning into the unique SalI and NcoI in pGUS-NOSt as XhoI/NcoI fragments.

FIG. 7 is a schematic diagram of a construct.

FIG. 8 is a schematic diagram of a construct.

FIG. 9 is a schematic diagram of a construct.

FIG. 10 is a schematic diagram of a construct.

Figure 11:
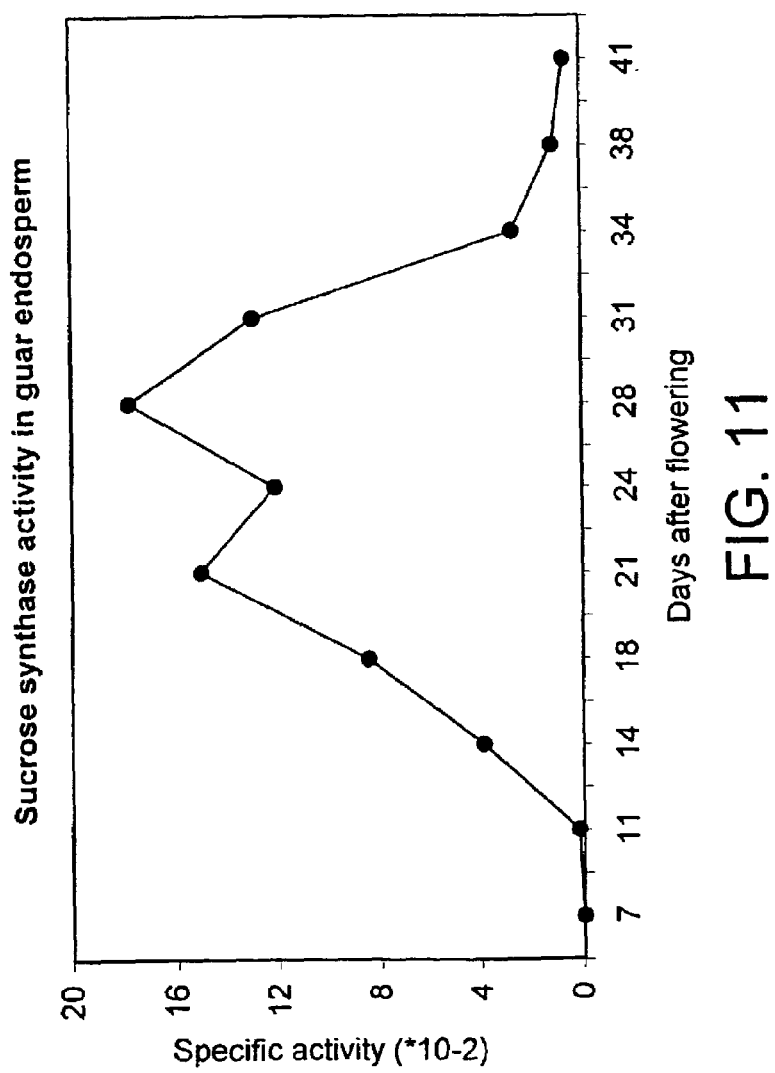

FIG. 11 shows a time course of sucrose synthase activity during development of guar endosperm. The specific activity of sucrose synthase were measured in extracts from guar endosperm at various developmental stages from 7–41 days after flowering. The value of each point is the mean sucrose synthase activities obtained from 3 to 4 independent measurements in which at least 5 endosperms from each pod were pooled.

Figure 12:
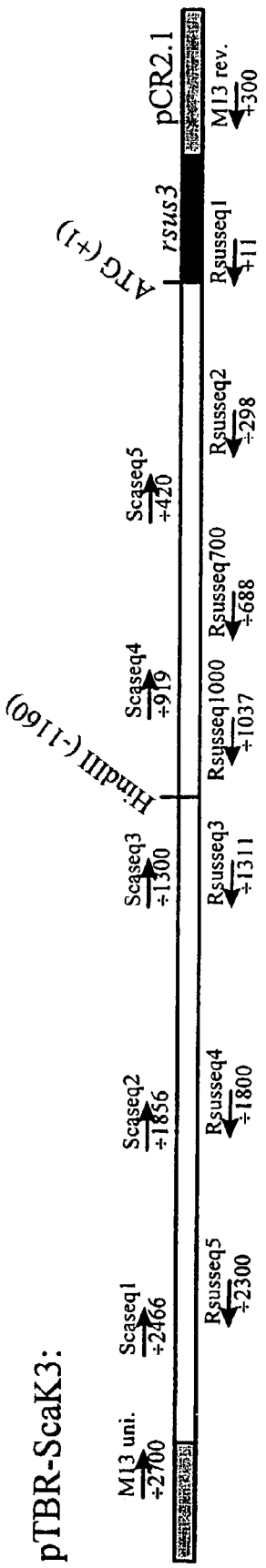

FIG. 12: Presentation of sequencing plan for pTBR-ScaK3. The arrows represent sequencing primers, and the numbers indicates approximate position of 5' end of the sequencing primers relative to the RSus3 ATG codon.

Figure 13:
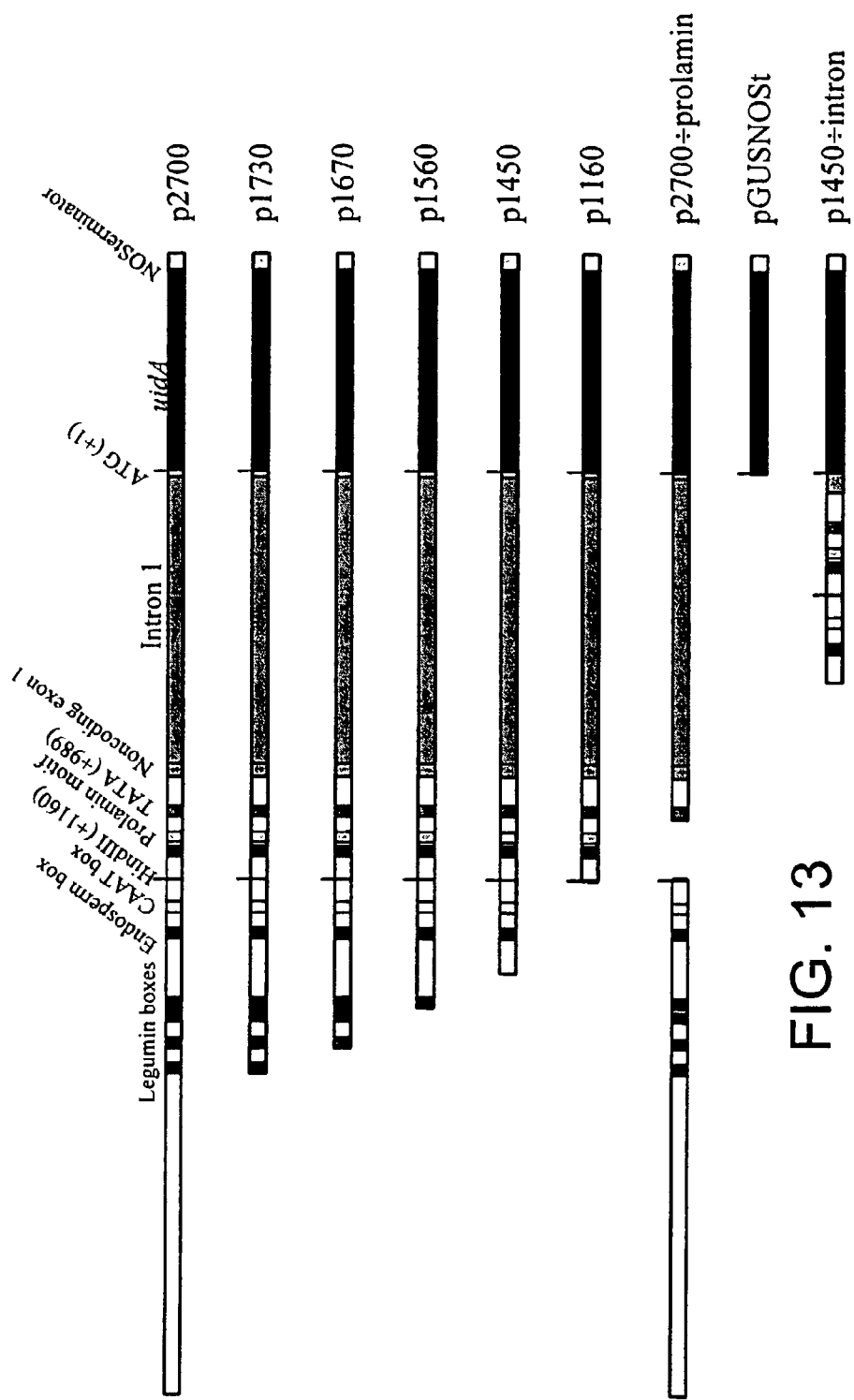

FIG. 13: Schematic presentation of various RSus3/GUS/NOSt constructs. The numbers indicates the base pairs relative to the translational start codon.

Figure 14:
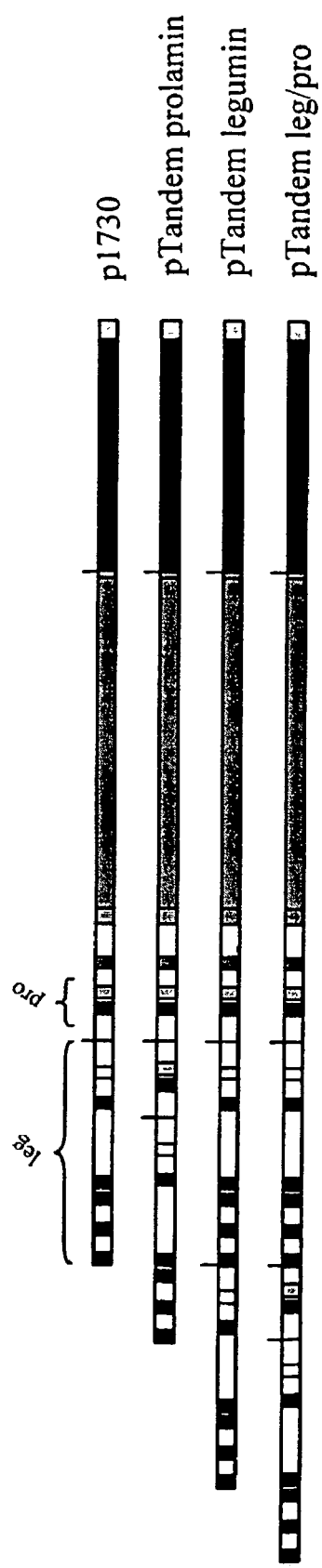

FIG. 14: Schematic presentation of various tandem Rsus3 constructs. The numbers indicates the base pairs relative to the translational start codon.

Figure 15:
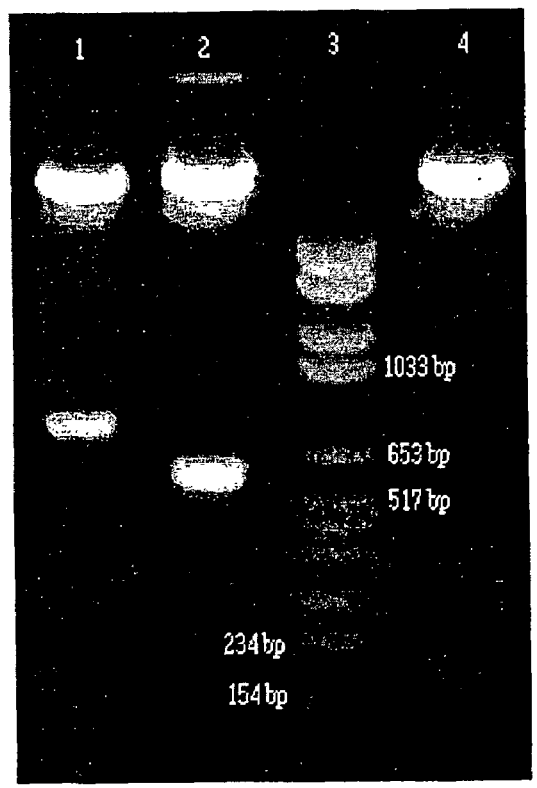

FIG. 15: Agarose gel showing the result of control digest of tandem repeat clones.

Lane 1: HindIII digest of pTandem leg/pro, which gives a specific fragment of 740 bp.

Lane 2: NheI digest of pTandem legumin, which gives a specific fragment of 570 bp.

Lane 3: DNA marker VI. Lane 4: HindIII digest of pTandem prolamin, which gis a specific fragment of 160 bp.

Figure 16A:
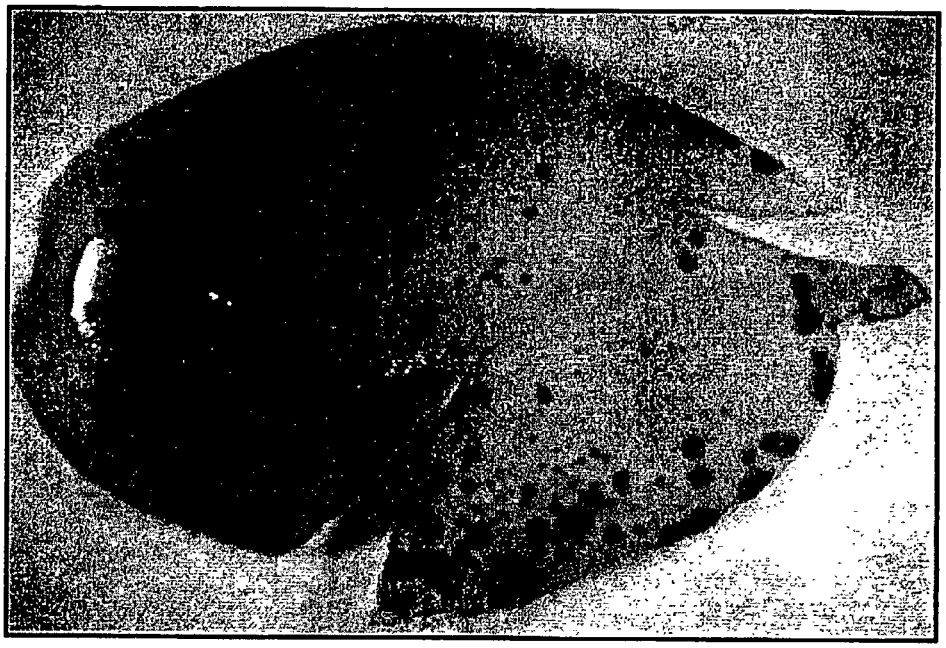

FIG. 16a is a photograph of cotyledon tissue of guar that has been ballistically transformed with the ENOS control plasmid that contains the GUS expression nucleotide sequence. This is a control study. As can be seen, high levels of transient expression of GUS are observed.

Figure 16B:

FIG. 16b is a photograph of endosperm tissue of guar that has been ballistically transformed with the ENOS control plasmid that contains the GUS expression nucleotide sequence. This is a control study. As can be seen, transient expression of GUS is observed.

Figure 16C:
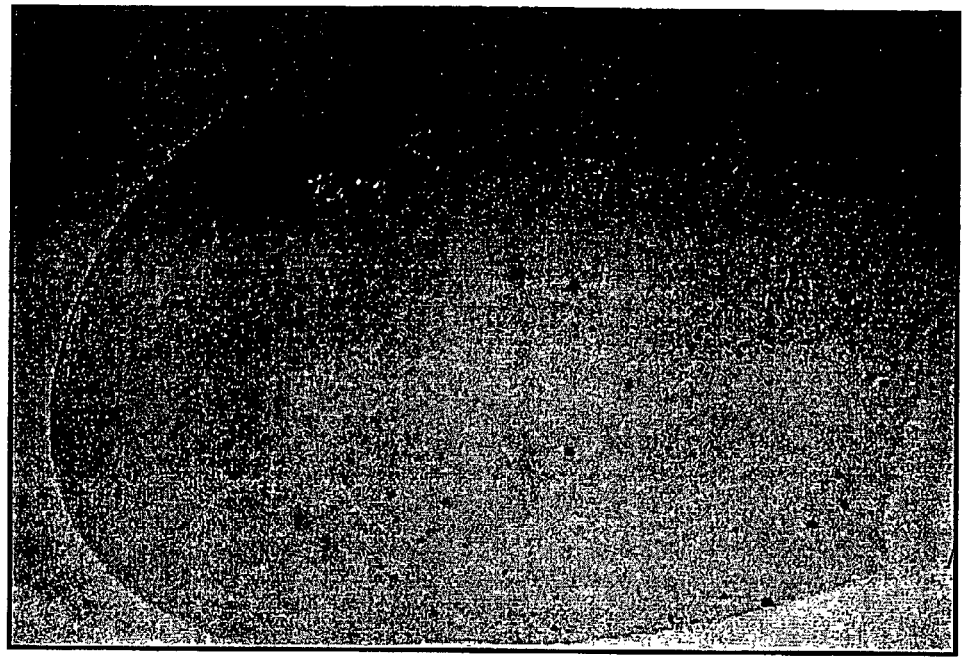

FIG. 16c is a photograph of cotyledon tissue of guar that has been ballistically transformed with the RSus3 construct plasmid p1730 (which contains a single copy of the nucleotide sequence of the present invention) that contains the GUS expression nucleotide sequence. As can be seen, very low levels of transient expression of GUS are observed.

Figure 16D:
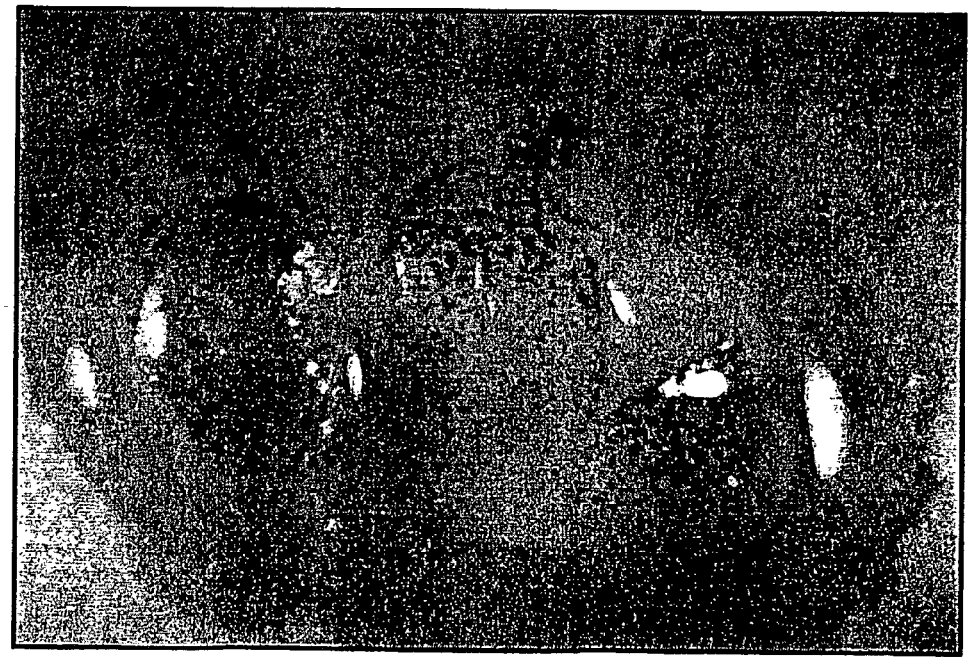

FIG. 16d is a photograph of endosperm tissue of guar that has been ballistically transformed with the RSus3 construct plasmid p1730 (which contains a single copy of the nucleotide sequence of the present invention) that contains the GUS expression nucleotide sequence. As can be seen, good levels of transient expression of GUS are observed.

Figure 16E:
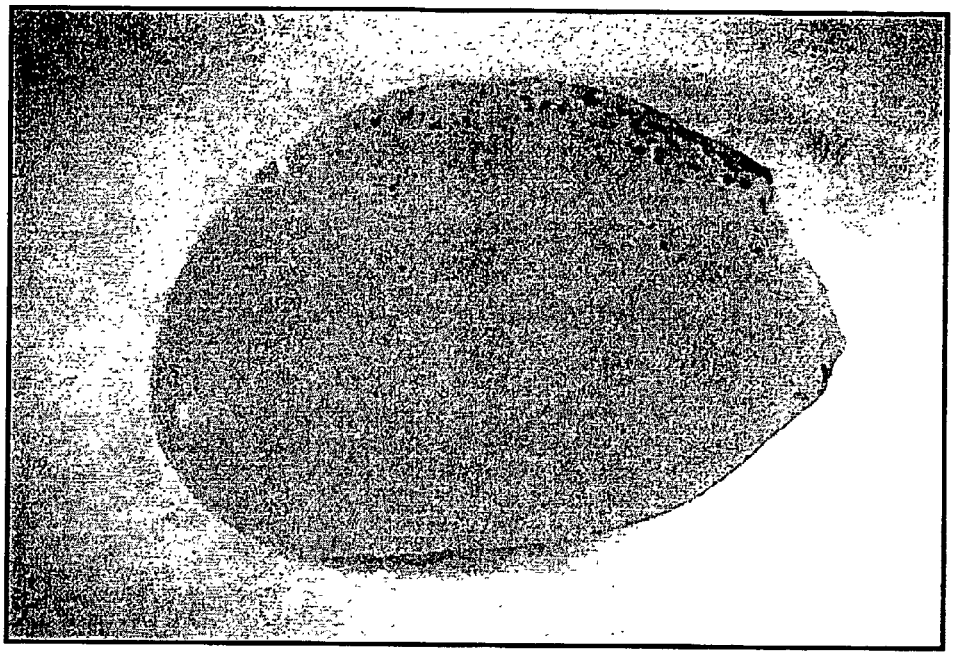

FIG. 16e is a photograph of cotyledon tissue of guar that has been ballistically transformed with the RSus3 construct plasmid pTandem leg/pro (which contains a tandem copy of the nucleotide sequence of the present invention) that contains the GUS expression nucleotide sequence. As can be seen, very low levels of transient expression of GUS are observed.

Figure 16F:

FIG. 16f is a photograph of endosperm tissue of guar that has been ballistically transformed with the RSus3 construct plasmid pTandem leg/pro (which contains a tandem copy of the nucleotide sequence of the present invention) that contains the GUS expression nucleotide sequence. As can be seen, high levels of transient expression of GUS are observed.

Figure 17:
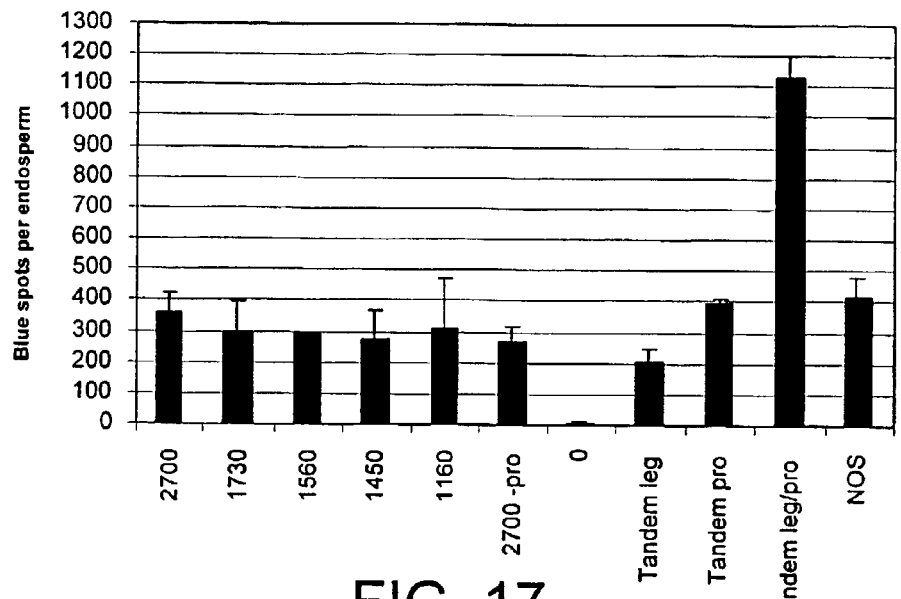

FIG. 17. Histogram showing the transient GUS expression in guar endosperms after bombardment with the RSus3 constructs. The data are presented as mean number of blue spots per endosperm together with the calculated standard error.

Figure 18:
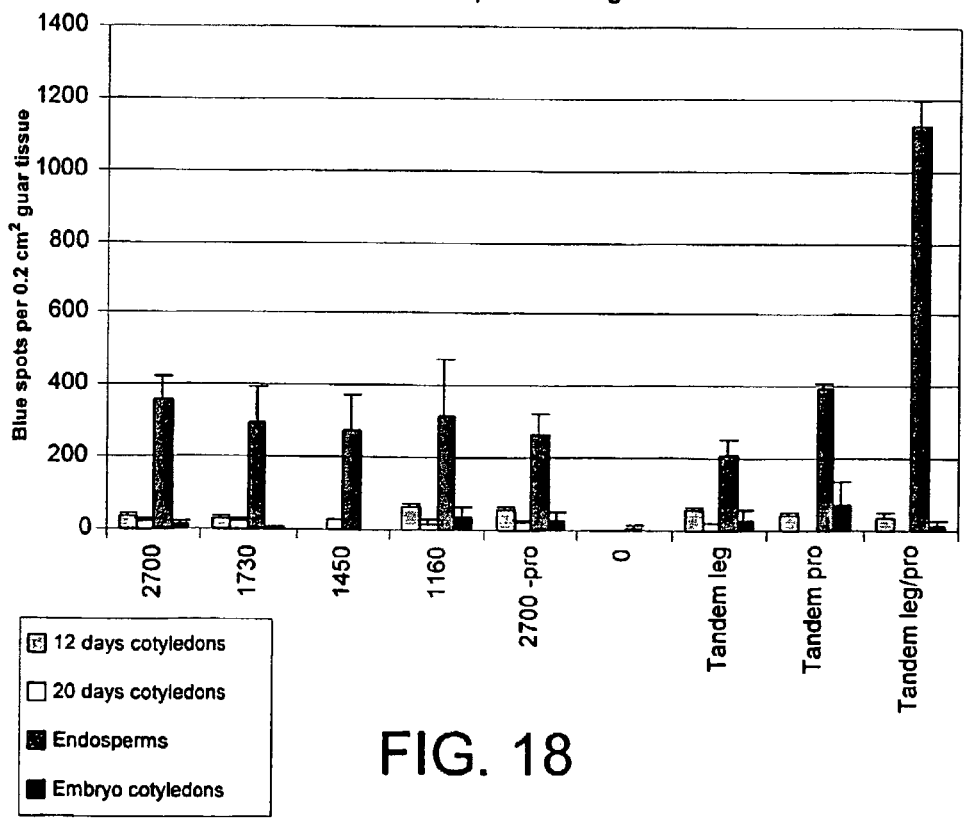
Figure 19:
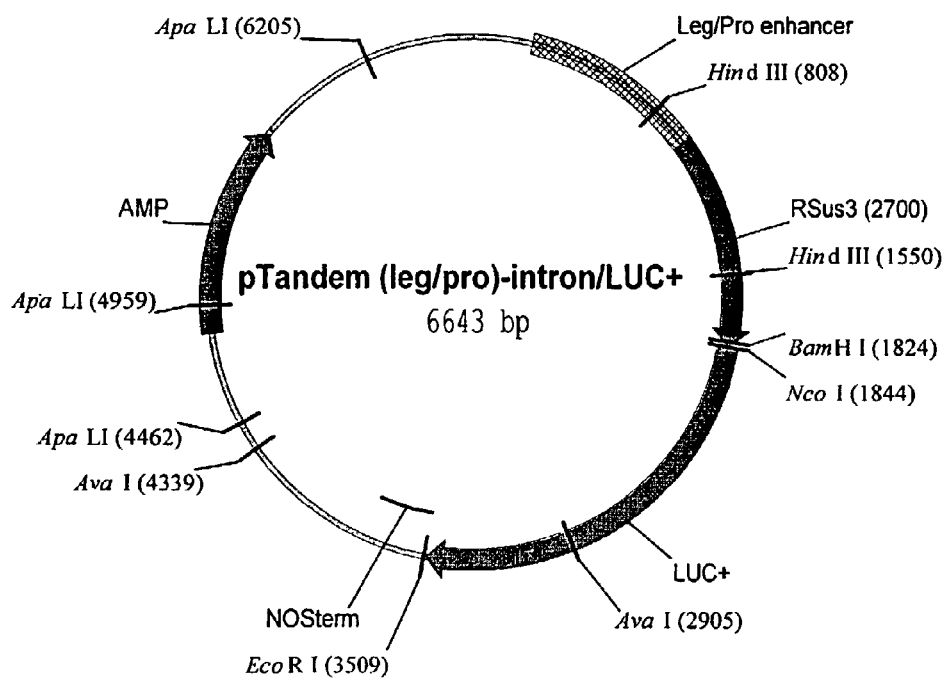
Figure 20:
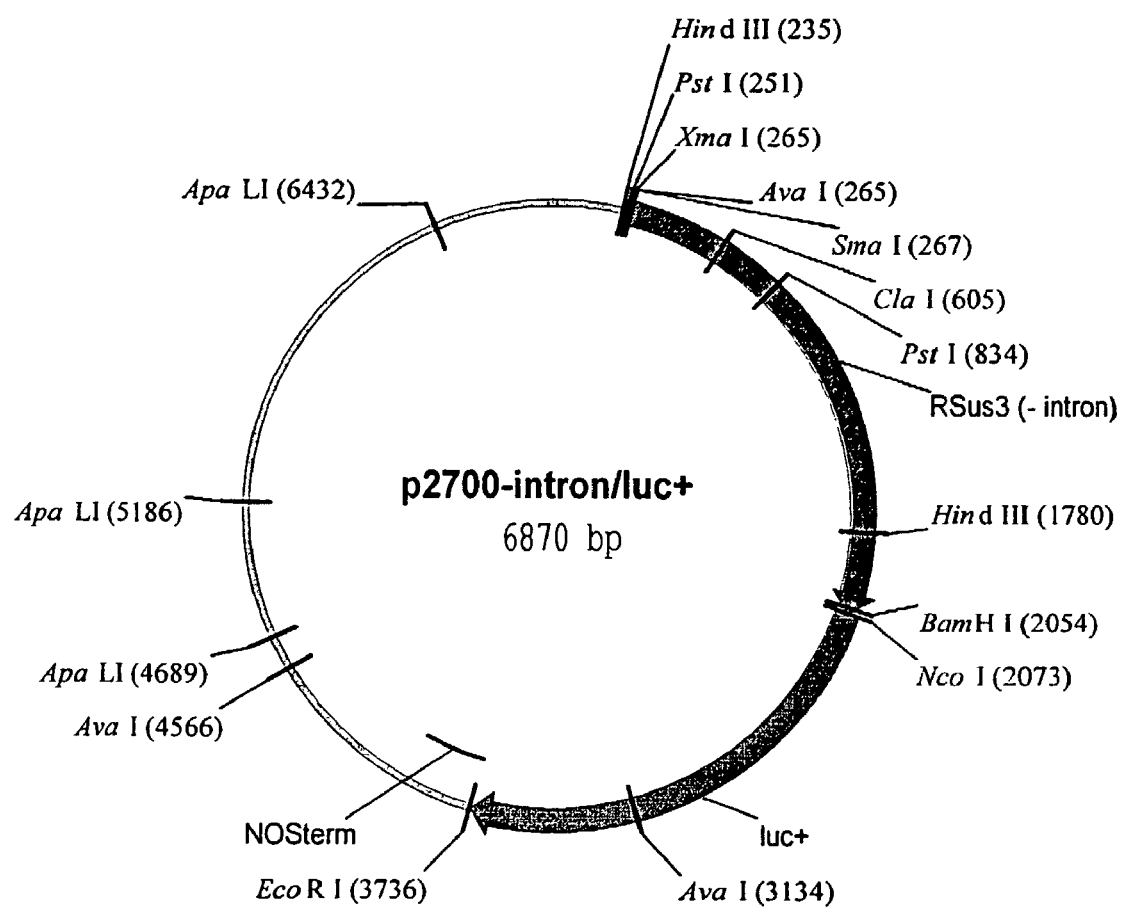
Figure 21:
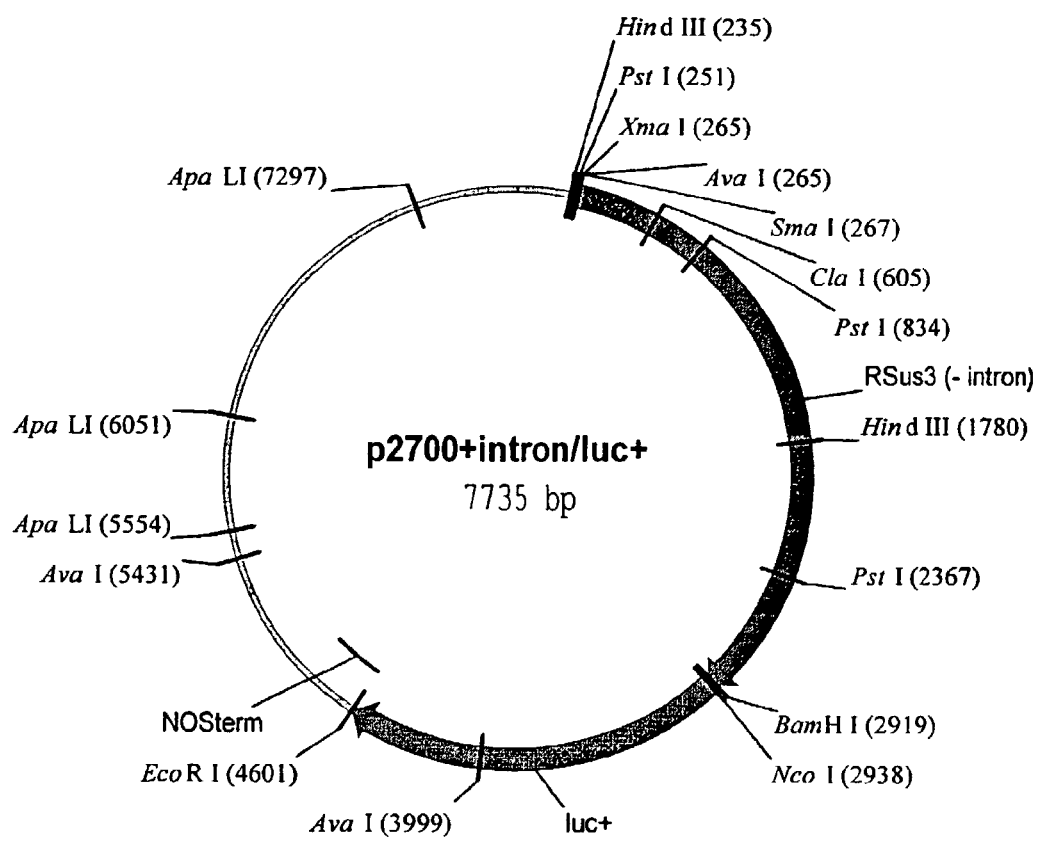
Figure 22:
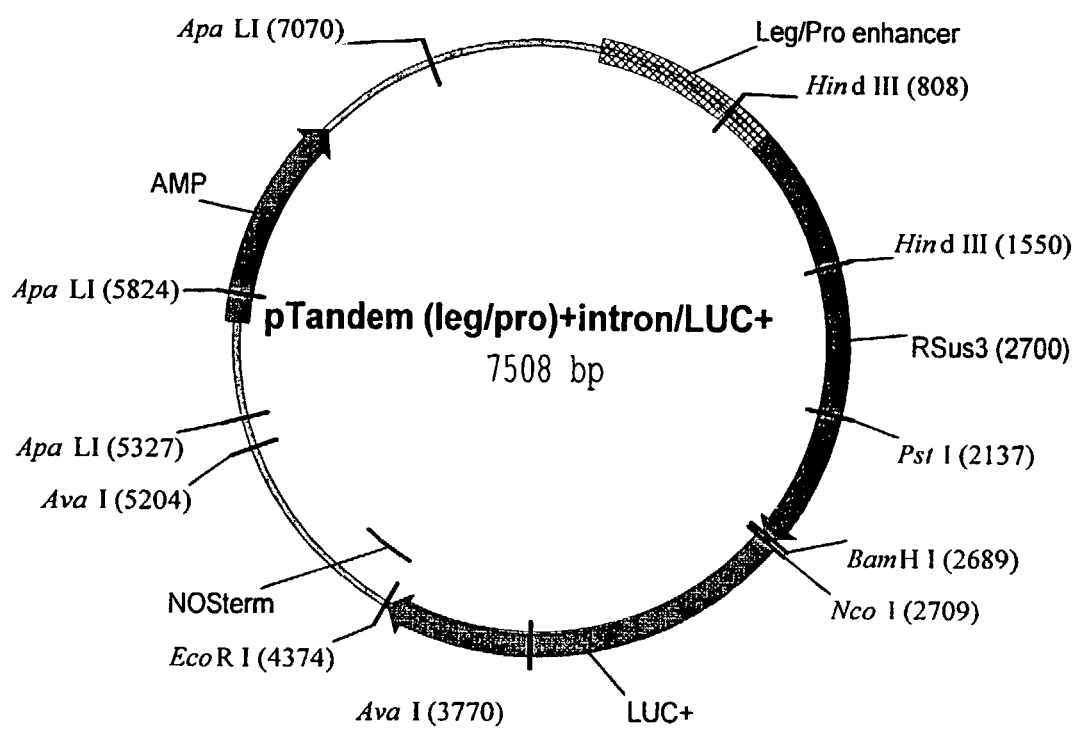
Figure 23:
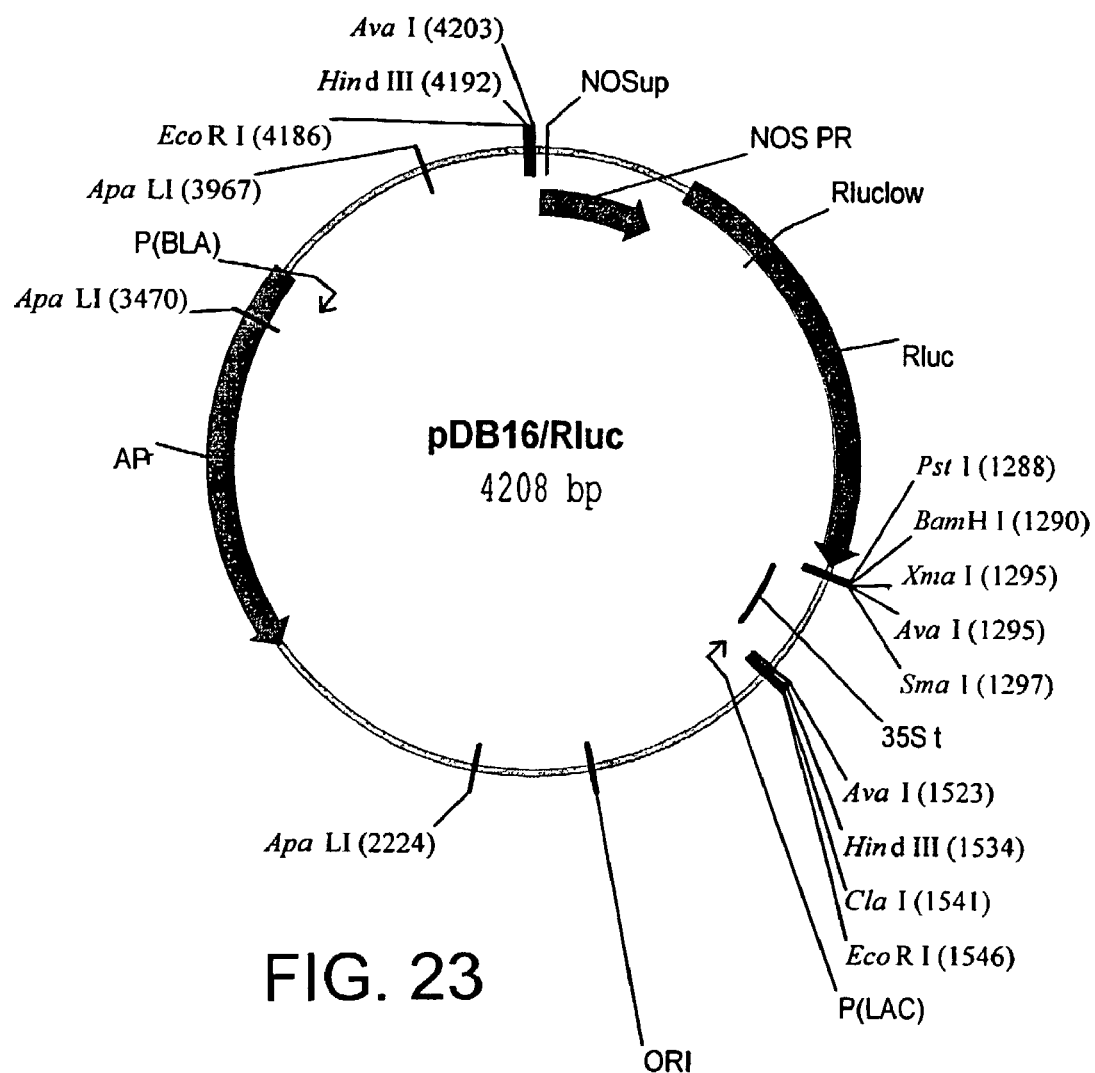

FIG. 18. Histogram showing the transient GUS expression in guar tissue after correction for tissue size. The data are presented as mean number of blue spots per cotyledon together with the calculated standard error.

Materials and Methods

Isolation of DNA

The plasmids used in this work were isolated using Qiaprep Spin Miniprep Kit and Plasmid Maxi Kit from Qiagen (Hilden, Germany). These kits give very clean plasmid preparations which are ready for use in cloning, sequencing, and transient expression assays. Further purification are therefore not necessary. 10 mM Tris-Cl, pH 8.5 was used as elution buffer and storage buffer. All DNA was stored at −20° C.

The concentration of plasmid preparations was determined, by measuring the absorbance at 260 nm in a Powerwave™ 200 spectrophotometer. An $OD_{260}$ of 1 corresponds to about 50 μg/mL DNA. The amounts of DNA in isolated fragments was estimated by comparative fluorescence of Ethidium-bromide (Etbr) stained DNA in agarose gels.

Restriction Enzymes

Enzyme digestion was performed using restriction enzymes from NEB and Boehringer M. The buffer provided by the supplier was used in the reactions. When double digestions were performed, a buffer compatible with both enzymes was chosen (e.g. digestions with both NheI and NcoI was performed in NEBuffer 2 with BSA).

Electrophoresis

Electrophoresis was used to separate and identify DNA. The DNA was stained with the fluorescent dye Ethidium bromide (EtBr) incorporated in the gel in a concentration of 0.6 μg/mL. Appropriate amount of DNA was mixed with loading buffer (0.1% bromophenol blue, 16% Ficoll 400) loaded on to the either Nusieve or Seakem agarose gels (FMC Bioproducts). TBE Buffer (0.1 M Tris, 0.09 M Boric acid, 0.001 M EDTA) was used as elecrophoresis buffer. DNA were separated by electrophoresis in a 0.5–2% (w/v)

agarose gel, dependent upon the sizes of the bands of interest. For bands <1000 bp 2% Nusieve GTG agarose gels, and for bands >1000 bp 0.5–1.5% Seakem LE agarose gels were used.

DNA molecular weight marker I, II, IV, VI and VII (Boehringer M) were used for evaluation of electrophoreses DNA. The markers were provided at a concentration of 0.25 µg/µL and diluted as follows: 2 µL DNA marker, 2 µL loading buffer and 8 µL $H_2O$. Either 4 µL or 10 µL of this mixture was loaded on to gels depending upon the well size.

Selected bands were isolated from the gel, by minimal UV radiation, using Qiaquick Gel Extraction (Qiagen).

Ligation

All ligations were performed using T4 DNA ligase in the reaction buffer (66 mM Tris-HCl, pH 7.6, 6.6 $MgCl_2$, 10 mM dithiothreitol, 66 µM ATP) supplied by the manufacturer (Amersham Life Science). Fragment with Cohesive ends were ligated using 1 U T4 ligase, whereas blunt-ended fragment were ligated using 5 U of the enzyme.

To prevent intramolecular religation of open plasmid, it was treated with alkaline phosphatase from the psychrophilic shrimp Pandalus borealis (Boehringer M). This enzyme catalyses the dephosphorylation of 5' phosphates from the plasmid DNA, but is easily prevented from interfering with the subsequent ligation by heating to 60° C. for 15 minutes.

Transformation

All the plasmids were used to transform, and propagated in, supercompetent TOP10 One Shot™ Cells (Invitrogen) Genotype: F mcrA Δ(mrr-hsdRMS-mcrBC) Φ80lacZΔM15 ΔlacX74 deoR recA1 araD139 Δ(ara-leu)7697 galU ga/k rpsL endA1 nupG.

50 µL of supercompetent cells were carefully mixed with 1–5 µL of ligation mixture, and incubated on ice for 30 minutes, after which a 30 second heat shock was performed, followed by a 2 minute recovery period on ice. Finally, 250 µL of SOC medium were added, and the cells were incubated in an orbital shaker at 37C for 30 minutes, before spreading on to LB plates containing 100 µg/ml ampicillin.

Polymerase Chain Reaction (PCR)

Polymerase chain reaction (PCR) is a technique which is based on in vitro amplification of a specific DNA sequence using synthetic primers flanking the sequence, and a thermostable DNA polymerase (e.g. Taq DNA Polymerase) for replication of the DNA.

A wide range of PCR techniques were extensively used in this study, e.g. Hot Start, Touch Down, Long PCR, Nested PCR and Sequencing PCR.

For optimization of PCR reactions the PCR optimizer™ Kit (Invitrogen) was applied. This kit comprises 16 buffers of four different pH values, each supplied with a range of four different magnesium ion concentrations, and eases optimization of PCR reactions.

The following polymerases were used:
AmpliTaq Gold™ (Perkin-Elmer)
Expand™ High Fidelity PCR system (Boehringer M)
Taq DNA polymerase (Pharmacia Biotech)

Expand™ High Fidelity PCR system is a polymerase mix of the Taq and Pwo polymerases, and is designed for amplification of PCR products up to 12 kb with high specificity. Taq posses 5'→3' transferase activity and generates ends with single 3' A overhang, whereas Pwo posses 3'→5' exonuclease activity and generate products with blunt ends.

With the exception of cycle sequencing, all PCR reactions reported here used the Hot Start technique, which minimizes binding of primers to poorly matched sites on the template at low temperatures, and the subsequent amplification of the spurious extension products formed in the first cycle of the reaction. This is achieved by preventing polymerisation before a substantial period of denaturation of the template has elapsed, and this was effected in two different ways depending on the type of polymerase.

When the Expand™ or AmpliTaq Gold™ DNA polymerase were used, a wax pellet was placed over the reaction mixture containing all components except for polymerase. The wax was melted by 95° C. for 2 min, followed by cooling to 4° C., which results in its hardening to form a thin surface on top of the reaction mixture. On to this surface 1 µL of the polymerase was added and the tube was then placed in the thermocycler, which was preheated to 95° C. beforehand, and the PCR programme was started immediately.

AmpliTaq Gold™ is a thermally activated polymerase mixture which allows a hot start, without the inconvenience of overlaying polymerase on to a solid wax surface. The enzyme is provided with an inactivating antibody bound to it. The polymerase is activated by a preliminary heating step, whereby the antibodies denatures, thus rendering the enzyme active. This allows a hot start PCR without the inconvenience of overlaying polymerase on to a solid wax surface, and the denaturation time is significant longer, and therefore more thorough. In these reactions all the components were added together with wax pellet, and the reaction started as described above.

When amplification of long PCR products was desired, a time increment was added to the extension step in the PCR program.

The PCR reactions were performed in a Mastercycler (Eppendorf).

A typical example of such a reaction is summarised in the table below.

| PCR reaction | | PCR program | | |
| --- | --- | --- | --- | --- |
| Reagent | µL/reac. | Step | Temp (° C.) | Time* |
| Template (1:100) | 1 | 1 | 94 | 2' |
| 5*Buffer | 10 | 2 | 94 | 30" |
| dNTP mix | 4 | 3 | 68 | 30" |
| Upper primer 4 µM | 5 | 4 | go to 2, 29 times | |
| Lower primer 4 µM | 5 | 5 | 68 | 10" |
| Water | to 50 | 6 | 4 | infinite |
| Expand | 0.75 | | | |

*seconds: " and minutes: '

Cloning of PCR Products

Under most circumstances, isolated PCR products were cloned in pCR2.1-TOPO (Invitrogen) which was provided as a linearized fragment with single 3'-T overhangs and TOPO isomerase. This system exploits the tendency of Taq polymerase to add a single overhanging 3'-A in both ends of the amplified product The TOPO isomerase has both cleavage and ligation activity, it cleaves the vector at a CCTTT site thereby generating a single 3'-T overhang, which will religate with a PCR product with single 5'-A overhangs. This system therefore allows cloning of Taq amplified PCR products without the use of ligation with T4 ligase.

The cloning site of pCR2.1-TOPO resides in a disruptive locus of the lacZ gene, which allows clones with inserts to be selected by blue/white screening in the presence of the chromogenic substrate for β-galactosidase (x-gal). Miniprep DNA from white colonies was analysed by restriction digests, PCR and/or sequencing.

Some PCR-fragments were digested with enzymes and cloned directly into plasmid vectors without a sub-cloning step. When cohesive ends could be generated by restriction enzymes in this way, and exploited for direct cloning, substantial savings in time were achieved.

Primers

The relevant primers are shown in the Tables presented below.

---

Primers and oligos (SEQ ID NOS 8–27, respectively, in order of appearance)
Listed in alphabetic order (Storage name, size)

---

AP1: (Walking AP1a, 27-mer)
5'- GGA TCC TAA TAC GAC TCA CTA TAG GGC
AP2: (Walking AP2, 17-mer)
5'- AAT AGG GCT CGA GCG GC
Dellow1: (Dellow 1, 22-mer)
5' GCT TTC CAC CAC AAA ATG ACA C
E356: (E356, 26-mer)
5'- GGA ATT CTA GTA ACA TAG ATG ACA CC
E357: (E357, 28-mer)
5'- GGA ATT CCC CGA TCG TTC AAA CAT TTG G
HindGCN4: (HindGCN4, 24-mer)
5' GGA AGC TTG CGA AAA TGT GCA GGG
Lowexon½: (Low exon ½, 56-mer)
5' CCC ATG GCT ATC TTC TAG TTG GAT CCT CAA GCC TTG CAC TGA AGG GGA AGA GGA GG
M13 forward: (M13 forward, 16-mer, TOPO Cloning Kit (Invitrogen))
5' CAT TTT GCT GCC GGT C
M13 reverse: (M13 reverse, 17-mer, TOPO Cloning Kit (Invitrogen))
5' CAG GAA ACA GCT ATG AC
Nhedel1: (Nhedel 1, 23-mer)
5' CCG CTA GCA CAG AGG CTG AGC AG
Nhedel2: (Nhedel.2, 27-mer)
5' TGC TAG CTG GTA AAT GAC ATG CTG CTG
Nhedel3: (Nhedel.3, 22-mer)
5' CGC TAG CAG AGG CAG CAA GCT C
NheGCN4: (Nhe GCN4, 22-mer)
5' GGG CTA GCG AAA ATG TGG AGG G
Oligo 1: (Walking Adaptor, 44-mer):
5' CTA ATA CGA CTC ACT ATA GGG CTC GAG CGG CCG CCC GGG CAG GT
Oligo 2: (Walking AP1b, 8-mer)
5'phosphate- AC CTG CCC - 3'amine
pGUS lower: (pGUS lower, 22-mer)
5' CTG GCG AAA GGG GGA TGT GCT G
Rsus3: (Lower RSus 3 Spe, 25-mer)
5' ACG ACG GAA TGG ATA ATA GCA GAT A
RsusNco: (RsusNco1, 21-mer)
5' GTT TCC CCC ATG GCT ATC TTC
RsusTATA: (RSusTATA, 21-mer)
5' CCT CCC TGA AGC TTT TCG TGT
UppCR2.1: (UppCR2.1, 44-mer)
5' ATT AGG CAC CCC AGG CTT TAC ACT TTA TGC TTC CGG CTC GTA TG

---

Lower sequencing primers
(SEQ ID NOS 28–34, in order of appearance)
(Listed in numerical order):

---

RSusseq 1
5' Cy5- GT TTC CCC CAT TGC TAT CTT C
RSusseq 2
5' Cy5- AG TGC CAG GTT CAA GGA CA
RSusseq 700
5' Cy5- AC CAA TCC CAG AAA CCC AAG C RSusseq 1000
5' Cy5- GT GTC CCC TGC CTC ACT CC
RSusseq 3
5' Cy5- CC GGC TAA GTT AAA AAA AAA
RSusseq 4
5' Cy5- CT GTG CCG TTG GAA GCG TCA T
RSusseq 5
5' Cy5- CG CAG ATG GGT TCA GCC TTC A

---

Upper sequencing primers
(SEQ ID NOS 35–39, respectively, in order of appearance)
(Listed in numerical order)

---

Scaseq 1
5' Cy5- GG TCG GCA CAT TGA GAG GTC
Scaseq 2
5' Cy5- CA CAC CCA ACG CTC ACC GAT G
Scaseq 3
5' Cy5- AG GAC GGT TTT GGT TGG GAT T
Scaseq 4
5' Cy5- TC CTC CTC TTC CCC CTT CAG TG
Scaseq 5
5' Cy5- AT CTG GCA ACC TTT TGT TTC T

---

M13 sequencing primers
(SEQ ID NOS 40 and 41, respectively, in order of appearance:

---

M13 Reverse
5' Cy5- CA GGA AAC AGC TAT GAC
M13 Universal
5' Cy5- CG ACG TTG TAA AAC GAC GGC CAG T

---

Sequencing

The Rsus 3 promoter region was sequenced with a ALFexpress DNA sequencer. The ALFexpress is designed for automated detection of fluorescently labelled DNA molecules separated by electrophoresis.

Cy5-labelled fluorescent M13 reverse and forward primers for the pCR2.1-TOPO vector was used for sequencing of 5' and 3' ends of cloned PCR products. In addition Cy5-labelled sequencing primers was designed for specific regions of the Rsus3 promoter region, using the described OLIGO™ program—Version 5.0 for Windows (National BioSciences Inc, Plymouth, Ma).

Materials for Sequencing

ALFexpreSST™ DNA Sequencer (Pharmacia biotech AB)

Thermo Sequenase fluorescent labelled primer cycle sequencing kit with 7-deaza-dGTP (Amersham Pharmacia biotech)

ReproGel™ Long Read, for polyacrylamide gel electrophoresis with the ALF® family of instruments (Amersham Pharmacia Biotech)

ReproSet™, for UV polymerisation of Reprogel™ (Amersham Pharmacia Biotech)

ALFwin™ Sequence Analyser 2.00, Windows 95 based program that controls ALFexpress (Amersham Pharmacia Biotech)

Diodeoxy chain terminator sequencing was performed in a thermocycled reaction using the special mutant polymerase ThermoSequence supplied by Amersham Pharmacia Biotech which has been selected both to accept fluorescently labelled primers and to have equal affinity for the four diodeoxy chain terminators. Band compressions on the gel were limited by the use of 7-deaza-dGTP in the reaction.

Sequence Analysis

The resulting sequences was assembled using Winseq 1.01, developed by F. G. Hansen, Department of Microbiology, DTU, Denmark. After this preliminary sequence assembling, the sequence analysis was performed using the same program.

Isolation of the RSus 3 Promoter Region from Rice Genomic DNA

The rice sucrose synthase 3 (RSus3) promoter region was isolated from rice genomic DNA using the chromosome walking technique described by Siebert et al. 1995, which is an adaptor mediated PCR method, designed to amplify an unknown sequence which is flanking a known sequence.

Genomic DNA is first digested with enzymes which produce blunt ended products (DraI, EcoRV, PvuII, ScaI or SspI) on to which adaptors are ligated. The result is the generation of 5 DNA-libraries, which can serve as templates for a PCR, using one primer specific to the known sequence and an adaptor-specific primer which is described in Siebert et al (ibid).

The adaptor sequence and the adaptor primer (AP1) and the nested adaptor primer (AP2) was provided. The adaptor was designed with an aminogroup in 3' end, which prevents amplification from the AP1 primer binding site, unless there is an initial round of amplification from e.g. a gene-specific primer [After Siebert et al., 1995].

The adaptor incorporates two features which ensure that template with adaptor binding sites at both ends will not be amplified. Firstly, due to an amino group in the 3' end of the adaptor, the generation of an AP1 primer binding site by extension of the lower strand 3' end is prevented. Thus, the only circumstances in which an AP1 primer binding site is formed during the PCR, are those in which there is an initial round of amplification from a primer which binds within the restriction fragment. Secondly, amplification of template, formed by unspecific priming from AP1, will be suppressed. Fragments formed in this manner contain inverted terminal repeats in the single stranded product, which will form a secondary stem-loop structure, which is more stable than the template-primer hybrid. The formation of the stem-loop structure prevents annealing of primer, which suppresses amplification of unspecific PCR products. The specificity of the method is further improved by reamplification of the product using a nested PCR primer.

Preparation of Genomic DNA

Genomic DNA was obtained from rice. 1 μg of this DNA was digested with 20 U of either of the following blunt end enzymes: DraI, EcoRV, PvuII, ScaI and SspI in a total volume of 50 μL.

The digestions were run through an enzyme remover column (Amicon) and concentrated by alcohol precipitation followed by dissolving in 20 μL TE.

The adaptor was prepared by mixing 800 pmol of each of Oligo 1 and Oligo 2 in a total volume of 22 μL. The mix was denatured by treatment at 94° C. for 1 min., and transferred on to ice.

An excess of the adaptor was ligated with the blunt-end digests using T4 DNA ligase. 4 μL adaptor and 13 μL digest were mixed with 10 U T4 DNA ligase in a total volume of 30 μL, and incubated at room temperature for 24 hours.

Excess adaptors were removed after ligation with the Qiaquick PCR purification kit (Qiagen), which recovers >100 bp PCR products and thereby also will remove excess adaptor.

PCR Screening for the RSus3 Promoter Region

For isolation of the RSus3 promoter region, the following sequence-specific primer was designed:

5'-ACG ACG GAA TGG ATA ATA GCA GAT A-3' (SEQ ID NO: 43)

The 3' end of this antisense primer anneals approx. 300 bp downstream of the ATG of RSus3.

The amplification was performed in a Mastercycler (Eppendorf) as a hot started, two step, PCR (68°/94° C.). To ensure optimal product length and limitation of errors the proof-reading thermostable DNA polymerase mixture Expand™ (Boehringer M) was used.

For additional optimisation of the amplification, a PCR with one nested primer was performed. After the initial PCR (primer-pair AP1/Rsus3), a secondary semi-nested amplification (primer-pair AP2/Rsus3) was performed, using the product from the initial amplification as template.

The composition and reaction conditions for the initial PCR are summarised in the table below.

| Initial PCR reaction | | PCR program | | |
|---|---|---|---|---|
| Reagent | μL/reac. | Step | Temp (° C.) | Time* |
| Template (1:20) | 5 | 1 | 94 | 1' 45" |
| 5x Buffer (E, F, G and H) | 10 | 2 | 94 | 15" |
| dNTP mix (10 mM) | 4 | 3 | 68 | 4" |
| AP1 (4 μM) | 5 | 4 | go to step 2, 9 times | |
| Rsus3 (4 μM) | 5 | 5 | 94 | 115" |
| Water | 20 | 6 | 68 | 4' + 20"/cycle |
| Expand ™ | 0.75 | 7 | go to step 5, 19 times | |
| | | 8 | 4 | infinite |

*minutes:' and seconds: "

Buffer E, F, G, and H for the PCR optimizer™ Kit (Invitrogen) were chosen for optimisation of the buffer conditions.

The semi-nested PCR was performed as Outlined in the table below.

| Secondary PCR reaction | | PCR program | | |
|---|---|---|---|---|
| Reagent | μL/reac. | Step | Temp (° C.) | Time* |
| Template (1:100) | 1 | 1 | 94 | 1' 45" |
| 5x Buffer (F and H) | 10 | 2 | 94 | 15" |
| dNTP mix (10 mM) | 4 | 3 | 68 | 4' |
| AP2 (4 μM) | 5 | 4 | go to step 2, 9 times | |
| Rsus3 (4 μM) | 5 | 5 | 94 | 15" |
| Water | 25 | 6 | 68 | 4' + 20"/cycle |
| Expand ™ | 0.5 | 7 | go to step 5, 19 times | |
| | | 8 | 4 | infinite |

*minutes:' and seconds: "

compatible with SalI and, since no internal XhoI sites are present in the RSus3, this XhoI site represents the 5' end of all of the native RSus3 fragments.

Sequencing revealed that the sequence around the ATG start codon in RSus3 was CAATGG. So a introduction of the NcoI (CCATGG) in the consensus sequence around the ATG only affects a single basepair. For generation of the 3' end of the promoter region, the RSus3Nco primer was therefore designed with a NcoI site positioned at the ATG start codon for translational fusion of amplified promoter fragments with the uidA gene in pGUSNOSt.

For amplification of the two RSus3 fragments (1450 bp and 2700 bp) the primer-pair M13 forward/RSusNco was used and the RSus3 fragments were amplified from pSspK3 and pScaK3. The M13 primer anneals to the pCR2.1-TOPO part of the pSsp and pSca clones some 110 bp from the cloning site.

The two RSus3 fragments were amplified according to the following scheme:

| PCR reaction | | PCR program | | |
|---|---|---|---|---|
| Reagent | μL/reac. | Step | Temp (° C.) | Time |
| Template* (1:20) | 5 | 1 | 95 | 2' |
| 5x Buffer (G and H) | 10 | 2 | 95 | 1' |
| dNTP mix (10 mM) | 4 | 3 | 55 | 1' |
| M13 forward (4 μM) | 5 | 4 | 72 | 2' |
| RsusNcol (4 μM) | 5 | 5 | go to 2, 25 times | |
| Water | 20 | 6 | 72 | 10' |
| Expand ™ | 0.5 | | 4 | 0' |

*Qiagen miniprep of pSspK3 or pScaK3

The resulting products were cloned in pCR2.1-TOPO and then subcloned into pGUSNOSt as XhoI/NcoI fragments. Positive clones were identified by restriction mapping of miniprep DNA. Although the pGUSTNOSt was linearised with both SalI and NcoI, the vector was treated with phosphate before ligation to prevent religation of plasmid that was cut with only one enzyme due to the close placement of the SalI and NcoI sites (G/TCGAC/CATGG) (SEQ ID NO: 43).

The NOS terminator was amplified from pDB2 as a 266 bp fragment with the E357/E356 primerpair, each of which contained an EcoRI site 5' to the annealing region. The amplified fragment was cloned in pCR2.1-TOPO, a positive clone was identified, and named pNOSt9. This was sequenced in both directions with universal and reverse sequencing primers (pCR2.1-TOPO) and the resulting sequence was verified using the BLAST function in the Entrez search engine. NOSt was excised from pCR2.1-TOPO with EcoRI and cloned into the unique site for this enzyme in pGUSN358→S. The orientation of the fragment in pGUSN358→S was tested by PCR using the primer pairs E357/pGUSlower for the correct orientation, and E356/pGUSlower for reverse orientation (product of 350 bp). A clone with NOSt in the correct orientation was selected, and named pGUSNOSt 2 (5253 bp), which was later just referred to as pGUSNOSt, whereas a clone with NOSt in reverse orientation was selected and named pGUSNOSt1.

Cloning of the RSus3 Promoter in pGUSNOSt

The initial goal was to clone as much as possible of RSus3 promoter into pGUSNOSt, without any change of the promoter sequence.

Restriction mapping of the RSus3 promoter localised the following features:

1. An internal HindIII site approx. 1200 bp upstream the ATG codon.
2. A PstI site in clones originating from rice DNA template digested with Sca I (pSca clones), but not in those digested with Ssp I (pSsp clones).
3. Several SphI sites in both pSca and pSsp clones.
4. No SalI and NcoI sites were found in any of the cloned fragments.

These characteristics limited the number of unique restriction sites for cloning of the RSus3 promoter in pGUSNOSt. Only SalI and NcoI were available for cloning of the RSus3 promoter.

Figure 5:
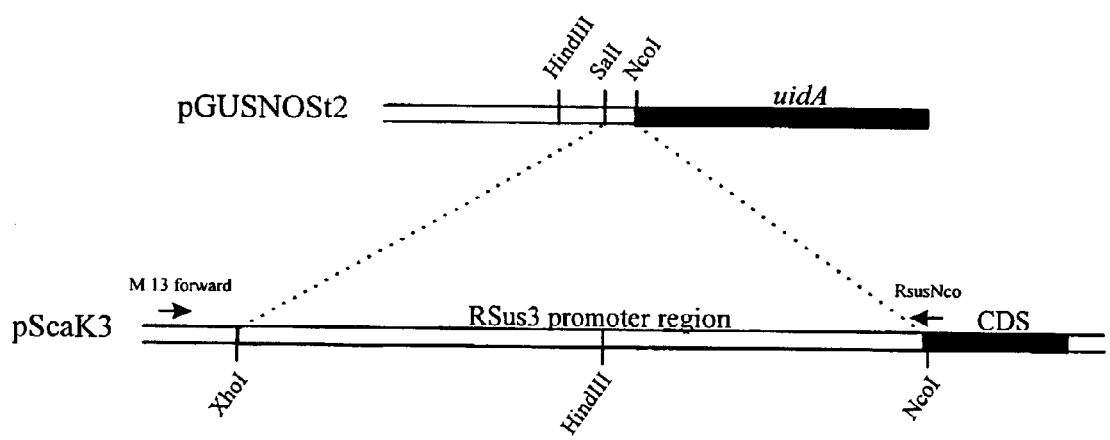

The cloning strategy was to generate two RSus3 upstream fragments (1450 bp and 2700 bp) with ends compatible to the SalI and NcoI sites for directional and translational fusion of the RSus3 promoter with the uidA gene. The cloning strategy is outlined in FIG. 5.

The adaptor from the chromosome walking technique contains a XhoI site and therefore the isolated RSus3 promoters in the pSsp and pSca clones all contain this XhoI site in the 5' end of the promoter region. Overhanging ends generated from cutting with XhoI are compatible with SalI and, since no internal XhoI sites are present in the RSus3, this XhoI site represents the 5' end of all of the native RSus3 fragments.

Sequencing revealed that the sequence around the ATG start codon in RSus3 was CAATGG. So a introduction of the NcoI (CCATGG) in the consensus sequence around the ATG only affects a single basepair. For generation of the 3' end of the promoter region, the RSus3Nco primer was therefore designed with a NcoI site positioned at the ATG start codon for translational fusion of amplified promoter fragments with the uidA gene in pGUSNOSt.

For amplification of the two RSus3 fragments (1450 bp and 2700 bp) the primer-pair M13 forward/RSusNco was used and the RSus3 fragments were amplified from pSspK3 and pScaK3. The M13 primer anneals to the pCR2.1-TOPO part of the pSsp and pSca clones some 110 bp from the cloning site.

The two RSus3 fragments were amplified according to the following scheme:

| PCR reaction | | PCR program | | |
|---|---|---|---|---|
| Reagent | μL/reac. | Step | Temp (° C.) | Time |
| Template* (1:20) | 5 | 1 | 95 | 2' |
| 5x Buffer(G and H) | 10 | 2 | 95 | 1' |
| dNTP mix (10 mM) | 4 | 3 | 55 | 1' |
| M13 forward (4 μM) | 5 | 4 | 72 | 2' |
| RsusNcol (4 μM) | 5 | 5 | go to 2, 25 times | |
| Water | 20 | 6 | 72 | 10' |
| Expand ™ | 0.5 | | 4 | 0' |

*Qiagen miniprep of pSspK3 or pScaK3

The resulting products were cloned in pCR2.1-TOPO and then subcloned into pGUSNOSt as XhoI/NcoI fragments. Positive clones were identified by restriction mapping of miniprep DNA. Although the pGUSTNOSt was linearised with both SalI and NcoI, the vector was treated with phosphate before ligation to prevent religation of plasmid that was cut with only one enzyme due to the close placement of the SalI and NcoI sites (G/TCGA<u>C/CATGG</u>) (SEQ ID NO: 43).

A positive 1450 bp clone was named "p1450" and a positive 2700 bp clone was named "p2700".

Deletions of the RSus3 Promoter

In order to identify those parts of the cloned promoter regions which confer activity and specificity, we performed a molecular dissection of the cloned fragments, by effecting serial deletions of regions which were deemed from the DNA sequence to contain motifs, identified in the promoters of other genes.

The generation of RSus3 promoter deletions involved PCR amplification of selected parts of the promoter region, and cloning of these fragments into a construction which was based on the p1450 construct. It was decided that all truncations of the promoter would be upstream of the TATA box, which is positioned 989 bp 5' to the translation start codon, and approximately 100 bp upstream of intron 1. This strategy gave the option of retaining or later removing intron 1 from constructs, while focussing deletions upon the region in which all the recognised promoter motifs are located.

As described above, there are a limited number of restriction sites available in the pGUSNOSt MCS for cloning of truncated promoter inserts. In fact, there are no unique sites left in the pGUSNOSt part of the resulting clones. But in the adaptor part of the cloned 1450 bp and 2700 bp fragments there are a number of restriction sites.

Only a few restriction sites are unique within the RSus3 part of the p2700 and the p1450 constructs. Of these, only BamHI, BglII, BsiWI and ClaI generate cohesive ends and are therefore convenient for cloning, but BamHI is located downstream of intron 1 and BglII within it. The BsiWI and ClaI on the other hand are located only 300–400 bp from the MCS and therefore leave very little sequence that can be truncated.

So the lack of usable cloning sites led to the following strategy:

The MCS HindIII site was converted to a NheI site by partial digestion followed by fill-in with Klenow and religation of the resulting blunt ended fragment. PCR amplified fragments with NheI/HindIII could afterwards be cloned directionally in the resulting unique NheI and HindIII sites.

This strategy had several advantages, though it is quite laborious.

1) A standard test plasmid was created, which contained unique NheI and HindIII sites, into which PCR amplified products could be directionally cloned.
2) The sequence of the HindIII/NcoI fragment obtainable from all truncated clones was identical, so possible variations owing to PCR-generated mutations in this region were avoided.

HindIII→NheI Conversion for Directional Cloning of PCR Deletions

The conversion of the HindIII site in the MCS to a NheI site involved partial digestion with HindIII, filling-in of the 5' single stranded overhang with Klenow fragment, and religation which formed an NheI site. Reaction conditions for effecting a partial digestion with Hind III were established empirically, using the range of dilutions of enzyme in the tabel below and slowing the reaction by performing it at 25° C., rather than 37° C.

Reaction scheme for the partial digestion:

| sample | Plasmid dilution[1] (μL) | NEBuffer 2 (μL) | HindIII dilution[1] (μL) | H$_2$O (μL) |
|---|---|---|---|---|
| 1 | 2 | 1,5 | 2 | 9,5 |
| 2 | 2 | 1,5 | 4 | 7,5 |
| 3 | 2 | 1,5 | 6 | 5,5 |
| 4 | 2 | 1,5 | 8 | 3,5 |
| 5 | 2 | 1,5 | 10 | 1,5 |
| 6 | 2 | 1,5 | 12 | 0 |

Dilutions: 0.25 μg/μL plasmid and 0.02 U/μL HindIII

The partial digests were incubated in a Mastercycler (Eppendorf) for 15 min at 25° C. followed by 10 min at 65° C. The result was evaluated on a 1% Seakem agarose gel and sample 2 and 3 gave the best result. In these two samples there were 4 bands: 2 bands from uncut plasmid, a band from a single HindIII cut and a faint band from cutting of both HindIII sites. The latter band increased in intensity in the subsequent samples, at the expense of the single cut band.

The partially HindIII-digested 1450 bp construct was filled in using DNA Polymerase I Large Fragment (Klenow) (NEB) before ligation. In the presence of dNTP's, Klenow fragment retains the polymerization fidelity of the E. coli DNA Polymerase I without degrading 5' termini. Treatment with Klenow fragment was performed as follows:

14 μL partial digested plasmid

2 μL 10 mM dNTP mix (Invitrogen)

0.6 μL NEBuffer 2 (NEB)

2.9 μL H$_2$O 0.5 μL Klenow fragment (NEB)

The reaction was incubated for 15 min at 25° C. and 10 min at 75° C. After the filling-in reaction the singly cut plasmid band was isolated from the gel, ligated and positive clones were isolated. This strategy gives rise to two different types of clones, one with an upstream NheI site (p2700 (upNheI) 1 and 3), and one with a downstream NheI site (p2700(downNheI) 7 and 10). Although the latter type of clone was not suitable for promoter truncation studies, it found utility later during the construction of tandem repeats of promoter motifs.

Additionally, the HindIII site in the MCS of the parent plasmid pGUSNOSt, which contained no RSus3 sequence, was modified to an NheI site in a similar manner, to form pGUSNOStNheI 2 and 3, but the partial digestion was of course not necessary for the unique HindIII site in this plasmid.

Cloning of Three RSus3 Deletions in p2700(upNheI)

Figure 6:
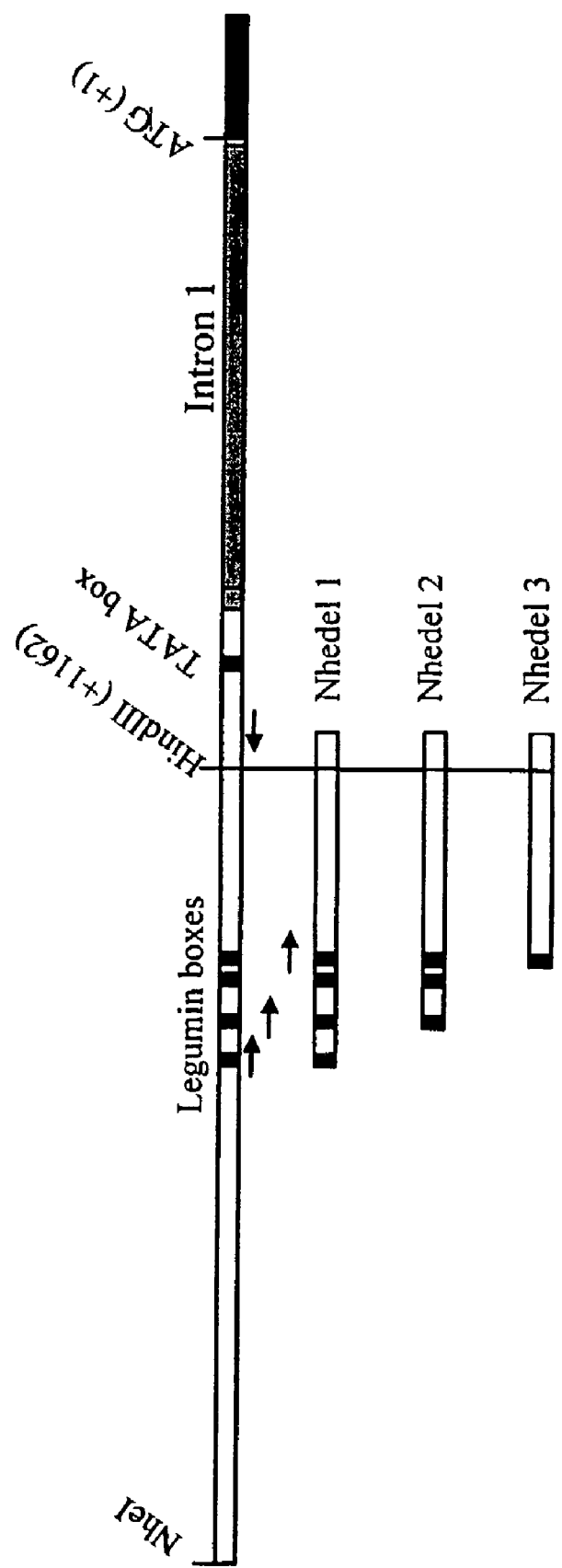
FIG. 6 is a schematic diagram of a construct.

See FIG. 6.

Three deletions were generated using the three primer-pairs with different upper primers, but the same lower primer: Nhedel1/Dellow1, Nhedel2/Dellow1 and Nhedel3/Dellow1. The Nhedel1–3 primers was designed with a NheI site and the Dellow1 primer was designed to anneal downstream of the internal HindIII site. Thus these primer-pairs results in generation of 3 different PCR products (650 bp, 590 bp and 480 bp), with the 2700 bp construct as template, each with NheI/HindIII sites for cloning in p2700(upNheI).

The amplification was performed in a Mastercycler (Eppendorf) as a 2-step PCR (68/94° C.) described in the table below.

| PCR reaction | | PCR program | | |
|---|---|---|---|---|
| Reagent | µL/reac. | Step | Temp (° C.) | Time |
| Template (1:100) | 1 | 1 | 95 | 2' |
| 5x Buffer (E, F, G or H) | 10 | 2 | 94 | 45" |
| dNTP mix (10 mM) | 4 | 3 | 68 | 45" |
| Nhedel1, 2, 3 (4 µM) | 5 | 4 | go to 2, 25 times | |
| Dellow1 (4 µM) | 5 | 5 | 68 | 10' |
| Water | 24,5 | 6 | 4 | infinite |
| Expand ™ | 0.5 | | | |

The PCR products were cloned in pCR2.1-TOPO and positive clones were identified by restriction mapping. NheI/HindIII fragments from these were isolated and cloned into p2700(upNheI) 1.

Three positive clones were identified and named "p1730" clone 3, "p1670" clone 3 and "p1560" clone 3.

The p1160 Construct

See FIG. 7.

This deletion was generated by cutting the p2700 construct HindIII. The vector was religated and two positive clones were named "p1160" clone 1 and 2.

The p2700-Prolamin Construct

See FIG. 8.

Whereas all the RSus3 deletions described above are 5' end deletions, this truncation comprises an internal deletion of 161 bp between the internal HindIII site and the TATA-box in the RSus3 promoter. Based on the RSus3 sequence, a primerpair (RsusTATA/RsusNco) was designed for amplification of a 1020 bp fragment, with a HindIII site at one end and an NcoI site at the other. This product therefore comprises Intron 1 flanked by the TATA box, and the ATG translational start codon. The primer RsusTATA contained an internal HindIII site and annealed just upstream the TATA-box. The primer RsusNco, which contains a NcoI site positioned at the ATG start codon for translational fusion of amplified promoter fragments with the uidA gene, was the same as described above in section 5.

The PCR reaction was performed as a 2-step PCR (68/94° C.) after the following scheme in a Mastercycler (Eppendorf).

| PCR reaction | | PCR program | | |
|---|---|---|---|---|
| Reagent | µL/reac. | Step | Temp (° C.) | Time |
| Template (1:100) | 1 | 1 | 95 | 2' |
| 5x Buffer (A and B) | 10 | 2 | 94 | 45" |
| dNTP mix (10 mM) | 4 | 3 | 68 | 45" |
| RsusTATA (4 µM) | 5 | 4 | go to 2, 30 times | |
| RsusNco (4 µM) | 5 | 5 | 68 | 10' |
| Water | 24,5 | 6 | 4 | infinite |
| Expand ™ | 0.5 | | | |

The 1020 bp HindIII/NcoI product was generated by PCR and cloned into pCR2.1-TOPO. Positive clones was identified, and the HindIII/NcoI fragment was cloned into 2700 bp (upNheI) (linearized with HindIII and NcoI for substitution of a corresponding 1160 bp fragment). A positive clone was isolated and named "p2700-prolamin" clone 1.

Removal of Intron 1 within the RSus3 Promoter Region

In order to create a promoter lacking Intron1, screening for the 5'-untranslated region of an RSus3 clone in a rice cDNA library, and splicing of this to the upstream promoter motifs already cloned, were initially considered. However, sequence analysis revealed the 3' acceptor splice site of intron 1 to be located only 27 bp upstream of the ATG-codon. In light of this, a preferred strategy was formulated in which the sequence of this 27 bp downstream non-coding exon was incorporated in the lower strand PCR primer used to amplify the promoter.

See FIG. 9.

A primer pair was designed for PCR amplification of the RSus3 promoter region from pSca and pSsp clones. The lower primer (Lowexon½) was designed as follows: The 3' end of the primer corresponded to a 24 bp sequence just upstream for the putative 5' splicing site in intron 1. The 5' end of the primer corresponded to the 27 bp sequence between the 3' splicing site and the ATG-codon (NcoI). The upper primer UppCR2.1 was designed to anneal to a 44 bp sequence of pCR2.1-TOPO, upstream of the M13 reverse primer site, for amplification of the RSus3 promoter without intron 1 from pSca and pSsp clones.

Both primers were quite long (Lowexon½ is 56 bp and UppCR2.1 is 44 bp), and to ensure that they were full length, they were ordered HPLC purified. Lowexon½ has the possibility to form a hairpin loop with a melting temperature of 56° C. and an internal BamHI site gives a stable primer dimer, so the PCR amplification was performed using AmpliTaq Gold an a two step program (68° C./94° C.).

Due to the potential of these long primers to form partially miss-matched double-stranded secondary structures at their 3' end, AmpliTaq gold was used instead of Expand™ polymerase, in order to avoid the modification of the oligonucleotides by the proof-reading Pwo polymerase.

The result was a very faint band of the right size, so a semi-nested PCR amplification with M13 reverse/RsusNcoI was performed using purified product as template.

This nested PCR gave a more intense band, which was cloned in pCR2.1-TOPO. A positive clone was identified and a XhoI/NcoI fragment was subcloned in pGUSNOSt (Analogous to subcloning of XhoI/NcoI fragments from pScaK3 and pSsp3). A positive clone was named "p1450-intron" clone 2.

Generation of Tandem-Repeat RSus3 Promoters

In an attempt to enhance the activity of the RSus3 promoter, a range of sequences upstream the TATA-box in RSus3 were doubled. This strategy resulted in 3 tandem-repeat RSus3 promoters, in which different parts of the RSus3 promoter region had been doubled.

See FIG. 10.

DNA sequence analysis located the majority of putative cis-elements to be within 700 bp (−1709 bp to −1027 bp), upstream of the TATA box. Therefore these 700 bp contained the elements to be doubled.

The three tandem-repeat promoters were constructed by amplification of specific sequences of the promoter, cloning of these into pCR2.1-TOPO, and finally subcloning the cloned fragments in either the NheI site or the HindIII site in the p1730 construct.

Tandem Legumin

The repeated sequence in the tandem legumin promoter were amplified after same description as NheI/HindIII product in p1730, but with p2700(downNheI) as template. This gave a similar product, only with two NheI sites, which after cloning into pCR2.1-TOPO, was subcloned as an Nhe I fragment into the NheI site of p1730. A positive clone was identified by NheI digestion, and a the orientation was established by repeating the PCR using the subclone as template. The resulting clone was named "pTandem legumin."

pTandem Leg/Pro

This tandem-repeat promoter was constructed in a similar approach. A primer pair was designed for amplification of a 750 bp fragment from the p2700 construct. The primer pair each had an NheI site (Nhedel1 used for p1730, and NheGCN4). Amplification of the primer pair Nhedel1/NheGCN4, was again performed, after same description as for the p1730 construct, and resulted in a 750 bp product (with NheI sites in both ends), which were cloned in pCR2.1-TOPO, and afterwards subcloned into the NheI site of the p1730 construct. A positive clone was identified by restriction digest, the orientation was determined in the same manner, and the clone was named "pTandem leg/pro".

pTandem Prolamin

This tandem-repeat promoters was generated in almost the same manner as the tandem leg/pro. The primerpair had same upper primer, and an analogous lower primer with a HindIII[[site (HindGCN4). The resulting product was cloned into pCR2.1-TOPO and a 170 bp HindIII/HindIII fragment from this was subcloned in the HindIII site in the p1730 construct. A positive clone was identified by restriction digest, the orientation of which was determined by repeating the PCR using the subclone as template The resulting clone was named "pTandem prolamin".

Transient Ballistic Transformation with the Particle Inflow Gun (PIG)

The Particle Inflow Gun (PIG) used in this study was in accordance with Finer et al. 1992 and Vain et al. 1993. The PIG—which is placed on a sterile-bench for minimizing contaminants—comprises a vacuum chamber with a digital vacuum sensor, an electronically operated solenoid gas valve attached to a helium cylinder regulator (1–16 bar), and a three-way valve connected to a vacuum pump. The solenoid regulates the helium flow, and is controlled by a timer relay which allows gated flow in pulses down to 25 milliseconds. The PIG is operated from a control panel with a timer relay, a digital display vacuum gauge and a fire-button.

The vacuum chamber is constructed from 3 mm stainless steel with a 20 mm acrylic door and a 10 mm inner lining of polypropylene with grooves at every 20 mm for a shelf. A silicone foam gasket between the chamber and the door seals the vacuum chamber.

A ballistic transformation device, similar to the PIG, was used in a preliminary experiment to test the feasibility of transformation of guar endosperms by particle bombardment.

Preparation of Guar Tissue for Transformation

The primary target for particle bombardment in this study was the guar endosperm, but both emerged and pre-emerged cotyledons, as well as juvenile leaves, were also used as comparative tissue. Endosperms and emerged cotyledons were isolated from 3–4 weeks old guar pods, pre-emerged cotyledons were harvested from 12 and 20 day old in vitro grown seedlings, and juvenile leaves were harvested from mature guar plants.

Isolation of Guar Tissue

Endosperms were isolated from guar seeds, under aseptic conditions, after the following procedure:

The sterilised guar pods were opened, and the seeds taken out. For each seed, the coat was carefully removed, and the remaining part was divided in endosperm and embryo. The endosperm was divided in two identical halves, and the convex dorsal side of both halves was the target surface for particle bombardment. This bisection and orientation minimised dispersal of the tissue by the helium blast. The pre-emerged cotyledons were separated from the embryo, whereas emerged cotyledons were isolated from seedlings grown in vitro in a 12 hour day/night regime. Young guar leaves were excised from full-grown plants.

The isolated tissue was transferred to the 60 mm petri dishes containing solid agarose medium and a filter paper disc (see section 1.4.3). The tissue were placed as follows: Endosperms in the centre of the petri dish with dorsal side up; cotyledons from seedlings with the upper side facing up in the centre of the petri dish; Embryo cotyledons together with endosperms.

A particle bombardment experiment consisted of 5 to 6 repeated bombardments per construct. 6–8 endosperms, 2–3 cotyledons from seedlings, or 6–7 endosperms plus 4–5 pre-emerged cotyledons were bombarded in each discharge of the PIG. For comparative analysis, both cotyledons and endosperms were bombarded in same experiment.

Sterilisation of Guar Tissue

No antibiotics were used in the transformation, so microbial contamination must be avoided. Therefore a fastidious sterilisation procedure was very important.

Sterilisation of guar pods from mature guar plants were accomplished as follows: The pods were washed in sterile water, submerged for 1 min in 96% EtOH, and finally washed 3 times with sterile water. Further sterilisation of the guar pods and seeds was not necessary.

Sterilisation of new leaves from mature guar plants was accomplished as follows: The leaves were washed in sterile water, submerged for 10s in 96% EtOH and for 20 min in 0.15% NaOCl and 0.05% Triton X-100. Finally the leaves were washed 3 times with sterile water, and stored in water until use.

Cotyledons from in vitro grown seedling were sterile and no sterilisation was necessary.

Medium

The tissue was bombarded and incubated on the following medium. The medium was a solid medium, and was based on a recipe from Donovan & Lee 1977, with a few modifications in the concentration of the ingredients.

|  | Compound | Concentration (mg/L) |
|---|---|---|
| Salts | Sucrose | 20,000 |
|  | M&S mix[1] | 4,300 |
| Vitamins | Myo-inositol | 100 |
|  | Thiamine | 0.4 |
| Aminoacids | L-Alanine | 89 |
|  | L-Arginine | 126.5 |
|  | L-Asparagine | 117 |
|  | L-Aspartic acid | 100 |
|  | L-cysteine | 69 |
|  | L-glutamic acid | 664.5 |
|  | L-Glutamine | 665.5 |
|  | Glycine | 156 |
|  | L-Histidine | 112 |

-continued

| | Compound | Concentration (mg/L) |
|---|---|---|
| | L-Isoleucine | 174 |
| | L-Leucine | 274.5 |
| | L-Lysine | 77 |
| | L-Methionine | 67 |
| | L-Phenylalanine | 287.5 |
| | L-Proline | 443.5 |
| | L-Serine | 202.5 |
| | L-Threonine | 96 |
| | L-Tryptophane | 164 |
| | L-Tyrosine | 144 |
| | L-Valine | 161.5 |
| Agar | Agar type A 1296 | 8,000 |

[1]Murashige & Skoog basal salt mixture M5524

The Particle Bombardment Procedure

The particle bombardment experiments in this study had been performed as described below.

DNA Coating of Gold Particles

A typical transformation with a single plasmid, comprising five repeated discharges of the PIG, employed 3 mg of gold particles. In practice, a larger batch of gold particles than this was freshly prepared at one time, and used for several transformations immediately afterwards. The procedure described below for the preparation of 3 mg of gold particles was adjusted such that amounts and volumes increased in proportion to amount of material.

1. 3 mg of gold particles (1.6 µm, Biorad) were treated with 50 µL 99.9% EtOH (Danisco Distillers).
2. The gold particles were vortexed in the ethanol for 3 min (full speed) and centrifuged at 10.000 g for 1 min.
3. The supernatant was removed and resuspended in 50 µL of sterile $H_2O$.
4. The particles were centrifuged at 10.000 g for 1 min, the supernatant was removed and this washing with water repeated.
5. The particles were resuspend in 50 µL 50% w/v glycerol (sterile).

The gold particles were then coated with plasmid DNA in the following manner.

1. 50 µL of gold particle suspension were removed during vortexing (14.000 min$^{-1}$) on an thermomixer (Eppendorff).
2. While vortexing (14.000 min$^{-1}$) this 50 µL sample of gold particles, the following components were sequentially added.
   10 µL of plasmid (10 µg/µL)
   50 µL 2.5 M $CaCl_2$
   20 µL 0.1 M Spermidine
3. Vortexing was continued for 3 min at 16.000 min$^{-1}$. The sample was then sedimented at 10.000 g for 10 s. and the supernatant was removed.
4. The sample was resuspended in 250 µL 99.9% EtOH, and centrifuged at the same force for 10s.
5. The supernatant was removed and the particles resuspended in 40 µL 99.9% EtOH.
6. The DNA coated microprojectiles were stored at ice until use.

Because the gold particles tend to agglomerate irreversible in aqueous solutions, it was necessary to prepare them immediately prior to use [Kikkert 1993]. $CaCl_2$ can be store at 4° C., but spermidine (N-β-aminopropyl]-1,4-butanediamine) deaminates with time, and solutions must be freshly made every month and be stored frozen at −20° C.

The purpose of the spermidine in the coating procedure is to condense the DNA by shielding the negative charges on the DNA phosphate backbone, thereby allowing hydrophobic interactions to predominate [Bloomfield 1991].

Operating the PIG

The PIG was operated in accordance with the following procedure

1. A petri-dish (60 mm in diameter) with the target tissue was placed in the vacuum chamber.
2. A stainless steel mesh (250 µm-mesh, 13 mm in diameter) was placed in the filter unit.
3. 5 µL of a suspension of DNA-coated micro-projectiles were loaded on to the centre of the steel mesh.
4. The filter unit was assembled and attached to the helium solenoid valve.
5. The 250 µm-mesh stainless steel protection screen was placed on top of the petri-dish.
6. The door and the valves were closed and evacuation of the chamber was begun.
7. The helium burst was released by pressing the fire button exactly at the point when the desired vacuum was reached.
8. The vacuum was released by opening the evacuation port, and the tissue was removed.
9. The cycle was repeated until all the samples had been bombarded. The filter unit, mesh and protection screen were changed for every new construct.

Bombardment Conditions

Good results for ballistic transformation of guar endosperms, embryos, and cotyledons were obtained with the following bombardment conditions.

The vacuum chamber was evacuated to a partial vacuum of 0.1 bar.

The target was placed at a distance of 16 cm, measured from the mesh in the filter unit to the target tissue.

The helium pressure on the regulator was set at 5 bar.

The timer relay was set at 50 milliseconds.

A stainless steel protective screen (250 µm-mesh) was placed approx. 2 cm above the target tissue Gold micro-projectiles with a diameter of 1.6 µm (Biorad) were used to carry the plasmid DNA.

Post Bombardment

After bombardment the petri-dishes, containing bombarded tissue, were sealed and incubated for 48 hour at 25° C. Endosperms and embryos were incubated in the dark, leaves and cotyledons were incubated in a 12 hour day/night regime.

GUS Assay

The histochemical GUS assay was performed as described by Jefferson 1987. After the incubation period the bombarded tissues were transferred to microtitre plates, submerged in GUS-assay buffer and incubated in dark for 24 hours at 37° C.

GUS-Assay Buffer:
100 mM Sodium-phosphate buffer, pH 7.5
0.5 mM Potassium ferricyanide (III)
0.5 mM Potassium ferrocyanide (II)
10 mM $Na_2EDTA$ (Titriplex III)
1.9 mM X-Gluc A method for determination of GUS expression, and thereby promoter activity, by counting the number of blue spots was adapted from Knudsen & Müller [1991]. After bombardment, incubation and GUS-assay the number of blue spots (expression units) was counted under a microscope, and expressed relative to the area examined.

The cotyledons and leaves were cleared in 96% EtOH in several washing steps, and were stored in 70% EtOH until counting of blue spots.

Blue spots in endosperms had to be counted immediately after the GUS incubation period. Neither storage in alcohol nor water were applicable, due to high content of galactomannan and water. The water caused swelling of the endosperm and ethanol made the endosperm shrink. These changes destroyed the expression pattern on the surface of the endosperm.

Presence of Sucrose Synthase in Guar Endosperm

A typical developmental increase in sucrose synthase, that coincides with seed-fill, was verified in extracts from guar endosperm using a continuous sucrose synthase assay (see FIG. 11). Details on the sucrose synthase assay are as follows.

Sucrose Synthase Assay

The sucrose synthase activity in developing guar endosperms was assayed in the direction of sucrose cleavage. The sucrose synthase catalyses the cleavage of sucrose in the presence of UDP into fructose and UDP-glucose:

sucrose+UDP ⇔ fructose+UDP-glucose

The activity of sucrose synthase was assayed by monitoring the formation of UDP-glucose in a continuous enzyme reaction described by Keller et al. (Keller F, Frehner M & Wiemken A (1988) Sucrose Synthase, a Cytosolic Enzyme in Protoplasts of Jerusalem Artichoke Tubers (*Helianthus tuberosus* L.) Plant Physiol. 88, 239–241). The formation of UDP-glucose was coupled to the reduction of NAD$^+$ in the presence of UDP-glucose dehydrogenase (E.C. 1.1.1.22), which catalysis oxidation of UDP-glucose to UDP-glucuronic acid:

UDP-glucose+2 NAD$^+$+H$_2$O ⇔ UDP-glucuronic acid+2 NADH

The endosperms were dissected from the developing seeds, pooled and homogenised in Hepes/KOH buffer (20 mM, pH 8.00) using a rotating pestle. During this procedure enzymatic breakdown of the galactomannan backbone was effected by addition of β-mannase (E.C. 3.2.1.78, Megazyme). The sample was centrifuged at 20,000 g for 20 minutes and the resulting supernatant was desalted using Sephadex® G-25 columns (NAP™-5, Pharmacia Biotech), for removal of endogenous sugars from the crude extract.

An appropriate amount of enzyme extract was added to the sucrose synthase assay buffer (1 ml):

20 mM Hepes/KOH (pH 8.0)
200 mM sucrose
2 mM UDP
1.5 mM NAD$^+$
20 mU UDP-glucose dehydrogenase (Sigma)

The reduction of NAD$^+$ to NADH was followed by continuous measurement of the absorbance at 340 nm in a spectrophotometer (25° C., $\epsilon_{NADH}$=6300 l mol$^{-1}$ cm$^{-1}$). The amount of UDP-glucose produced (µmol min$^{-1}$) was calculated from the slope of the resulting absorbance curve. The total amount of protein, in the remaining supernatant, was determined using the Biorad Protein Assay with bovine serum albumin as standard, and the specific activity of sucrose synthase was calculated (Units sucrose synthase per mg protein, or µmol min$^{-1}$ mg$^{-1}$).

The activity of sucrose synthase was measured in extracts from guar endosperms at various developmental stages from 7–41 days after flowering. The mean sucrose synthase activity for each developmental stage was obtained from 3 to 4 independent measurements, each of which was made with extract obtained from at least 5 endosperms from same pod.

Results

Isolation of the RSus3 Promoter Region

The rice sucrose synthase 3 (RSus3) promoter region was isolated from rice genomic DNA using the chromosome walking technique described by Siebert et al. 1995. After the semi-nested PCR reaction, 3 bands appeared in the following reactions: DraI (≈700 bp), ScaI (≈3000 bp) and SspI (≈1800 bp).

The 1800 bp and 3000 bp products were verified, as specific products obtained from the primer-pair AP2/RSus3, by single primer control reactions.

| Template\Primer | AP2 | RSus3 | AP2/RSus3 |
|---|---|---|---|
| Scat (buffer H) | — | — | ≈3000 bp |
| Sspl (buffer H) | — | — | ≈1800 bp |

The result of this single primer control reaction shows that the 1800 bp and 3000 bp originated from specific amplification from the AP2/Rsus3 primer-pair and are not single primer products. Single primer product from the AP2 is most likely the result of amplification from two adaptors.

The 1800 bp and 3000 bp products were cloned into pCR2.1-TOPO. Nine clones of the 1800 bp ligation and seven clones of the 3000 bp ligation were isolated. Restriction mapping with EcoRI showed that of these, four 1800 bp clones and six 3000 bp clones had insert between the two EcoRI sites.

The resulting pCR2.1 clones with 1800 bp and 3000 bp inserts were partially sequenced using M13 universal and reverse sequencing primers specific for pCR2.1-TOPO. Downstream sequences for the 1800 bp and 3000 bp clones were compared to the published part of the RSus3 sequence (Huang et al. 1996 (GenBank accession number: L03366)] using the alignment feature in the Winseq program.

All four 1800 bp clones were shown to have the upstream part of transcribed region of RSus3 inserted (two clones of each orientation). These clones were named pSsp A2, K1, K3 and K4.

Four 3000 bp clones were also shown to have the upstream part of the transcribed region of RSus3 inserted (with both orientations represented). These clones were named pSca K3, K5, New1 and New5.

Figure 1:
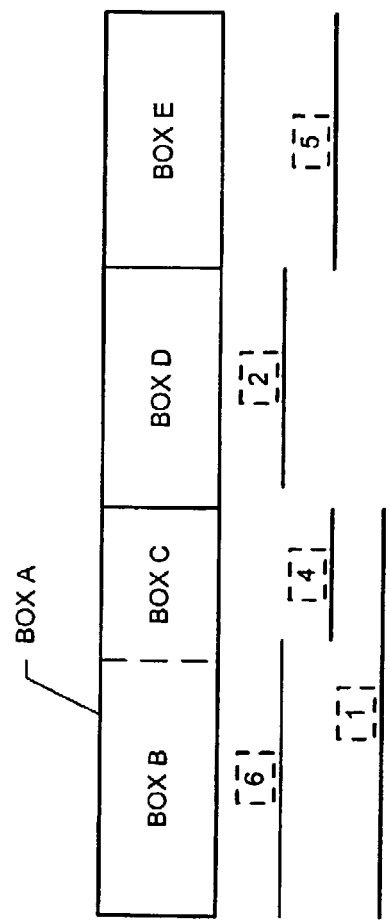
Figure 2:
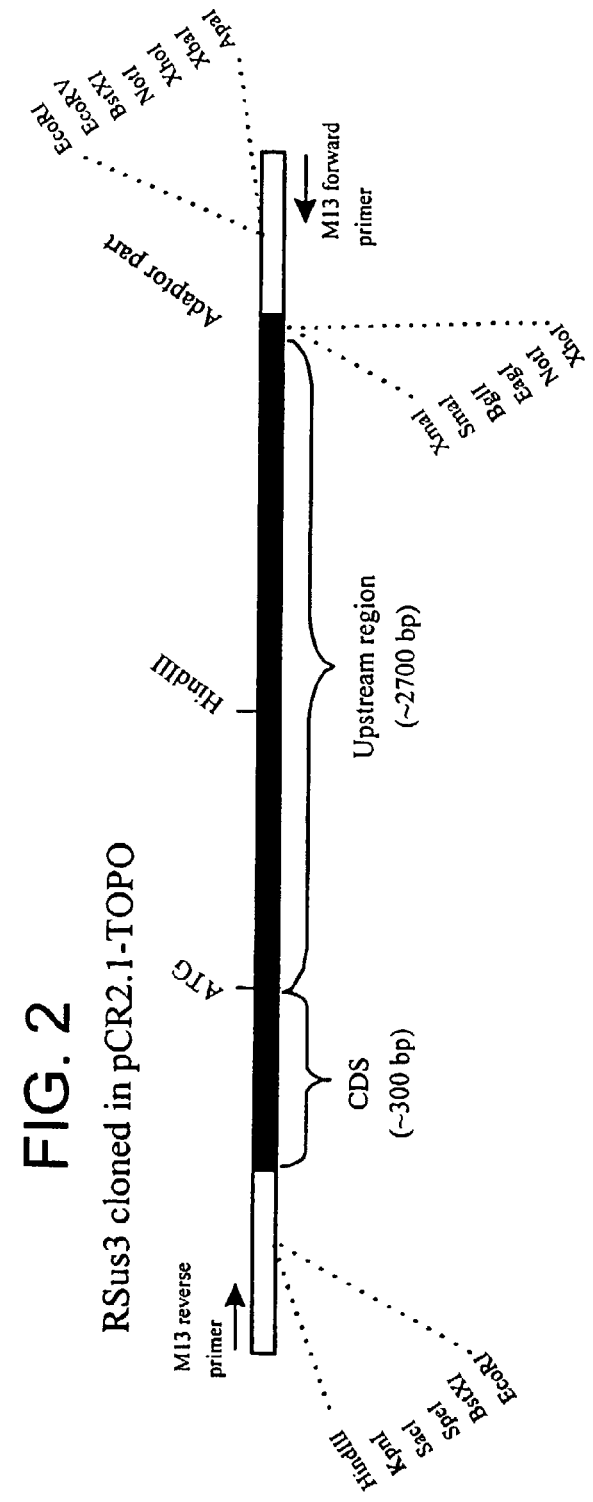

See FIG. 2.

Presentation of Sequence Data

The clone pTBR-ScaK3 (pScaK3) was chosen for total sequencing of the RSus3 promoter region. This clone was sequenced on both strands after the sequencing plan outlined in FIG. 12.

The other positive RSus3 clones described above was partially sequenced. The sequencing of the RSus3 clones resulted in determination of 2700 bp upstream the ATG codon (see SEQ ID No. 1).

DNA Sequence Analysis

The sequence for the RSus3 promoter region was analysed for the presence of putative cis-elements involved in the regulation of gene expression. The region upstream of the translational start codon was examined for the conserved TATA and CAAT consensus sequences, and the region was examined for the presence of putative endosperm or seed specific elements.

Additionally the region between the TATA box and the translational start codon was examined for the presence of intron donor and acceptor splice sites.

The translational start codon was chosen as basis for assigning bases in the RSus3 promoter, i.e. the A in ATG was numbered +1 (E.g. the base-pairs around the CAATGG are numbered −2, −1, +1, +2, +3 and +4).

Alignment of the RSus3 promoter region, with the promoter region region from RSus1 (GenBank accession number: X59046) and from RSus2 (GenBank accession number: X64770), gave no obvious similarity.

The results of the DNA sequence analysis are summarised in Table 1 (see earlier). The GCN4 box and the three endosperm boxes are cis-elements involved in endosperm specificity and the legumin boxes are cis-elements involved in seed specificity. Additionally the −1072 bp endosperm box and the GCN4 motif constitutes a putative prolamin element, which also is involved in endosperm specificity, although the distance between the endosperm box and GCN4 motifs in RSus3 is greater than this (34 bp), the sequence shows high similarity to the consensus sequence.

The GCN4 box, the two endosperm boxes and the majority of the legumin boxes are located within 700 bp spanning from −1023 bp to −1707 bp. This 700 bp sequence are located just upstream the TATA box.

A restriction map of the RSus3 promoter region is presented herein as FIG. 3.

Presentation of RSus3/GUS/NOSt Constructs

In this study, various RSus3 promoter sequences were fused with the uidA gene for generation of a series of RSus3/GUS expression cassettes. Specific deletions of the RSus3 promoter were constructed in an attempt to identify those parts of the promoter that are involved in tissue-specificity. A series of tandem-repeat promoters were constructed in an attempt to enhance the promoter activity, and the intron 1 was removed from the promoter region, in order to establish whether it is necessary for expression in guar endosperm.

The constructs were generated either by amplification of specific fragments by PCR or by subcloning. For verification of the resulting constructs, control restriction digests, typically with HindIII, Nhe I, and NcoI were performed. Additionally, control PCR or sequencing reactions were performed in some cases.

Common features in all variants of the RSus3 promoter were, translational fusion to the uidA gene, presence of the TATA box, and conservation of region downstream of this (with the exception of the single construct from which the intron was removed). The series of RSus3 promoter constructs centred around the upstream 700 bp region distal to the TATA box. As described above, this sequence contains the majority of putative cis-elements involved in specificity.

The various RSus3 promoter constructs are summarised in FIG. 13.

p2700 Construct (Plasmid Size 7938 bp)

An RSus3 promoter of 2700 bp was initially constructed. This construct constituted the full-length RSus3 promoter, and was prepared by amplification of a 2700 bp XhoI/NcoI fragment from pTBR-ScaK3 into SalI/NcoI in pGUSNOSt. Positive clones were verified by NcoI/HindIII digests, which resulted in 2 specific fragments, of 1160 bp and 1540 bp, in addition to the 5230 bp NcoI/HindIII fragment from the pGUSNOSt part.

p1730 Construct (Plasmid Size 6963 bp)

This 5' truncation of RSus3 was constructed by generation of a 571 bp NheI/HindIII fragment spanning from −1160 bp to −1730 bp. After changing of the upstream HindIII site to a NheI site in p2700, the NheI/HindIII fragment generated was subcloned into this p2700(upNheI). Positive clones were identified by an NheI/HindIII control digest, and this resulted in a specific fragment of same size as the subcloned fragment.

p1670 Construct (Plasmid Size 6907 bp)

This 5' truncation was analogous to p1730, comprising a 515 bp instead of 571 bp NheI/HindIII fragment, positive clones of which were identified in the same way.

p1560 Construct (Plasmid Size 6791 bp)

This 5' truncations was also analogous to p1730, comprising a 400 bp instead of 571 bp NheI/HindIII fragment, positive clones of which were identified in the same way.

p1450 Construct (Plasmid Size 6704 bp)

This construct was analogues to p2700, with ligation of a 1450 bp XhoI/NcoI fragment amplified from pSspK3 template, instead of the same amplified from pScaK3. A NcoI/HindIII digest resulted in two specific bands of 1160 bp and 290 bp, besides the 5230 bp pGUSNOSt fragment.

p1160 Construct (Plasmid Size 6390 bp)

This truncated promoter constitutes removal of 1540 bp upstream the internal HindIII site, and was generated by cutting p2700 with HindIII, followed by religation. Positive clones were identified by HindIII digest, which gave a single fragment in positive clones.

p2700-Prolamin Construct (Plasmid Size 7777 bp)

This internal truncation of 161 bp was produced by amplification of a 1020 bp fragment comprising the TATA box to the ATG codon. This fragment was cloned in p2700 (upNheI) as a HindIII/NcoI fragment. Positive clones were verified by a HindIII/NcoI digest, which resulted in a specific fragment of 1000 bp and a fragment of 6770 bp.

p1450-Intron (Plasmid Size 5837 bp)

In this construct, the intron 1 was removed by exactly splicing of the putative intron 1 acceptor and donor splice sites. This internal deletion of the intron 1 was generated by amplification of a region of p1450 which corresponded to RSus3 lacking the intron 1. After cloning in pCR2.1-TOPO, an XhoI/NcoI fragment containing this was subcloned in in pGUSNOSt. A positive clone was identified by restriction digestion with HindIII/NcoI, and the 3' promoter end was verified by sequencing.

pTandem Legumin (Plasmid Size 7536 bp)

This tandem repeat promoter was constructed by generation of a 570 bp NheI fragment spanning from −1160 bp to −1730 bp by PCR. This fragment was subcloned in the NheI site in p1730. A positive clone was identified by control digests and a control PCR reaction with Nhedel1/Dellow1 verified the orientation. The right orientation resulted in two bands of 650 bp and 1300 bp, whereas the reverse orientation only resulted in a 650 bp product.

pTandem Leg/Pro (Plasmid Size 7704 bp)

This tandem-repeat promoter was constructed by PCR amplifaction of a 740 bp NheI fragment spanning form −990 bp to −1730 bp. This fragment was subcloned in the NheI site in p1730. Positive clones were first identified by an Nhe I digest, and those of appropriate orientation were determined by HindIII digest. This was possible due to the internal HindIII site in the promoter, which was duplicated in this construct. Correct orientation resulted in a 740 bp HindIII fragment, whereas the reverse orientation resulted in a 1140 bp HindIII fragment.

pTandem Prolamin (Plasmid Size 7135 bp)

This tandem-repeat promoters was constructed by generation of a 170 bp HindIII fragment, spanning from −990 to −1160 bp by PCR, which was subcloned in the HindIII site in p1730. A Positive clone were identified by control digests, and the right orientation was determined by control PCR. Amplification with primer pair Nhedel1/HindGCN4 resulted in two bands of 600 bp and 750 bp for clones with right orientation, and to bands for of 300 bp and 750 bp for clones of reverse orientation.

See FIG. 15.

Transient Expression Experiments

The RSus3 expression cassettes described above were used to effect a transient transformation of guar tissue using the particle bombardment technique.

These experiments served several purposes. Firstly, for testing the usefulness of the method for generation of transient transformed guar tissue. Secondly, the purpose was to set up and optimise the Particle Inflow Gun (PIG) in Danisco Biotechnology, Holeby. Finally, the main purpose was to evaluate the strength and specificity of promoters, such as RSus3, in guar tissues.

Control

By way of a control experiment, a control plasmid comprising the uidA gene fused to the ENOS promoter was constructed. It is known that the ENOS promoter has high levels of expression in both endosperm and leaf tissue.

Transient Expression of RSus3/GUS/NOSt in Guar Tissue

A total of 11 sets of particle bombardment experiments were performed for testing the promoter strength and specificity of the RSus3 promoter region. The above described RSus3/GUS/NOSt constructions had been tested in this period. The procedures for the bombardment, for the preparation of guar tissue and for the coating of gold particles are described above.

The first approach was to test whether the RSus3 promoter was active in guar endosperm or not. p2700 and p1450 were bombarded into guar endosperms, and the result showed significant expression of GUS in endosperm for both constructs, although the expression was lower than for the ENOS control. These results were so promising that the subsequent work was concentrated around this promoter.

The second approach was to test whether the RSus3 was specific for the endosperm or whether it had expression in other parts of the plant. The initial experiment, which was performed on cotyledons from in vitro grown seedlings, showed differences in expression between p2700 and p1450. p2700 had almost no expression of GUS in cotyledons, whereas some cotyledons transformed with p1450 displayed significantly higher expression.

To test whether this expression pattern for p2700 and p1450 was the same in leaves, these constructs were also used to perform transient transformation of juvenile leaves from mature plants. This transformation turned out to be difficult due to severe damage of the leaf tissue caused by the helium blast. Not only was the expression of RSus3 concentrated in the vascular tissue of the leaves, but also the ENOS control showed same expression pattern indicating that optimisation of the procedure for leaves were necessary. Due to limitations in time, however, these optimisation experiments were abolished after a while, and instead it was chosen exclusively to bombard cotyledons from seedlings and from seeds.

The transient GUS expression, directed by the two RSus3 promoter constructs, p2700 and p1450, justified further analysis of the promoter strength and tissue specificity. As described above a series of deletions of the RSus3 promoter were constructed and these were tested in guar endosperm, guar embryo cotyledons and cotyledons from 12 and 20 day old seedlings. Additionally, in an attempt to enhance the promoter activity, 3 tandem promoters were constructed and the resulting constructs were also tested in same tissue for evaluation of promoter strength and specificity.

FIG. 16 presents transient GUS expression data from the control ENOS promoter, the RSus3 promoter construct p1730 and the RSus3 promoter construct pTandem leg/pro (tandem repeat). The results, which are in accordance with the findings for the other RSus3 promoter constructs, have been discussed above. These results show selective endosperm expression of an NOI.

The results of transient GUS expression in guar endosperms, after bombardment with RSus3 constructs, are summarised in FIG. 17.

The data show that the promoter of the present invention causes selective expression of the NOI in endosperm. In addition, a tandem repeat of the promoter of the present invention causes an increase in the expression levels.

As can be seen at FIG. 17 the expression in guar endosperm are only slightly affected by deletion of the sequence between 2700 bp and 1160 bp. The 1160 bp has still significant expression indicating that the cis-elements which caused the main part of expression in guar endosperm are present between 1160 bp and the TATA box (÷989 bp). This part has been removed in the p2700÷prolamin construct, and this result in a loss of 25% of the promoter activity compared to p2700.

pTandem leg/pro gives highest expression in endosperms, 3 times higher than the 2700 construct and the level of expression is comparable to NOS expression in endosperms.

No blue spots were observed when GUAR tissues were bombarded with microprojectiles treated in the same manner, only without DNA, and when the PIG was discharged without microprojectiles. Bombardment with the promoter-less GUS construct (pGUSNOSt) gave only a few blue spots, presumably caused by illegitimate recombination into the chromosome adjacent to a promoter.

For comparative analysis of expression in endosperms versus cotyledons, values relative to the area of the bombarded tissue were calculated. An average 4 weeks old endosperm comprises an area of 0.2 $cm^2$, and the same for an average pre-emerged cotyledon. An average 12 days cotyledon covers an area of 1.5 $cm^2$, and an average 20 days cotyledon an area of 2.8 $cm^2$. Therefore the number of blue spots per 12 day or 20 days cotyledon were corrected to number of blue spots per 0.2 $cm^2$.

FIG. 18 shows that the only highly significant change in promoter strength was displayed by the Tandem leg/pro variant. Although this construct directed a level of GUS expression which was three-fold larger than that of the parent construct p2700, it retained specificity for the endosperm. Levels of expression in cotyledons was equally low with the Tandem leg/pro variant as it was with p2700.

Co-Transformation

The largest component of variance in data obtained by measurements of transient gene expression, following ballistic transformation, resides in the differences in the efficiency of delivery of the DNA to the target. It has been shown that one can compensate for this problem, and obtain more precise evaluation of transient gene expression, by co-transformation with a control expression vector containing a different reporter gene (Godon, C., Caboche, M, Daniel-Vedele, F. (1993) Biochimie 75: 591–595). By measuring the reporter activities and expressing results as the ratio of the test activity to that of the control, fluctuations that merely result from differences in the amount of DNA striking the target are accounted for.

Figure 24:
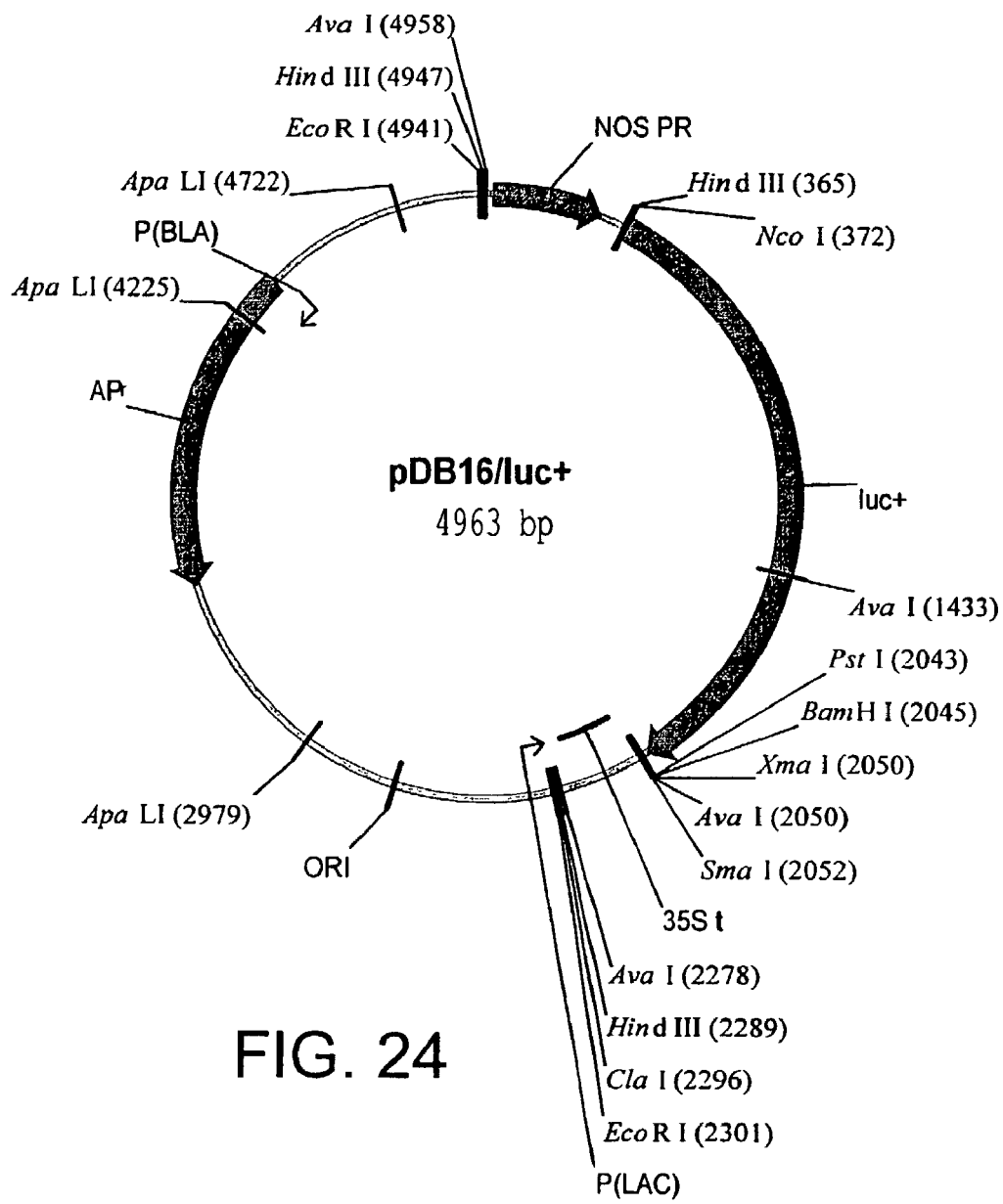
Figure 25:
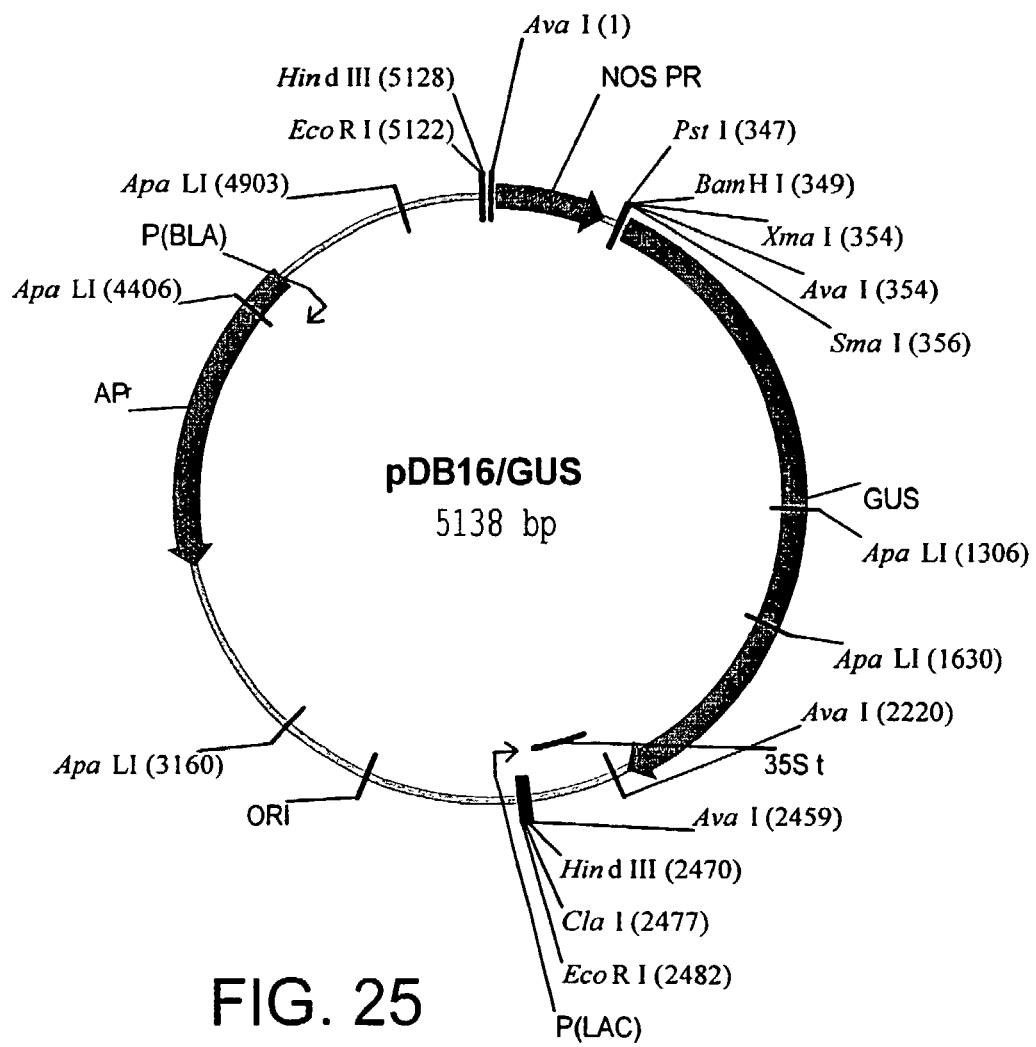

The RSus3 promoter variants, were also tested in this manner. The firefly luciferase gene (luc) was fused to each of them, as a reporter, and ballistic transformation was repeated as described before, but two control plasmids were included in equal molar amounts to the test plasmid. The strength and tissue-specificities of the different promoter constructs were tested in modified transient expression studies of ballistically transfomed endosperms, and pre-emerged cotyledons, from the same guar seeds. Each experiment involved simultaneous transformation with three separate plasmids. Of these, one was a test plasmid (p2700+intron/luc+, p2700−intron/luc+, pTandem leg/pro +intron/luc+, or pTandem leg/pro−intron/luc+ or pDB16/luc+), in which promoters were fused to the firefly luciferase gene (luc+) (FIGS. 19, 20, 21, 22, and 23). The remaining two were control plasmids, in which either the uidA (GUS) gene or the *renilla* luciferase gene (pDB16/Rluc) were under the control of the NOS promoter (FIGS. 24 and 25). 2 μg of test plasmid were mixed with 2 μg of each control plasmid, and coating of particles with this DNA, preparation, bombardment, and subsequent incubation of tissue, were all performed as described above.

Enzyme extracts of bombarded tissues were made by grinding these in liquid nitrogen, and extracting the frozen macerate with a buffer containing boric acid, that prevents gelling of the galactomannan in cryopreserved material. Approximately 400 mg of each tissue were extracted with 800 μl of extraction buffer (50 mM $NaH_2PO_3$, 50 mM $H_3BO_3$, 1 mM dithiothreitol, 1 mM EDTA disodium salt, 10 mg/ml bovine serum albumin, pH was adjusted to 7.0 by addition of sodium hydroxide). Samples were centrifuged at 12,000 g, at 4° C., for 2 minutes, and the resulting supernatants were used for analysis.

The activities of all three reporter genes were measured luminometrically using a Turner TD-20/20 luminometer (Turner Designs, Sunnyvale, Calif., USA). The two luciferase acivities were measured sequentially in the same reaction mixture, after the 'Dual-Luciferase®' method described in Promega Technical Manual No. 40 (Promega Corporation, Madison, Wis., USA). 20 μl of guar tissue extract were rapidly mixed with 100 μl of LARII reagent in the apparatus, which after 2 seconds measured and integrated the light evolved over the subsequent 10 seconds. Immediately after this, 100 μl of 'Stop and Glo®' reagent were added to the reaction mixture and the *renilla* luciferase luminescence was measured in the same manner.

GUS activity was measured according to the GUS-Light™ system instruction manual (TROPIX Inc., Bedford, Mass., USA). 20 μl of guar tissue extract were added to 180 μl of GUS reaction buffer, and incubated at 25° C. for one hour. The tube was placed in the luminometer, 300 μl of 'light emission accelerator' were added, and after 2 seconds the light emitted during the subsequent 10 seconds was measured and integrated.

The values obtained are summarised in the table below.

| | Relative Integrated Light Signal | | | | | |
|---|---|---|---|---|---|---|
| | Dual Luciferase ® Reporter Assay system (Promega) | | | | GUS-Light ™ (Tropix) | |
| | Endosperm | | Cotyledon | | Endosperm | Cotyledon |
| Rsus3/luciferase experiment | luc+ | Rluc | luc+ | Rluc | GUS | GUS |
| p2700 + intron/luc+ | 7.7 | 352.0 | 1.2 | 248.7 | 194.5 | 208.2 |
| (pDB16/Rluc and pDB16/GUS) | 7.6 | 350.4 | 0.8 | 236.4 | 165.3 | 192.4 |
| | 7.6 | 353.2 | 0.8 | 256.7 | 189.8 | 206.7 |
| P2700 − intron/luc+ | 20.9 | 574.0 | 0.6 | 185.2 | 269.7 | 215.0 |
| (pDB16/Rluc and pDB16/GUS) | 20.9 | 585.1 | 0.5 | 179.3 | 252.1 | 151.3 |
| | 21.2 | 596.7 | 0.5 | 195.1 | | 228.0 |
| PTandem (leg/pro) + intron/luc+ | 13.9 | 249.5 | 1.1 | 209.2 | 93.4 | 166.4 |
| (pDB16/Rluc and pDB16/GUS) | 13.3 | 248.8 | 0.9 | 202.3 | 99.6 | 142.0 |
| | 13.3 | 247.5 | 0.8 | 206.6 | 104.9 | 182.7 |
| pTandem (leg/pro) − intron/luc+ | 42.8 | 570.1 | 1.7 | 205.1 | 249.2 | 172.3 |
| (pDB16/Rluc and pDB16/GUS) | 43.2 | 591.8 | 1.5 | 202.6 | 225.2 | 156.3 |
| | 44.7 | 604.3 | 1.5 | 213.9 | | 167.2 |
| pDB16/luc+ | 45.3 | 565.5 | 22.3 | 155.5 | 289.8 | 206.6 |
| (pDB16/Rluc and pDB16/GUS) | 43.4 | 582.0 | 21.4 | 176.2 | 205.8 | 191.8 |
| | 45.1 | 623.4 | 19.9 | 172.4 | 333.2 | 206.4 |

Figure 26:
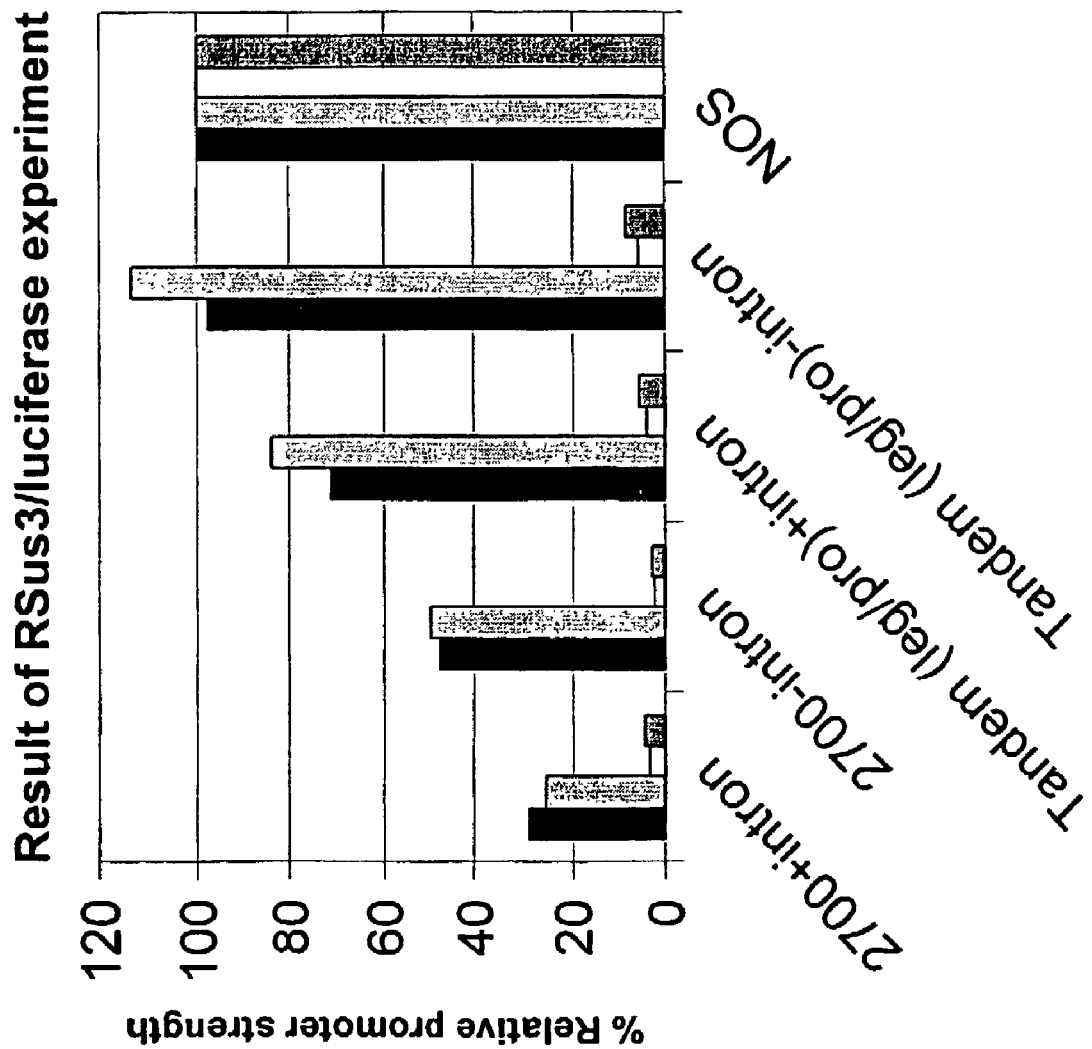

The same results are expressed in FIG. 26 as 'relative strength of promoter', the value of which is calculated by the division of two ratios, the test ratio and the control ratio. The test ratio was calculated by dividing the luminescence generated by the firefly luciferase, under control of test promoter construct, by the value obtained from the control reporter gene (either uidA or Rluc) under the control of the NOS promoter. The control ratio was calculated by dividing the luminescence from the firefly luciferase by the value from the control reporter gene (either uidA or Rluc) when both genes were under the control of the NOS promoter. 'Relative strength of promoter' was calculated by dividing the test ratio by the control ratio and multiplying the value obtained by one hundred.

The results in FIG. 26 show a pattern that mirrors that shown in FIG. 17 insofar as the Tandem leg/pro configuration enhances the activity of the promoter while retaining tissue specificity. Although it appeared from the earlier results that the Tandem leg/pro promoter construct was twice as strong as the NOS promoter strength in endosperm tissue, the results in FIG. 26 show that these two promoters in fact display similar strength in this tissue. These results also show that removal of the intron from constructs seems to enhance promoter strength in guar tissue. This is a preferred aspect for some embodiments of the present invention. Hence, preferably the NOI does not comprise an intron.

SUMMARY

In summation, the present invention relates to a promoter and, also to a construct comprising the same. In particular the present invention relates to the use of a promoter for the expression of a NOI in an organism.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

Bloomfield V A (1991) Condensation of DNA by multivalent Cations: Considerations on Mechanism Biopolymers 31: 1471–1481

Donovan C R & Lee J W (1977) The Growth of Detached Wheat Heads in Liquid Culture Plant Science Letters 9: 107–113

Kikkert J R (1993) The Biolistic PDS-1000/He device Plant cell, Tissue and Organ Culture 33: 221–226

Knudsen S & Müller M (1991) Transformation of the developing barley endosperm by particle bombardment Planta 185: 330–336

Siebert PD, Chenchik A, Kellogg D E, Lukyanov K A and Lukyanov SA (1995) An improved PCR method for walking in uncloned genomic DNA Nucleic Acids Research, vol. 23, no.6; p. 1087–1088

Huang JW, Chen J T, Yu W P, Shyur L F, Wang A Y, Sung H Y, Lee P D and Su (1996) Complete Structures of Three Rice Sucrose Synthase Isogenes and Differential Regulation of Their Expressions Biosci. Biotech. Biochem. 60(2): p233–239

Copeland L (1990) Methods in plant biochemistry Vol. 3, Kap. 4: Enzymes of Sucrose Metabolism Academic Press Limited Dörmann P & Benning C (1998) The role of UDP-glucose epimerase in carbohydrate metabolism of Arabidobsis The Plant Journal 13(5): 641–652

Finer J J, Vain P, Jones M W & McMullen M D (1992) Development of the particle inflow gun for DNA delivery to plant cells Plant cell Reports 11: 323–328

Jefferson R A (1987) Assaying Chimeric Genes in Plant: The GUS Gene Fusion System Plant Molecular Biology Reporter vol. 5, number 4

Karrer E E & Rodriquez R L (1992) Metabolic regulation of rice alpha-amylase and sucrose synthase genes in planta Plant J 2(4): 517–523

Klein T M, Wolf E D, Wu R & Sanford J C (1987) High-velocity microprojectiles for delivery nucleic acids into living cells Nature 327: 70–73

Klein T M, Fromm M, Weissinger A, Tomes D, Schaaf S, Sletten M & Sanford J C (1988) Transfer of foreign genes into intact maize cells with high-velocity microprojectiles Proc. Natl. Acad. Sci. USA 85: 4305–4309

Lopes M A & Larkin B A (1993) Endosperm origin, development, and function The Plant Cell 5: 1383–1399

Sanford J C, Klein T M, Wolf E D & Allen N (1987) Delivery of substances into cells and tissues using a particle bombardment process Particulate Science and Technology 5: 27–37

Thomas T L (1993) Gene expression during plant embryogenesis and germination: An overview The Plant Cell 5: 1401–1410

Vain P, Keen N, Murillo J, Rathus C, Nemes C & Finer J J (1993) Development of the Particle Inflow Gun Plant cell, Tissue and Organ Culture 33: 237–246

West M A L & Harada J J (1993) Embryogenesis in higher plants: An overview The Plant Cell 5: 1361–1369

Whistler R L & Hymowitz T (1979) GUAR:Agronomy, Production, Industrial use and Nutrition Purdue University Press, West Lafayette, Ind.

REFERENCES FOR TABLE 1

Bäumlein H, Nagy I, Villarroel R, Inzé D & Wobus U (1992) Cis-analysis of a seed protein gene promoter: the conservative RY-repeat CATGCATG within the legumin box is essential for tissue-specific expression of a legumin gene The Plant Journal 2(2): 233–239

Joshi C P (1987) An inspection of the domain between putative TATA box and translation start site 79 plant genes Nuc. Acid. Res. 15(16): 6643–6653

Marzabal P, Busk P K, Ludevid M D & Torrent M (1998) The bifactorial endosperm box of gamma-zein gene: characterisation and function of the Pb3 and GZM cis-acting elements. The Plant Journal 16(1): 41–52

Müller M & Knudsen S (1993) The nitrogen response of a barley C-hordein promoter is controlled by positive and negative regulation of the GCN4 and endosperm box The Plant Journal 4(2): 343–355

Simpson C G & Filipowicz W (1996) Splicing of precursors to mRNA in higher plants: mechanism, regulation and sub-nuclear organisation of the spliceosomal machinery Plant Molecular Biology 32: 1–41

The invention claimed is:

1. An isolated promoter comprising a nucleotide sequence corresponding to that shown as SEQ ID No. 6.

2. An isolated promoter having a nucleotide sequence corresponding to that shown as SEQ ID No. 6.

3. An isolated promoter comprising a nucleotide sequence corresponding to that shown in SEQ ID No. 1.

4. An isolated promoter having a nucleotide sequence corresponding to that shown in SEQ ID No. 1.

5. A promoter according to claim 1, wherein the promoter is obtained from a plant of the genus *Oryza*.

6. A promoter according to claim 1, wherein the promoter is operably linked to a nucleotide sequence of interest.

7. A promoter according to claim 3, wherein the promoter is linked to the sequence presented as SEQ ID No. 2, or a nucleotide sequence with at least 95% homology to SEQ ID No. 2.

8. A promoter according to claim 7, wherein if a nucleotide sequence of interest is operably linked to the promoter then the sequence presented as SEQ ID No. 2, or a nucleotide sequence with at least 95% homology to SEQ ID No. 2, is located intermediate the promoter and the nucleotide sequence of interest.

9. A promoter according to claim 1, wherein the promoter is linked to the sequence presented as SEQ ID No. 5.

10. A promoter according to claim 9, wherein if a nucleotide sequence of interest is operably linked to the promoter then the sequence presented as SEQ ID No. 5 is located intermediate the promoter and the nucleotide sequence of interest.

11. A construct comprising the promoter according to claim 1, wherein the promoter is operably linked to a nucleotide sequence of interest.

12. An expression vector comprising the promoter according to claim 1.

13. A transformation vector comprising the promoter according to claim 1.

14. A transformed host or host cell comprising the promoter according to claim 1.

15. A transformed host or host cell according to claim 14, wherein the host or host cell is a plant or a plant cell.

16. A method of preparing a protein of interest, the method comprising expressing a nucleotide sequence of interest which encodes at least a part of the protein of interest, wherein the nucleotide sequence of interest is operably linked to the promoter according to claim 1, optionally isolating the expression product of the nucleotide sequence of interest, forming the protein of interest if the expression product of the nucleotide sequence of interest is not all of the protein of interest, optionally isolating the protein of interest.

17. A method according to claim 16 wherein the nucleotide sequence of interest codes for all of the protein of interest.

18. A method for expressing a nucleotide sequence of interest in endosperm, the method comprising expressing in endosperm the nucleotide sequence of interest operably linked to the promoter according to claim 1, wherein the endosperm is transgenic for the nucleotide sequence of interest operably linked to the promoter according to claim 1.

19. An isolated promoter sequence obtained from Deposit No. NCIMB 41011.

20. The promoter of claim 3, wherein the promoter is linked to the sequence presented as SEQ ID No. 2, or a nucleotide sequence with at least 98% homology to SEQ ID No. 2.

21. The promoter of claim 1, wherein the promoter is linked to the sequence presented as SEQ ID No. 4.

22. The promoter of claim 1, wherein the promoter is linked to the sequence presented as SEQ ID No. 2, or a nucleotide sequence with at least 95% homology to SEQ ID No. 2.

23. The promoter of claim 1, wherein the promoter is linked to the sequence presented as SEQ ID No. 2, or a nucleotide sequence with at least 98% homology to SEQ ID No. 2.

24. The promoter of claim 21, wherein the promoter is linked to the sequence presented as SEQ ID No. 2, or a nucleotide sequence with at least 95% homology to SEQ ID No. 2.

25. The promoter of claim 21, wherein the promoter is linked to the sequence presented as SEQ ID No. 2, or a nucleotide sequence with at least 98% homology to SEQ ID No. 2.

26. The promoter of claim 1, wherein the promoter is linked to the sequence presented as SEQ ID No. 5.

27. The promoter of claim 21, wherein the promoter is linked to the sequence presented as SEQ ID No. 5.

28. The promoter of claim 22, wherein the promoter is linked to the sequence presented as SEQ ID No. 5.

29. The promoter of claim 23, wherein the promoter is linked to the sequence presented as SEQ ID No. 5.

30. The promoter of claim 24, wherein the promoter is linked to the sequence presented as SEQ ID No. 5.

31. The promoter of claim 25, wherein the promoter is linked to the sequence presented as SEQ ID No. 5.

* * * * *

SEQUENCE LISTING

<160> NUMBER OF SEQ ID NOS: 43

<210> SEQ ID NO 1
<211> LENGTH: 1772

```
<212> TYPE: DNA
<213> ORGANISM: Artificial Sequence
<220> FEATURE:
<223> OTHER INFORMATION: Description of Artificial Sequence: Synthetic
      promoter sequence

<400> SEQUENCE: 1
actttagata ataaagtaag tcacaagaaa aataaataat aattccaaat ttttttaata      60
agacgagtgg tcaaacagta caagtaaaaa ctcaaaattc cttatattat gggacttata     120
ttatgggacg gaggaagtag aagattgtag ccaagaaaaa aacaaaaaca aacacaccgc     180
cacctggcag gcatgcatct taggtcggca cattgagagg tcggcagtag acgagttacc     240
ctacacaact gcttcttcag tgagctagct gcatgttctg ttctgcattt acattgcagg     300
cagcagctag caacagtttg caggaacaat cgataatcca ttgtgtcagg gaggaacatg     360
gagaaaaacc ggggctggag acgaacggga gcagctgtac cgtacgtttc tgaaggctga     420
acccatctgc gaaatccgca gattggtttg ttcaattcca acttgcagtc cttcagattg     480
gttgcatgtt caaccgtagt acatctgaaa aatgaagtgt taaataccct gagaagacct     540
tcatggaagc atgcctgcag gcgattagct aagaaaaaaa aaataaatgt acttttcgaa     600
acttaatttt ggagttagat tttagggtgt ttccatcgta gtgtattttc tactattgca     660
gtttaaaccg ctaatagtca gatataaaat tttatctata gatcatttat aaatcatttt     720
tagttgcttc gttcattttt ctaccactta tcaaccatag ctcaactgat caattgacaa     780
taaaagttac taaacgacat cgctcatcac acacccaacg ctcaccgatg ggtgcctctc     840
gaccacgagt ttagcacttg tgcaacatat atgcgtgcga tgaacatcta ctgatgcgcc     900
atgcgaattt tagcgttcgt tcatgacgct tccaacggca cagaggctga gcagcagcat     960
gcatgcatgg ctcttgtgaa aacaaaaaag gttactggta aatgacatgc tgctgtagct    1020
agttagcaga atgcaaggcc catgcatatg caatgctatg caacaagtat agtaccagca    1080
tgtatggtag ccagctaact aatctatcag cagaggcagc aagctcgtgc atggtgtgat    1140
gcacttctct ccagtaatct agtggtaatt ttcacccaaa gcgttgctca tatggacagt    1200
aattagtaat attaccaagg ttcacaatcc cgttacctga ccaaatacta ctcacgaatg    1260
gtatctctgg ttttcgttaa aaccgttggt aaaccagcaa aaatagacaa aatttgtcaa    1320
aattttaaat tttagttttt tttttaactt agccgggaaa ccttgaagtt tgtgctgtcg    1380
agctgtcctg ggaaggacgg ttttggttgg gattgtgaac cctggttact gcacttcatt    1440
tttgaacaga tattagtgca acagacaaat gccaacgcat ttttttctgt ttaccggcaa    1500
gctgaagctt ttacgatccc cataccgccg ttgctgcaaa cctgccaaga aagagcagca    1560
gaaacaggtg tcattttgtg gtggaaagcc aagtaaagta aacagaagat ggaagatagt    1620
gaggaccagg gagtgaggca ggggacacat ggcccacgcc tccctgcaca ttttcgtgta    1680
taaatacagg tggatgcatc gctctcccag catccatcgg ttctctgctc tgttcatcca    1740
tagagtttcc tcctcttctc cttcagtgca ag                                  1772

<210> SEQ ID NO 2
<211> LENGTH: 865
<212> TYPE: DNA
<213> ORGANISM: Artificial Sequence
<220> FEATURE:
<223> OTHER INFORMATION: Description of Artificial Sequence: Synthetic
      intron nucleotide sequence

<400> SEQUENCE: 2
```

-continued

```
gtagagaaga gcatgtgtgt gtgtgtgtgt gaactgtgaa gtgcagagtg cttctgtagt      60
tctgtgttat gtccatagtg atcttgttag gattgttgct atggatgcat gatgttatgg     120
ttaatctctg aattacagta gggacttctc tgagatctct ggattagtgg ggggtgctaa     180 attttttttct ggttgcatca gcttgggttt ctgggattgg tgtgggttct tgctctgaat   240
tttggttcag aatgtcgatt tgttttgtgt ttgccctctg aagttgagag tagctatgat    300
ccatccagca cagaactgca ggtccctgcc tgccggcagc atatacagga catgccattt    360
tgcaagctct gggcttatgg tttctctttt ggagttcttc ttcttgcatg atctgtgttc    420
tctaacaaag aagcaagatt tagcaacttt attcagagac aagaaaagga tctggcaacc    480
ttttgtttct gttttatcct actcgtaaag attgttattt aagcaaaaat ttcccaaaag    540
ttttaaatat aatttccatg atgtgccact ctcatgtcct tgaacctggc actcattatg    600
ggctcctcag aagtgctgta gctaatgtca ctaatctttt gtatctttgt tcgtagtctt    660 gtatttatg atgcttatcc ctttgtgctt tccatgtttg atgtccaaat gtcatggcaa     720 tgttttttgac ttctagtagg ggttttagta ccttttttgtt agataagtac atccaaattc  780
tgtttattta ttcaaaaatc attctgttta ttcactgaaa acatttgtcc attcaatgga    840
atcgtaaact gtctgtgttt ttcag                                          865
```

<210> SEQ ID NO 3
<211> LENGTH: 1803
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 3

```
actttagata taaagtaag tcacaagaaa aataaataat aattccaaat ttttttaata      60
agacgagtgg tcaaacagta caagtaaaaa ctcaaaattc cttatattat gggacttata    120
ttatgggacg gaggaagtag aagattgtag ccaagaaaaa aacaaaaaca aacacaccgc    180
cacctggcag gcatgcatct taggtcggca cattgagagg tcggcagtag acgagttacc    240
ctacacaact gcttcttcag tgagctagct gcatgttctg ttctgcattt acattgcagg    300
cagcagctag caacagtttg caggaacaat cgataatcca ttgtgtcagg gaggaacatg    360
gagaaaaacc ggggctggag acgaacggga gcagctgtac cgtacgtttc tgaaggctga    420
acccatctgc gaaatccgca gattggtttg ttcaattcca acttgcagtc cttcagattg    480
gttgcatgtt caaccgtagt acatctgaaa atgaagtgt taaataccttt gagaagacct    540 tcatggaagc atgcctgcag gcgattagct aagaaaaaaa aaataaatgt acttttcgaa    600 acttaattttt ggagttagat tttagggtgt ttccatcgta gtgtattttc tactattgca   660
gtttaaaccg ctaatagtca gatataaaat tttatctata gatcatttat aaatcatttt    720
tagttgcttc gttcattttt ctaccactta tcaaccatag ctcaactgat caattgacaa    780
taaaagttac taaacgacat cgctcatcac acacccaacg ctcaccgatg ggtgcctctc    840
gaccacgagt ttagcacttg tgcaacatat atgcgtgcga tgaacatcta ctgatgcgcc    900
atgcgaattt tagcgttcgt tcatgacgct ccaacggca cagaggctga gcagcagcat     960
gcatgcatgg ctcttgtgaa aacaaaaaag gttactggta aatgacatgc tgctgtagct   1020
agttagcaga atgcaaggcc catgcatatg caatgctatg caacaagtat agtaccagca   1080
tgtatggtag ccagctaact aatctatcag cagaggcagc aagctcgtgc atggtgtgat   1140
```

```
gcacttctct ccagtaatct agtggtaatt ttcacccaaa gcgttgctca tatggacagt      1200
aattagtaat attaccaagg ttcacaatcc cgttacctga ccaaatacta ctcacgaatg      1260
gtatctctgg ttttcgttaa aaccgttggt aaaccagcaa aaatagacaa atttgtcaa       1320 aattttaaat tttagttttt tttttaactt agccgggaaa ccttgaagtt tgtgctgtcg      1380
agctgtcctg ggaaggacgg ttttggttgg gattgtgaac cctggttact gcacttcatt      1440
tttgaacaga tattagtgca acagacaaat gccaacgcat ttttttctgt ttaccggcaa      1500
gctgaagctt ttacgatccc cataccgccg ttgctgcaaa cctgccaaga aagagcagca      1560
gaaacaggtg tcattttgtg gtggaaagcc aagtaaagta aacagaagat ggaagatagt      1620
gaggaccagg gagtgaggca ggggacacat ggcccacgcc tccctgcaca ttttcgtgta      1680
taaatacagg tggatgcatc gctctcccag catccatcgg ttctctgctc tgttcatcca      1740
tagagtttcc tcctcttctc cttcagtgca aggcttgagg atccaactag aagatagcaa      1800
tgg                                                                    1803

<210> SEQ ID NO 4
<211> LENGTH: 86
<212> TYPE: DNA
<213> ORGANISM: Artificial Sequence
<220> FEATURE:
<223> OTHER INFORMATION: Description of Artificial Sequence: Synthetic
      exon nucleotide sequence

<400> SEQUENCE: 4
caggtggatg catcgctctc ccagcatcca tcggttctct gctctgttca tccatagagt       60
ttcctcctct tctccttcag tgcaag                                            86

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      exon nucleotide sequence

<400> SEQUENCE: 5
gcttgaggat ccaactagaa gatagcaatg g                                      31

<210> SEQ ID NO 6
<211> LENGTH: 1686
<212> TYPE: DNA
<213> ORGANISM: Artificial Sequence
<220> FEATURE:
<223> OTHER INFORMATION: Description of Artificial Sequence: Synthetic
      promoter sequence

<400> SEQUENCE: 6
actttagata taaagtaagt cacaagaaaa ataaataat aattccaaat ttttttaata        60
agacgagtgg tcaaacagta caagtaaaaa ctcaaaattc cttatattat gggacttata      120
ttatgggacg gaggaagtag aagattgtag ccaagaaaaa aacaaaaaca aacacaccgc      180
cacctggcag gcatgcatct taggtcggca cattgagagg tcggcagtag acgagttacc      240
ctacacaact gcttcttcag tgagctagct gcatgttctg ttctgcattt acattgcagg      300
cagcagctag caacagtttg caggaacaat cgataatcca ttgtgtcagg gaggaacatg      360
gagaaaaacc ggggctggag acgaacggga gcagctgtac cgtacgtttc tgaaggctga      420
acccatctgc gaaatccgca gattggtttg ttcaattcca acttgcagtc cttcagattg      480
```

-continued

```
gttgcatgtt caaccgtagt acatctgaaa aatgaagtgt taaataccct gagaagacct    540
tcatggaagc atgcctgcag gcgattagct aagaaaaaaa aaataaatgt acttttcgaa    600
acttaatttt ggagttagat tttagggtgt ttccatcgta gtgtattttc tactattgca    660
gtttaaaccg ctaatagtca gatataaaat tttatctata gatcatttat aaatcatttt    720
tagttgcttc gttcattttt ctaccactta tcaaccatag ctcaactgat caattgacaa    780
taaaagttac taaacgacat cgctcatcac acacccaacg ctcaccgatg ggtgcctctc    840
gaccacgagt ttagcacttg tgcaacatat atgcgtgcga tgaacatcta ctgatgcgcc    900
atgcgaattt tagcgttcgt tcatgacgct tccaacggca cagaggctga gcagcagcat    960
gcatgcatgg ctcttgtgaa aacaaaaaag gttactggta aatgacatgc tgctgtagct   1020
agttagcaga atgcaaggcc catgcatatg caatgctatg caacaagtat agtaccagca   1080
tgtatggtag ccagctaact aatctatcag cagaggcagc aagctcgtgc atggtgtgat   1140
gcacttctct ccagtaatct agtggtaatt ttcacccaaa gcgttgctca tatggacagt   1200
aattagtaat attaccaagg ttcacaatcc cgttacctga ccaaatacta ctcacgaatg   1260
gtatctctgg ttttcgttaa aaccgttggt aaaccagcaa aaatagacaa aatttgtcaa   1320
aattttaaat tttagttttt tttttaactt agccgggaaa ccttgaagtt tgtgctgtcg   1380
agctgtcctg ggaaggacgg ttttggttgg gattgtgaac cctggttact gcacttcatt   1440
tttgaacaga tattagtgca acagacaaat gccaacgcat ttttttctgt ttaccggcaa   1500
gctgaagctt ttacgatccc cataccgccg ttgctgcaaa cctgccaaga aagagcagca   1560
gaaacaggtg tcattttgtg gtggaaagcc aagtaaagta aacagaagat ggaagatagt   1620
gaggaccagg gagtgaggca ggggacacat ggcccacgcc tccctgcaca ttttcgtgta   1680
taaata                                                                1686
```

<210> SEQ ID NO 7
<211> LENGTH: 2668
<212> TYPE: DNA
<213> ORGANISM: Artificial Sequence
<220> FEATURE:
<223> OTHER INFORMATION: Description of Artificial Sequence: Synthetic promoter sequence of the present invention

<400> SEQUENCE: 7

```
actttagata ataaagtaag tcacaagaaa aataaataat aattccaaat ttttttaata     60
agacgagtgg tcaaacagta caagtaaaaa ctcaaaattc cttatattat gggacttata    120
ttatgggacg gaggaagtag aagattgtag ccaagaaaaa aacaaaaaca aacacaccgc    180
cacctggcag gcatgcatct taggtcggca cattgagagg tcggcagtag acgagttacc    240
ctacacaact gcttcttcag tgagctagct gcatgttctg ttctgcattt acattgcagg    300
cagcagctag caacagtttg caggaacaat cgataatcca ttgtgtcagg gaggaacatg    360
gagaaaaacc ggggctggag acgaacggga gcagctgtac cgtacgtttc tgaaggctga    420
acccatctgc gaaatccgca gattggtttg ttcaattcca acttgcagtc cttcagattg    480
gttgcatgtt caaccgtagt acatctgaaa atgaagtgt taaataccct gagaagacct     540
tcatggaagc atgcctgcag gcgattagct aagaaaaaaa aaataaatgt acttttcgaa    600
acttaatttt ggagttagat tttagggtgt ttccatcgta gtgtattttc tactattgca    660
gtttaaaccg ctaatagtca gatataaaat tttatctata gatcatttat aaatcatttt    720
tagttgcttc gttcattttt ctaccactta tcaaccatag ctcaactgat caattgacaa    780
```

```
taaaagttac taaacgacat cgctcatcac acacccaacg ctcaccgatg ggtgcctctc    840
gaccacgagt ttagcacttg tgcaacatat atgcgtgcga tgaacatcta ctgatgcgcc    900
atgcgaattt tagcgttcgt tcatgacgct tccaacggca cagaggctga gcagcagcat    960
gcatgcatgg ctcttgtgaa aacaaaaaag gttactggta aatgacatgc tgctgtagct   1020
agttagcaga atgcaaggcc catgcatatg caatgctatg caacaagtat agtaccagca   1080
tgtatggtag ccagctaact aatctatcag cagaggcagc aagctcgtgc atggtgtgat   1140
gcacttctct ccagtaatct agtggtaatt ttcacccaaa gcgttgctca tatggacagt   1200
aattagtaat attaccaagg ttcacaatcc cgttacctga ccaaatacta ctcacgaatg   1260
gtatctctgg ttttcgttaa aaccgttggt aaaccagcaa aaatagacaa atttgtcaa    1320 aattttaaat tttagttttt tttttaactt agccgggaaa ccttgaagtt tgtgctgtcg   1380
agctgtcctg ggaaggacgg ttttggttgg gattgtgaac cctggttact gcacttcatt   1440
tttgaacaga tattagtgca acagacaaat gccaacgcat ttttttctgt ttaccggcaa   1500
gctgaagctt ttacgatccc cataccgccg ttgctgcaaa cctgccaaga aagagcagca   1560
gaaacaggtg tcattttgtg gtggaaagcc aagtaaagta aacagaagat ggaagatagt   1620
gaggaccagg gagtgaggca ggggacacat ggcccacgcc tccctgcaca ttttcgtgta   1680
taaatacagg tggatgcatc gctctcccag catccatcgg ttctctgctc tgttcatcca   1740
tagagtttcc tcctcttctc cttcagtgca aggtagagaa gagcatgtgt gtgtgtgtgt   1800
gtgaactgtg aagtgcagag tgcttctgta gttctgtgtt atgtccatag tgatcttgtt   1860
aggattgttg ctatggatgc atgatgttat ggttaatctc tgaattacag tagggacttc   1920
tctgagatct ctggattagt ggggggtgct aaatttttt ctggttgcat cagcttgggt    1980
ttctgggatt ggtgtgggtt cttgctctga attttggttc agaatgtcga tttgttttgt   2040
gtttgccctc tgaagttgag agtagctatg atccatccag cacagaactg caggtccctg   2100
cctgccggca gcatatacag gacatgccat tttgcaagct ctgggcttat ggtttctctt   2160
ttggagttct tcttcttgca tgatctgtgt tctctaacaa agaagcaaga tttagcaact   2220
ttattcagag acaagaaaag gatctggcaa ccttttgttt ctgttttatc ctactcgtaa   2280
agattgttat ttaagcaaaa atttcccaaa agttttaaat ataatttcca tgatgtgcca   2340
ctctcatgtc cttgaacctg gcactcatta tgggctcctc agaagtgctg tagctaatgt   2400
cactaatctt ttgtatcttt gttcgtagtc ttgtatttta tgatgcttat ccctttgtgc   2460
tttccatgtt tgatgtccaa atgtcatggc aatgtttttg acttctagta ggggttttag   2520
tacctttttg ttagataagt acatccaaat tctgtttatt tattcaaaaa tcattctgtt   2580
tattcactga aaacatttgt ccattcaatg gaatcgtaaa ctgtctgtgt ttttcaggct   2640
tgaggatcca actagaagat agcaatgg                                      2668
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 8

```
ggatcctaat acgactcact atagggc                                         27
```

<210> SEQ ID NO 9
<211> LENGTH: 17

```
<212> TYPE: DNA
<213> ORGANISM: Artificial Sequence
<220> FEATURE:
<223> OTHER INFORMATION: Description of Artificial Sequence: Primer

<400> SEQUENCE: 9
aatagggctc gagcggc                                                    17

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 10
gctttccacc acaaaatgac ac                                              22

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 11
cgaattctag taacatagat gacacc                                          26

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 12
ggaattcccc gatcgttcaa acatttgg                                        28

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 13
ggaagcttgc gaaaatgtgc aggg                                            24

<210> SEQ ID NO 14
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 14
cccatggcta tcttctagtt ggatcctcaa gccttgcact gaagggaag aggagg          56

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 15
```

```
cattttgctg ccggtc                                              16
```

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 16

```
caggaaacag ctatgac                                             17
```

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 17

```
ccgctagcac agaggctgag cag                                      23
```

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 18

```
tgctagctgg taaatgacat gctgctg                                  27
```

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 19

```
cgctagcaga ggcagcaagc tc                                       22
```

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 20

```
gggctagcga aaatgtgcag gg                                       22
```

<210> SEQ ID NO 21
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
ctaatacgac tcactatagg gctcgagcgg ccgcccgggc aggt               44
```

<210> SEQ ID NO 22
<211> LENGTH: 8
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 22 acctgccc                                                                    8

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 23
ctggcgaaag ggggatgtgc tg                                                   22

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 24
acgacggaat ggataatagc agata                                                25

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 25
gtttccccca tggctatctt c                                                    21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 26
cctccctgaa gcttttcgtg t                                                    21

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 27
attaggcacc ccaggcttta cactttatgc ttccggctcg tatg                           44

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 28
```

```
gtttccccca ttgctatctt c                                            21

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 29
agtgccaggt tcaaggaca                                               19

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 30
accaatccca gaaacccaag c                                            21

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 31
gtgtcccctg cctcactcc                                               19

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 32
ccggctaagt taaaaaaaaa                                              20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 33
ctgtgccgtt ggaagcgtca t                                            21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 34
cgcagatggg ttcagccttc a                                            21

<210> SEQ ID NO 35
<211> LENGTH: 20
<212> TYPE: DNA
<213> ORGANISM: Artificial Sequence
```

```
<220> FEATURE:
<223> OTHER INFORMATION: Description of Artificial Sequence: Primer

<400> SEQUENCE: 35
ggtcggcaca ttgagaggtc                                              20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 36
cacacccaac gctcaccgat g                                            21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 37
aggacggttt tggttgggat t                                            21

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 38
tcctcctctt ccccctccag tg                                           22

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 39
atctggcaac cttttgtttc t                                            21

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 40
caggaaacag ctatgac                                                 17

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 41
cgacgttgta aaacgacggc cagt                                         24
```

```
<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 42
acgacggaat ggataatagc agata                                         25

<210> SEQ ID NO 43
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gtcgaccatg g                                                        11
```